US009547009B2

(12) United States Patent
Wong et al.

(10) Patent No.: US 9,547,009 B2
(45) Date of Patent: Jan. 17, 2017

(54) BENZOCYCLOOCTYNE COMPOUNDS AND USES THEREOF

(71) Applicant: Academia Sinica, Taipei (TW)

(72) Inventors: Chi-Huey Wong, Rancho Santa Fe, CA (US); Jim-Min Fang, Taipei (TW); Jiun-Jie Shie, New Taipei (TW)

(73) Assignee: Academia Sinica (TW)

( * ) Notice: Subject to any disclaimer, the term of this patent is extended or adjusted under 35 U.S.C. 154(b) by 0 days.

(21) Appl. No.: 14/422,939

(22) PCT Filed: Aug. 21, 2013

(86) PCT No.: PCT/US2013/056018
§ 371 (c)(1),
(2) Date: Feb. 20, 2015

(87) PCT Pub. No.: WO2014/031762
PCT Pub. Date: Feb. 27, 2014

(65) Prior Publication Data
US 2015/0241439 A1    Aug. 27, 2015

Related U.S. Application Data

(60) Provisional application No. 61/691,262, filed on Aug. 21, 2012.

(51) Int. Cl.
G01N 33/58 (2006.01)
C07D 413/06 (2006.01)
C07D 311/78 (2006.01)
C07D 491/04 (2006.01)
C07D 493/04 (2006.01)
C07D 405/14 (2006.01)
C07D 311/94 (2006.01)
C07D 405/06 (2006.01)
C07D 495/04 (2006.01)
C07D 513/04 (2006.01)
A61K 49/00 (2006.01)

(52) U.S. Cl.
CPC ......... G01N 33/582 (2013.01); A61K 49/0032 (2013.01); C07D 311/78 (2013.01); C07D 311/94 (2013.01); C07D 405/06 (2013.01); C07D 405/14 (2013.01); C07D 413/06 (2013.01); C07D 491/04 (2013.01); C07D 493/04 (2013.01); C07D 495/04 (2013.01); C07D 513/04 (2013.01)

(58) Field of Classification Search
USPC ....................................................... 514/434
See application file for complete search history.

(56) References Cited

U.S. PATENT DOCUMENTS

| 3,773,919 A | 11/1973 | Boswell et al. |
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,975,278 A | 12/1990 | Senter et al. |
| 5,004,697 A | 4/1991 | Pardridge |
| 5,112,596 A | 5/1992 | Malfroy-Camine |
| 5,122,469 A | 6/1992 | Mather et al. |
| 5,229,275 A | 7/1993 | Goroff |
| 5,264,365 A | 11/1993 | Georgiou et al. |
| 5,268,164 A | 12/1993 | Kozarich et al. |
| 5,395,541 A | 3/1995 | Carpenter et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,580,717 A | 12/1996 | Dower et al. |
| 5,587,458 A | 12/1996 | King et al. |
| 5,591,669 A | 1/1997 | Krimpenfort et al. |
| 5,625,126 A | 4/1997 | Lonberg et al. |

(Continued)

FOREIGN PATENT DOCUMENTS

| EP | 404097 A2 | 12/1990 |
| EP | 1391213 A1 | 2/2004 |

(Continued)

OTHER PUBLICATIONS

Sletten et al., Difluorobenzocyclooctyne: Synthesis, Reactivity, and Stabilization by beta-Cyclodextrin, 2010, J. Am. Chem. Soc., vol. 132, No. 33, 11799-11805.*
Basolo et al., N,N-Disubstituted propargylamines as tools in the sequential 1,3-dipolar cycloaddition/arylation processes to the formation of polyheterocyclic systems, 2008, Tetrahedron, 64, 8182-8187.*
Agard et al., "A strain-promoted [3 + 2] azide-alkyne cycloaddition for covalent modification of biomolecules in living systems," J. Am. Chem. Soc., Nov. 24, 2004, 126(46):15046-15047.
Bach, "Ring strain energy in the cyclooctyl system. The effect of strain energy on [3 + 2] cycloaddition reactions with azides," J. Am. Chem. Soc., Apr. 15, 2009, 131(14):5233-5243.

(Continued)

Primary Examiner — Kristin Vajda
(74) Attorney, Agent, or Firm — Duane Morris LLP

(57) ABSTRACT

Provided are benzocyclooctyne compounds of formula (I). These compounds undergo strain-promoted azide-alkyne cyclo additions (SPAAC) without presence of toxic metal catalysts. The provided compounds are useful for diagnosis and imaging of azide-containing molecules. Methods for detection and imaging biomolecules using compounds of the present disclosure are disclosed.

26 Claims, 15 Drawing Sheets

(56) References Cited

U.S. PATENT DOCUMENTS

| | | | |
|---|---|---|---|
| 5,633,425 | A | 5/1997 | Lonberg et al. |
| 5,641,870 | A | 6/1997 | Rinderknecht et al. |
| 5,648,237 | A | 7/1997 | Carter |
| 5,661,016 | A | 8/1997 | Lonberg et al. |
| 5,674,988 | A | 10/1997 | Sabesan |
| 5,677,180 | A | 10/1997 | Robinson et al. |
| 5,686,416 | A | 11/1997 | Kozarich et al. |
| 5,733,743 | A | 3/1998 | Johnson et al. |
| 5,736,137 | A | 4/1998 | Anderson et al. |
| 5,821,337 | A | 10/1998 | Carter et al. |
| 5,837,234 | A | 11/1998 | Gentile et al. |
| 5,840,523 | A | 11/1998 | Simmons et al. |
| 5,869,046 | A | 2/1999 | Presta et al. |
| 6,004,940 | A | 12/1999 | Marasco et al. |
| 6,027,888 | A | 2/2000 | Georgiou et al. |
| 6,083,715 | A | 7/2000 | Georgiou et al. |
| 6,265,150 | B1 | 7/2001 | Terstappen et al. |
| 6,329,173 | B1 | 12/2001 | Marasco et al. |
| 6,528,286 | B1 | 3/2003 | Ryll |
| 6,703,019 | B1 | 3/2004 | Malfroy-Camine |
| 6,824,780 | B1 | 11/2004 | Devaux et al. |
| 6,984,630 | B1 | 1/2006 | Descamps et al. |
| 7,090,973 | B1 | 8/2006 | Breton |
| 7,151,164 | B2 | 12/2006 | Hansen et al. |
| 7,977,097 | B1 | 7/2011 | Gay et al. |
| 8,101,179 | B2 | 1/2012 | Numazaki et al. |
| 2002/0025313 | A1 | 2/2002 | Micklus et al. |
| 2002/0038086 | A1 | 3/2002 | Hynynen et al. |
| 2002/0065259 | A1 | 5/2002 | Schatzberg et al. |
| 2003/0073713 | A1 | 4/2003 | Schoenhard |
| 2003/0083299 | A1 | 5/2003 | Ferguson |
| 2003/0104402 | A1 | 6/2003 | Zauderer et al. |
| 2003/0118592 | A1 | 6/2003 | Ledbetter et al. |
| 2003/0129186 | A1 | 7/2003 | Beliveau et al. |
| 2003/0162695 | A1 | 8/2003 | Schatzberg et al. |
| 2003/0175884 | A1 | 9/2003 | Umana et al. |
| 2004/0072290 | A1 | 4/2004 | Umana et al. |
| 2004/0131692 | A1 | 7/2004 | Kreuter et al. |
| 2004/0204354 | A1 | 10/2004 | Nelson et al. |
| 2005/0089473 | A1 | 4/2005 | Black et al. |
| 2005/0106108 | A1 | 5/2005 | Hansen et al. |
| 2005/0123546 | A1 | 6/2005 | Umana et al. |
| 2005/0124533 | A1 | 6/2005 | Schatzberg et al. |
| 2006/0073122 | A1 | 4/2006 | Koezuka et al. |
| 2006/0073161 | A1 | 4/2006 | Breton |
| 2006/0286637 | A1 | 12/2006 | Hamilton |
| 2007/0224189 | A1 | 9/2007 | Lazar et al. |
| 2007/0238871 | A1 | 10/2007 | Tsuji et al. |
| 2009/0285837 | A1 | 11/2009 | Kao et al. |
| 2010/0068806 | A1 | 3/2010 | Laine et al. |
| 2010/0173323 | A1 | 7/2010 | Strome |
| 2011/0263828 | A1 | 10/2011 | Wong et al. |
| 2012/0171201 | A1 | 7/2012 | Sapra |
| 2012/0178705 | A1 | 7/2012 | Liang et al. |
| 2012/0178802 | A1 | 7/2012 | Withers |
| 2012/0226024 | A1 | 9/2012 | Wang et al. |
| 2012/0328646 | A1 | 12/2012 | Wong et al. |
| 2013/0196356 | A1 | 8/2013 | Jackson et al. |
| 2013/0230886 | A1 | 9/2013 | Votsmeier et al. |
| 2013/0337018 | A1 | 12/2013 | Fox |
| 2014/0086916 | A1 | 3/2014 | Zha |
| 2014/0127241 | A1 | 5/2014 | Leuschner et al. |

FOREIGN PATENT DOCUMENTS

| | | |
|---|---|---|
| JP | 05-339283 A | 12/1993 |
| JP | 11-343295 A | 12/1993 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 93/01161 A1 | 1/1993 |
| WO | WO 93/06213 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/17852 A1 | 5/1997 |
| WO | WO 98/02463 A1 | 1/1998 |
| WO | WO 98/24893 A2 | 6/1998 |
| WO | WO 99/57134 A1 | 11/1999 |
| WO | WO 03/068821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/103404 A1 | 12/2004 |
| WO | WO 2005/044859 | 5/2005 |
| WO | WO 2005/103081 A2 | 11/2005 |
| WO | WO 2006/126069 A2 | 11/2006 |
| WO | WO 2006/130458 A2 | 12/2006 |
| WO | WO 2007/146847 A2 | 12/2007 |
| WO | WO 2008/133857 A1 | 11/2008 |
| WO | WO 2011/005756 A1 | 1/2011 |
| WO | WO 2011/074621 A1 | 6/2011 |
| WO | WO-2011-136645 A1 | 11/2011 |
| WO | WO 2011/145957 A1 | 11/2011 |
| WO | WO 2013/011347 A1 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/181585 A2 | 12/2013 |
| WO | WO 2014/031762 A1 | 2/2014 |
| WO | WO 2014/078373 A1 | 5/2014 |
| WO | WO 2015/026484 A1 | 2/2015 |

OTHER PUBLICATIONS

Barglow et al., "Activity-based protein profiling for the functional annotation of enzymes," Nat. Methods, Oct. 2007, 4(10):822-827.

Baskin et al, "Bioorthogonal Click Chemistry: Covalent Labeling in Living Systems," QSAR Comb. Sci., 2007, 26(11-12):1211-1219.

Baskin et al., "Copper-free click chemistry: Bioorthogonal reagents for tagging azides," Aldrichimica Acta., 2010, 43(1):15-23.

Berge et al., "Pharmaceutical salts," J. Pharmaceutical Sciences, Jan. 1977, 66(1):1-19.

Best, "Click chemistry and bioorthogonal reactions: unprecedented selectivity in the labeling of biological molecules," Biochemistry, Jul. 21, 2009, 48(28):6571-6584.

Chao et al., "Tuning the optical properties of BODTPY dye through Cu(I) catalyzed azide-alkyne cycloaddition (CuAAC) reaction," Sci. China Chem., Jan. 2012, 55(1):125-130.

Chenoweth et al., "Cyclooctyne-based reagents for uncatalyzed click chemistry: A computational survey," Org. Biomol. Chem., Dec. 21, 2009, 7(24):5255-5258.

Codelli et al., "Second-generation difluorinated cyclooctynes for copper-free click chemistry," J. Am. Chem. Soc., Aug. 27, 2008, 130(34):11486-11493.

de Almeida et al., "Thiacycloalkynes for copper-free click chemistry," Angew. Chem. Int. Ed. Engl., Mar. 5, 2012, 51(10):2443-2447.

de Silva et al., "Signaling Recognition Events with Fluorescent Sensors and Switches," Chem. Rev., Aug. 5, 1997, 97(5):1515-1566.

Debets et al., "Bioconjugation with strained alkenes and alkynes," Acc. Chem. Res., Sep. 20, 2011, 44(9):805-815.

Demas et al., "Measurement of photoluminescence quantum yields. A Review," J. Phys. Chem., Apr. 15, 1971, 75(8):991-1024.

Dommerholt et al., "Readily accessible bicyclononynes for bioorthogonal labeling and three-dimensional imaging of living cells," Angew. Chem. Int. Ed. Engl., Dec. 3, 2010, 49(49):9422-9425.

Friscourt et al., "A fluorogenic probe for the catalyst-free detection of azide-tagged molecules," J. Am. Chem. Soc., Nov. 14, 2012, 134(45):18809-18815.

Gordon et al., "Reactivity of biarylazacyclooctynones in copper-free click chemistry," J. Am. Chem. Soc., Jun. 6, 2012, 134(22):9199-9208.

Hsu et al., "Alkynyl sugar analogs for the labeling and visualization of glycoconjugates in cells," Proc. Nat. Acad. Sci. U.S.A., Feb. 20, 2007, 104(8):2614-2619.

(56) References Cited

OTHER PUBLICATIONS

Jewett et al., "Rapid Cu-free click chemistry with readily synthesized biarylazacyclooctynones," *J. Am. Chem. Soc.*, Mar. 24, 2010, 132(11):3688-3690.
Jewett et al., "Synthesis of a fluorogenic cyclooctyne activate by Cu-free click chemistry," *Org. Lett.*, Nov. 18, 2011, 13(22):5937-5939.
King et al., "New tetramethylthiepinium (TMTI) for copper-free click chemistry," *Chem. Commun.*, Sep. 25, 2012, 48(74):9308-9309.
Kolb et al., "Click Chemistry: Diverse Chemical Function from a Few Good Reactions," *Angew. Chem. Int. Ed. Engl.*, Jun. 1, 2001, 40(11):2005-2021.
Le Droumaguet et al., "Fluorogenic click reaction," *Chem. Soc. Rev.*, Apr. 2010, 39(4):1233-1239.
Levi et al., "Bioorthogonal chemistry: recent progress and future directions," *Chem. Commun.*, Mar. 14, 2010, 46(10):1589-1600.
Murineddu et al., "Tricyclic pyrazoles. 3. Synthesis, biological evaluation, and molecular modeling of analogues of the cannabinoid antagonist 8-chloro-1-(2',4'-dichlorophenyl)-*N*-piperidin-1-yl-1,4,5,6-tetrahydrobenzo[6,7]cyclohepta[1,2-*c*]pyrazole-3-carboxamide," *J. Med. Chem.*, Nov. 17, 2005, 48(23):7351-7362.
Niederwieser et al., "Two-color glycan labeling of live cells by a combination of Diels-Alder and click chemistry," *Angew. Chem. Int. Ed.*, Apr. 8, 2013, 52(15):4265-4268.
Ning et al., "Visualizing metabolically labeled glycoconjugates of living cells by copper-free and fast huisgen cycloadditions," *Angew. Chem. Int. Ed. Engl.*, 2008, 47(12):2253-2255.
Poloukhtine et al., "Selective labeling of living cells by a phototriggered click reaction," *J. Am. Chem. Soc.*, Nov. 4, 2009, 131(43):15769-15776.
Prescher et al., "Chemistry in living systems," *Nat. Chem. Biol.*, Jun. 2005, 1(1):13-21.
Qi et al., "Developing visible fluorogenic 'click-on' dyes for cellular imaging." *Bioconjug. Chem.*, Sep. 21, 2011, 22(9):1758-1762.
Rostovtsev et al., "A stepwise huisgen cycloaddition process: copper(I)-catalyzed regioselective 'ligation' of azides and terminal alkynes," *Angew. Chem. Int. Ed. Engl.*, Jul. 15, 2002, 41(14):2596-2599.
Sawa et al., "Glycoproteomic probes for fluorescent imaging of fucosylated glycans in vivo," *Proc. Nat. Acad. Sci. U.S.A.*, Aug. 15, 2006, 103(33):12371-12376.
Shieh et al., "Fluorogenic azidofluoresceins for biological imaging," *J. Am. Chem. Soc.*, Oct. 24, 2012, 134(42):17428-17431.
Sivakumar et al., "A Fluorogenic 1,3-Dipolar Cycloaddition Reaction of 3-Azidocoumarins and Acetylenes," *Org. Lett.*, Nov. 4, 2004, 6(24):4603-4606.
Sletten et al., "Bioorthogonal Chemistry: Fishing for Selectivity in a Sea of Functionality," *Angew. Chem. Int. Ed. Engl.*, Aug. 27, 2009, 48(38):6974-6998.
Smith et al., "Some Exploratory Syntheses of Benzosuberans and Tetrahydrobenzazepinones and Some Related Diazoöxides," *J. Org. Chem.*, Jan. 1961, 26(1):27-36.
Stöckmann et al., "Development and evaluation of new cyclooctynes for cell surface glycan imaging in cancer cells," *Chem. Sci.*, May 2011, 2(5):932-936.
Tornøe et al., "Peptidotriazoles on solid phase: [1,2,3]-triazoles by regiospecific copper(I)-catalyzed 1,3-dipolar cycloadditions of terminal alkynes to azides," *J. Org. Chem.*, May 3, 2002, 67(9):3057-3064.
Tsai et al., "Cell-permeable probe for identification and imaging of sialidases," *Proc. Natl. Acad. Sci. U.S.A.*, Feb. 12, 2013, 110(7):2466-2471.
Varga et al., "A Non-Fluorinated Monobenzocyclooctyne for Rapid Copper-Free Click Reactions," *Chem. Eur. J.*, Jan. 16, 2012, 18(3):822-828.
Wu et al., "Catalytic azide-alkyne cycloaddition: Reactivity and applications," *Aldrichim. Acta*, 2007, 40(1):7-17.
Xie et al., "A fluorogenic 'click' reaction of azidoanthracene derivatives," *Tetrahedron*, Mar. 24, 2008, 64(13):2906-2914.
Zhou et al., "A fluorogenic probe for the copper(I)-catalyzed azide-alkyne ligation reaction: modulation of the fluorescence emission via $^3(n,\pi^*)$-$^1(\pi,\pi^*)$ inversion," *J. Am. Chem. Soc.*, Jul. 28, 2004, 126(29):8862-8863.
U.S. Appl. No. 15/011,543, filed Jan. 30, 2016, Chi-Huey Wong, et al.
U.S. Appl. No. 15/173,496, filed Jun. 3, 2016, Chi-Huey Wong, et al.
U.S. Appl. No. 15/005,930, filed Jan. 25, 2016, Chi-Huey Wong, et al.
U.S. Appl. No. 15/011,544, filed Jan. 30, 2016, Chi-Huey Wong, et al.
Abrahmsén et al, "Analysis of signals for secretion in the staphylococcal protein A gene," *EMBO J.*, Dec. 30, 1985, 4(13B):3901-3906.
Altschul SF et al., "Basic local alignment search tool", *J Mol Biol.* Oct. 5, 1990;215(3):403-10.
Altschul SF, et al., "Gapped BLAST and PSI-BLAST: A new generation of protein database search programs", *Nucleic Acids Res.* Sep. 1, 1997;25(17):3389-402.
Anderson et al., "Stimulation of Natural Killer T Cells by Glycolipids", *Molecules*, May 2013, 18(12), 15662-15688.
Arié et al., "Chaperone function of FkpA, a heat shock prolyl isomerase, in the periplasm of *Escherichia coli,*" *Mol. Microbiol.*, Jan. 2001, 39(1):199-210.
Bachmann, *Cellular and Molecular Biology*, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.
Baldwin et al., "Monoclonal antibodies in cancer treatment," *Lancet*, Mar. 15, 1986, 327(8481):603-605.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10): 4457-4461.
Barnes et al., "Methods for growth of cultured cells in serum-five medium," *Anal. Biochem.*, Mar. 1, 1980, 102(2):255-270.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996; 14(3):737-44.
Bass et al., "Hormone phage: An enrichment method for variant proteins with altered binding properties," *Proteins*, 1990, 8(4):309-314.
Beck A., "Biosimilar, biobetter and next generation therapeutic antibodies" *MAbs*. Mar.-Apr. 2011;3(2):107-10. Epub Mar. 1, 2011
Berra et al., "Correlation between ganglioside distribution and histological grading of human astrocytomas," *Int. J. Cancer*, Sep. 15, 1985, 36(3):363-366.
Birklé et al., "Role of tumor-associated gangliosides in cancer progression," *Biochimie*, Mar.-Apr. 2003, 85(3-4):455-463.
Bobo et al., "Convection-enhanced delivery of macromolecules in the brain," *Proc. Natl. Acad. Sci. U.S.A.*, Mar. 15, 1994, 91(6) 2076-2080.
Boerner et al., "Production of antigen-specific human monoclonal antibodies from in vitro-primed human splenocytes," *J. Immunol.*, Jul. 1, 1991, 147(1):86-95.
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Brennan et al., "Preparation of bispecific antibodies by chemical recombination of monoclonal immunoglobulin $G_1$ fragments," *Science*, Jul. 5, 1985, 229(4708):81-83.
Brimble et al., "The cell surface glycosphingolipids SSEA-3 and SSEA-4 are not essential for human ESC pluripotency," *Stem Cells*, Jan. 2007, 25(1):54-62.

(56) References Cited

OTHER PUBLICATIONS

Brodeur et al., *Monoclonal Antibody Production Techniques and Applications*, Chapter 4: Mouse-Human Myeloma Partners for the Production of Heterohybridomas, Schook, ed., 1987, pp. 51-63, Marcel Dekker, Inc., New York.
Brüggemann et al., "Designer mice: The production of human antibody repertoires in transgenic animals," *Year in Immunol.*, 1993, 7:33-40.
Capel PJ et al., "Heterogeneity of human IgG Fc receptors" *Immunomethods*. Feb. 1994;4(1):25-34.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol*. May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chen et al., "Chaperone activity of DsbC," *J. Bio. Chem.*, Jul. 9, 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Cancer Res*. 1989; 52:81-149.
Clynes R, et al., "Fc receptors are required in passive and active immunity to melanoma" *Proc Natl Acad Sci U S A*. Jan. 20, 1998;95(2):652-6.
Cunningham et al., "High-resolution epitope mapping of hGH-receptor interactions by alanine-scanning mutagenesis," *Science*, Jun. 2, 1989, 244(4908):1081-1085.
Daëron, "Fc receptor biology," *Annu. Rev. Immunol.*, 1997, 15:203-234.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: Amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: A dominant role for tyrosine in antigen recognition," *Proc. Natl. Acad. Sci. U.S.A.*, Aug. 24, 2004, 101(34):12467-12472.
Fishwild et al., "High-avidity human IgGκ monoclonal antibodies from a novel strain of minilocus transgenic mice," *Nature Biotechnol.*, Jul. 1996, 14(7):845-851.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.

Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujita M et al., "A novel disaccharide substrate having 1,2-oxazoline moiety for detection of transglycosylating activity of endoglycosidases" *Biochim Biophys Acta*. Sep. 3, 2001;1528(1):9-14.
Galfrè et al., "Preparation of monoclonal antibodies: strategies and procedures," *Methods Enzymol.*, 1981, 73(Pt B):3-46.
Gazzano-Santoro et al., "A non-radioactive complement-dependent cytotoxicity assay for anti-CD20 nonclonal antibody," *J. Immunol. Methods*, Mar. 28, 1997, 202(2): 163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gerson et al., "ESR. Spectra and Structures of Radical Anions in the Dibenzo [a, e]cyclooxtene Series," *Helvetica Chinica Acta*, Jan. 1, 1976, 59(6): 2038-2048.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice* 2$^{nd}$ *ed.*, Chapter 3: Production of Monoclonal Antibodies, 1986, pp. 59-103, Academic Press, London.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gottschling et al., "Stage-specific embryonic antigen-4 is expressed in basaloid lung cancer and associated with poor prognosis," *Eur. Respir. J.*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.

(56) References Cited

OTHER PUBLICATIONS

Harris, "Production of humanized monoclonal antibodies for in vivo imaging and therapy," *Biochem. Soc. Transactions*, Nov. 1995, 23(4):1035-1038.

Hawkins et al., "Selection of phage antibodies by binding affinity. Mimicking affinity maturation," *J. Mol. Biol.*, 1992, 226(3):889-896.

Heyman, "Complement and Fc-receptors in regulation of the antibody response," *Immunol. Lett.*, Dec. 1996, 54(2-3):195-199.

Hinman et al., "Preparation and characterization of monoclonal antibody conjugates of the calicheamicins: a novel and potent family of antitumor antibiotics," *Cancer Res.*, Jul. 15, 1993, 53(14):3336-3342.

Hogrefe et al., "A bacteriophage lambda vector for the cloning and expression of immunoglobulin Fab fragments on the surface of filamentous phage," *Gene*, Jun. 15, 1993, 128(1):119-126.

Holliger et al., "'Diabodies': small bivalent and bispecific antibody fragments," *Proc. Natl. Acad. Sci. U.S.A.*, Jul. 15, 1993, 90(14):6444-6448.

Honegger et al., "Yet another numbering scheme for immunoglobulin variable domains: an automatic modeling and analysis tool," *J. Mol. Biol.*, Jun. 8, 2001, 309:657-670.

Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.

Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.

Huang et al., "Carbohydrate-based vaccines with a glycolipid adjuvant for breast cancer," *Proc. Natl. Acad. Sci. U.S.A.*, Feb. 12, 2013, 110(7):2517-2522.

Hung et al., "Investigation of SSEA-4 binding protein in breast cancer cells," *J. Am. Chem. Soc.*, Apr. 24, 2013, 135(16):5934-5937.

Hurle et al., "Protein engineering techniques for antibody humanization," *Curr. Opin. Biotechnol.*, Aug. 1994, 5(4):428-433.

Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.

Jackson et al., "In vitro antibody maturation: Improvement of a high affinity, neutralizing antibody against IL-1β," *J. Immunol.*, Apr. 1, 1995, 154(7):3310-3319.

Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.

Jakobovits et al., "Germ-line transmission and expression of a human-derived yeast artificial chromosome," *Nature*, Mar. 18, 1993, 362(6417):255-258.

Jenkins N, Curling EM., "Glycosylation of recombinant proteins: problems and prospects", *Enzyme Microb Technol.* May 1994;16(5):354-64.

Jones et al., "Rapid PCR-cloning of full-length mouse immunoglobulin variable regions," *Nature Biotechnol.*, Jan. 1991, 9(1):88-89.

Jones et al., "Replacing the complementarity-determining regions in a human antibody with those from a mouse," *Nature*, May 29-Jun. 4, 1986, 321(6069):522-525.

Jones, "Analysis of polypeptides and proteins," *Adv. Drug Delivery Rev.*, Jan.-Apr. 1993, 10(1):29-90.

Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.

Kaneko et al., "Anti-inflammatory activity of immunoglobulin G resulting from Fc sialylation," *Science*, Aug. 4, 2006, 313(5787):670-673.

Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.

Kannagi et al., "Stage-specific embryonic antigens (Ssea-3 and -4) are epitopes of a unique globo-series ganglioside isolated from human teratocarcinoma cells,"*EMBO J.*, 1983, 2(12):2355-2361.

Karlin S. et al., "Methods for assessing the statistical significance of molecular sequence features by using general scoring schemes", *Proc Natl Acad Sci U.S.A.* Mar. 1990;87(6):2264-8.

Kato et al., "GMab-1, a high-affinity anti-3'-isoLM1/3'6'-isoLD1 IgG monoclonal antibody, raised in lacto-series ganglioside-defective knockout mice," Biochem. *Biophys. Res. Commun.*, Jan. 1, 2010, 391(1):750-755.

Kim et al., "Localization of the site of the murine IgG1 molecule that is involved in binding to the murine intestinal Fc receptor," *Eur. J. Immunol.*, 1994, 24:2429-2434.

Köhler et al., "Continuous cultures of fused cells secreting antibody of predefined specificity," *Nature*, Aug. 7, 1975, 256(5517):495-497.

Kontermann, "Intrabodies as therapeutic agents," *Methods*, Oct. 2004, 34(2):163-170.

Kostelny et al., "Formation of a bispecific antibody by the use of leucine zippers," *J. Immunol.*, Mar. 1, 1992, 148(5):1547-1553.

Kozbor, "A human hybrid myeloma for production of human monoclonal antibodies," *J. Immunol.*, Dec. 1984, 133(6):3001-3005.

Kriegler M et al., "A novel form of NF/cachectin is a cell surface cytotoxic transmembrane protein: ramifications for the complex physiology of TNF" *Cell.* Apr. 8, 1988;53(1):45-53.

Kudo et al., "Up-regulation of a set of glycosyltransferase genes in human colorectal cancer," *Lab. Invest.*, Jul. 1998, 78(7):797-811.

Lau et al., "N-Glycans in cancer progression," *Glycobiology*, Oct. 2008, 18(10):750-760.

Lee et al., "Bivalent antibody phage display mimics natural immunoglobulin," *J. Immunol. Methods*, Jan. 2004, 284(1-2):119-132.

Lee et al., "High-affinity human antibodies from phage-displayed synthetic Fab libraries with a single framework scaffold," *J. Mol. Biol.*, Jul. 23, 2004, 340(5):1073-1093.

Lefranc et al., "IMGT, the international ImMunoGeneTics database," *Nucleic Acids Res.*, Jan. 1, 1999, 27(1):209-212.

Lehninger, *Biochemistry: The Molecular Basis of Cell Structure and Function*, $2^{nd}$ ed., 1975, pp. 73-75, Worth Publishers, New York.

Leung et al., "A method for random mutagenesis of a defined DNA segment using a modified polymerase chain reaction," *Technique—A Journal of Methods in Cell and Molecular Biology*, Aug. 1989, 1(1):11-15.

Lindmark et al., "Binding of immunoglobulins to protein A and immunoglobulin levels in mammalian sera," *J. Immunol. Meth.*, Aug. 12, 1983, 62(1):1-13.

Liu C, et al., "Expansion of spleen myeloid suppressor cells represses NK cell cytotoxicity in tumor-bearing host" *Blood.* May 15, 2007;109(10):4336-42. Epub Jan. 23, 2007.

Tomlinson et al., "The repertoire of human germline $V_H$ sequences reveals about fifty groups of V segments with different hypervariable loops," *J. Mol. Biol.*, Oct. 5, 1992, 227(3):776-798.

LoBuglio et al., "Mouse/human chimeric monoclonal antibody in man: kinetics and immune response," *Proc. Natl. Acad. Sci. U.S.A.*, Jun. 1989, 86(11):4220-4224.

Lode et al., "Targeted therapy with a novel enediyene antibiotic calicheamicin $\Theta^I_1$ effectively suppresses growth and dissemination of liver metastases in a syngeneic model of murine neuroblastoma," *Cancer Res.*, Jul. 15, 1998, 58(14):2925-2928.

Lonberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Lou, et al., Stage-specific embryonic antigen-4 as a potential therapeutic target in glioblastoma multiforms and other cancers. Proc Natl Acad Sci USA 2014, 111(7):2482-7.

Louis et al., "The 2007 WHO classification of tumours of the central nervous system," *Acta. Neuropathol.*, Aug. 2007, 114(2):97-109.

(56) References Cited

OTHER PUBLICATIONS

Lu et al., "Single chain anti-c-Met antibody conjugated nanoparticles for in vivo tumor-targeted imaging and drug delivery," *Biomaterials*, Apr. 2011, 32(12):3265-3274.
Macfarlane GT, et al., "Formation of glycoprotein degrading enzymes by Bacteroides fragilis" *FEMS Microbiol Lett.* Jan. 15, 1991;61(2-3):289-93.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Månsson et al., "Characterization of new gangliosides of the lactotetraose series in murine xenografts of a human glioma cell line," *FEBS Lett.*, May 26, 1986, 201(1):109-113.
Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.
Marks et al., "By-passing immunization. Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 10, 1992(7):779-783.
Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 23, 1980,(1):243-252.
Matsuda et al., "Structure and physical map of 64 variable segments in the 3' 0.8-megabase region of the human immunoglobulin heavy-chain locus," *Nature Genet.*, Jan. 3, 1993,(1):88-94.
McCafferty et al., "Phage antibodies: Filamentous phage displaying antibody variable domains," *Nature*, Dec. 6, 1990, 348:552-554.
Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 8, 1969,(6):2518-2524.
Meyer, "Malignant gliomas in adults," *N. Engl. J. Med.*, Oct. 23, 2008, 359(17):1850.
Mimura et al., "Role of oligosaccharide residues of IgG1—Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Morelle, W. et al., "The Mass Spectrometric Analysis of Glycoproteins and their Glycan Sturctures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology.* Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 24, 1992(1-2):107-117.

Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Munson et al., "Ligand: a versatile computerized approach for characterization of ligand-binding systems," *Anal. Biochem.*, Sep. 1, 1980, 107(1):220-239.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 14, 1996(7):826.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Noto et al., "CD44 and SSEA-4 positive cells in an oral cancer cell line HSC-4 possess cancer stem-like cell characteristics," *Oral Oncol.*, Aug. 2013, 49(8):787-795.
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Papanastassiou et al., "The potential for efficacy of the modified (ICP 34.5$^-$) herpes simplex virus HSV1716 following intratumoural injection into human malignant glioma: a proof of principle study,"*Gene Therapy*, Mar. 9, 2002(6);398-406.
Pearlman et al., *Peptide and Protein Drug Delivery*, Chapter 6: Analysis of Protein Drugs, Lee, ed., 1991, pp. 247-301, Marcel Dekker Publishing, New York.
Peipp et al., "Antibody fucosylation differentially impacts cytotoxicity mediated by NK and PMN effector cells," *Blood*, 2008, 112(6):2390-2399.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology*, vol. 113: The Pharacology of Monoclonal Antibodies, Chapter 11: Antibodies from *Escherichia coli*, Rosenberg et al., eds., 1994, pp. 269-315, Springer-Verlag, Berlin.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Proba et al., "Functional antibody single-chain fragments from the cytoplasm of *Escherichia coli*: influence of thioredoxin reductase (TrxB)," *Gene*, Jul. 4, 1995, 159(2):203-207.
Puigbò P, Guzmán E, Romeu A, Garcia-Vallvé S. Optimizer: a web server for optimizing the codon usage of DNA sequences. *Nucleic Acids Res*. Jul. 2007;35(Web Server issue):W126-31. Epub Apr. 16, 2007.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.

(56) References Cited

OTHER PUBLICATIONS

Riechmann et al., "Reshaping human antibodies for therapy," *Nature*, Mar. 24, 1988, 332(6162):323-327.
Roguska et al., "Humanization of murine monoclonal antibodies through variable domain resurfacing," *Proc. Natl. Acad. Sci. U.S.A.*, Feb. 1, 1994, 91(3):969-973.
Roos et al., "Specific inhibition of the classical complement pathway by C1q-binding peptides," *J. Immunol.*, Dec. 15, 2001, 167(12):7052-7059.
Rowland et al, "Drug localisation and growth inhibition studies of vindesine-monoclonal anti-CEA conjugates in a human tumour xenograft," *Cancer Immunol. Immunother.*, 1986, 21(3):183-187.
Ruiz et al., "IMGT, the international ImMunoGeneTics database," *Nucl. Acids Res.*, Jan. 1, 2000, 28(1):219-221.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups*, Chapter 8: P System, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 21, 1990(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 20, 1980(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 5, 1993(2):256-262.
Slamon DJ, et al., "Human breast cancer: correlation of relapse and survival with amplification of the HER-2/neu oncogene" *Science*. Jan. 9, 1987; 235(4785):177-82.
Smith RA et al., "The active form of tumor necrosis factor is a trimer" *J Biol Chem.* May 25, 1987;262(15):6951-4.
Smyth MJ, et al., "CD4+CD25+ T regulatory cells suppress NK cell-mediated immunotherapy of cancer" *J Immunol.* Feb. 1, 2006;176(3):1582-7.

Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2): 109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Taylor-Papadimitriou et al., "Exploiting altered glycosylation patterns in cancer: Progress and challenges in diagnosis and therapy," *Trends Biotechnol.*, Jun. 12, 1994(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Traunecker et al., "Bispecific single chain molecules (Janusins) target cytotoxic lymphocytes on HIV infected cells," *EMBO J.*, Dec. 10, 1991(12):3655-3659.
Traylor et al., "Gangliosides of human cerebral astrocytomas," *J. Neurochem.*, Jan. 1980, 34(1):126-131.
Tsai Ti, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.
Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology*. Jan 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem*. Jul. 5, 1989;264(19):11282-7.
van Beek et al., "Increased sialic acid density in surface glycoprotein of transformed and malignant cells—a general phenomenon?" *Cancer Res.*, Nov. 1973, 33(11):2913-2922.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity,"*Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Wang et al., "Glycan microarray of Globo H and related structures for quantitative analysis of breast cancer," *Proc. Natl. Acad. Sci. U.S.A.*, Aug. 19, 2008, 105(33):11661-11666.
Ward et al., "Binding activities of a repertoire of single immunoglobulin variable domains secreted from *Escherichia coli,*" *Nature*, Oct. 12, 1989, 341(6242):544-546.
Waterhouse et al., "Combinatorial infection and in vivo recombination. a strategy for making large phage antibody repertoires," *Nuc. Acids Res.*, May 11, 1993, 21(9):2265-2266.
Wikstrand et al., "Monoclonal antibody therapy of human gliomas: Current status and future approaches," *Cancer Metastasis Rev.*, 1999, 18(4):451-464.

(56) References Cited

OTHER PUBLICATIONS

Williams et al., "Cloning and sequencing of human immunoglobulin V lambda gene segments." *Eur. J. Immunol.*, Jul. 23, 1993(7):1456-1461.
Winter et al., "Making antibodies by phage display technology," *Annu. Rev. Immunol.*, 1994, 12:433-455.
Woof et al., "Human antibody-Fc receptor interactions illuminated by crystal structures," *Nat. Rev. Immunol.*, Feb. 4, 2004(2):89-99.
Yansura et al., "Nucleotide sequence selection for increased expression of heterologous genes in *Escherichia coli*," *Methods: A Companion to Methods in Enzymol.*, Aug. 4, 1992(2):151-158.
Ye et al., "Stage-specific embryonic antigen 4 expression in epithelial ovarian carcinoma," *Int. J. Gynecol. Cancer*, Aug. 20, 2010(6):958-964.
Yelton et al., "Affinity maturation of the BR96 anti-carcinoma antibody by codon-based mutagenesis." *J. Immunol.*, Aug. 15, 1995, 155(4):1994-2004.
Yu et al., "Anti-GD2 antibody with GM-CSF, interleukin-2, and isotretinoin for neuroblastoma," *N. Engl. J. Med.*, Sep. 30, 2010, 363(14):1324-1334.
Zapata et al., "Engineering linear F(ab')$_2$ fragments for efficient production in *Escherichia coli* and enhanced antiproliferative activity," *Protein Eng.*, Oct. 8, 1995(10): 1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 20, 2010(1):118-126.
Zhang et al., "Selection of tumor antigens as targets for immune attack using immunohistochemistry: I. Focus on gangliosides," *Int. J. Cancer*, Sep. 26, 1997, 73(1):42-49.
Zou, et al., Chemoenzymatic synthesis and Fc gamma receptor binding of homogenous glycoforms of antibody Fc domain Presence of a bisecting sugar moiety enhances the affinity of Fc to FcIIIa receptor. J Am Chem Soc. 2011, 133(46):18975-91.
Written Opinion in International Patent Application No. PCT/US2013/055472, mailed Dec. 23, 2013, in 7 pages.
International Search Report and Written Opinion issued for International application No. PCT/US2015/032738, Oct. 20, 2015, 15 pages.
International Search Report and Written Opinion issued for International application No. PCT/US2015/032744, Oct. 2, 2015, 12 pages.
International Search Report and Written Opinion issued for International application No. PCT/US2015/032740, Oct. 26, 2015, 13 pages.
International Search Report and Written Opinion issued for International application No. PCT/US2015/032737, Oct. 1, 2015, 13 pages.
International Search Report and Written Opinion issued for International application No. PCT/US2015/032745, Oct. 8, 2015, 13 pages.
International Search Report issued for International application No. PCT/US2015/049014, Dec. 14, 2015, 3 pages.
International Search Report and Written Opinion in International Application No. PCT/US2016/015858, dated Jun. 27, 2016, in 8 pages.
European Search Report issued in connection with corresponding European Patent Application No. 15181446.4, Dec. 7, 2015, 10 pages.
Extended European Search Report dated Jan. 5, 2016 in European Patent Application No. 13830785.5, in 10 pages.

* cited by examiner

Table 1. Spectroscopic properties of probe 1 and triazoles 1-A, 1-B

| | Absorption ($\lambda_{max}$, nm) | $\varepsilon$ (M$^{-1}$ cm$^{-1}$)[a] | Emission ($\lambda_{max}$, nm) | Stokes shift (nm) | $\Phi_f$[b] |
|---|---|---|---|---|---|
| 1 | 336 | 7800 | 405 | 69 | 0.011 |
| 1-A | 328 | 13200 | 435 | 107 | 0.23 |
| 1-B | 330 | 10800 | 435 | 105 | 0.21 |

[a] Extinction coefficient; measured at 340 nm for 1, and at 330 nm for 1-A and 1-B

[b] Fluorescence quantum yield; quinine sulfate as standard.

BENZOCYCLOOCTYNE COMPOUNDS AND USES THEREOF

RELATED APPLICATIONS

The present application is a U.S. national stage application under 35 U.S.C. §371 of PCT Application No. PCT/US2013/056018, filed Aug. 21, 2013, which claims priority to U.S. Provisional Application No. 61/691,262, filed on Aug. 21, 2012, the contents of each of which are incorporated herein in their entirety.

TECHNICAL FIELD OF THE PRESENT DISCLOSURE

The present disclosure relates to benzocyclooctyne compounds and their application in diagnosis and imaging of azide-containing molecules.

BACKGROUND OF THE PRESENT DISCLOSURE

Copper-catalyzed azide-alkyne 1,3-dipolar cycloaddition (CuAAC) has gained widespread use in chemical biology for applications such as labeling of biomolecules in complex mixtures and imaging of fixed cells and tissues. (Kolb, et al., *Angew. Chem. Int. Ed.* 2001, 40, 2004; Rostovtsev, et al., *Angew. Chem. Int. Ed.* 2002, 41, 2596; Wu and Fokin, *Aldrichimica Acta* 2007, 40, 7.) Incorporation of fluorescent probes into proteins, DNA, RNA, lipids and glycans within their native cellular environments provides opportunities for imaging and understanding their roles in vivo. (Best, *Biochemistry* 2009, 48, 6571.)

For example, glycans in proteins are displayed on the cell surface with implications in numerous physiological and pathological processes. Aberrant glycosylation on the surface of diseased cells is often observed in pathological conditions, such as inflammation and cancer metastasis. In particular, altered terminal sialylation and fucosylation, which are believed to result from changes in expression locations and levels of sialyltransferases and fucosyltransferases, are associated with tumor malignancy. The ability to explore the biological information content of glycans as biomarkers of cancer, attached to either proteins or lipids, has become a major course of glycomics research. (Hsu, et al., *Proc. Nat. Acad. Sci. U.S.A.*, 2007, 104, 2614; Sawa, et al., *Proc. Nat. Acad. Sci. U.S.A.*, 2006, 103, 12371.)

Analysis of changes in glycosylation patterns in living systems is now possible. (Prescher and Bertozzi, *Nat. Chem. Bio.* 2005, 1, 13.) Metabolic incorporation of an unnatural carbohydrate containing unique functional group that acts as a bioorthogonal chemical reporter into the cell biosynthetic machinery initiates the process. The modified glycan is then processed and constructed on the cell surface. Subsequent reaction with a detectable fluorescent probe equipped with a complementary bioorthogonal functional group enables detection of the incorporated unnatural glycan (FIG. 1). (Sletten and Bertozzi, *Angew. Chem. Int. Ed.* 2009, 48, 6974-98.)

The concept of bioorthogonal chemical reporter has been applied to proteomic analysis of glycosylation in proteins and chemical remodeling of cell surfaces in living systems. Bioorthogonal chemical reactions have also been used for other applications, such as protein labeling, activity-based protein folding, protein targets identification, posttranslational modifications, and cell proliferation monitoring. Labeling of specific functional groups on living cell via bioorthogonal chemical reporter strategies have become increasingly powerful in cell biology. These approaches are often based on cycloadditions as ideal bioorthogonal reactions because of their intrinsic selectivity and tunable electronics. However, there are still many challenges facing the field. For example, most bioorthogonal reporter strategies entail multistep procedures that use fluorophroe-labeled reactant partners, which often cause high background fluorescent noise that is difficult to remove from intracellular environments or tissues. In addition, these methods require high concentrations of reagents and catalysts in order to achieve detectable signals.

Some recent efforts have been focused on the design of fluorogenic CuAAC reactions between non-fluorescent alkyne and azide, which can ligate to afford a highly fluorescent triazole complex (FIG. 1). (Sivakumar, et al., *Org. Lett.* 2004, 24, 4603; Sawa, et al., *Proc. Nat. Acad. Sci. U.S.A.*, 2006, 103, 12371; Xie, et al., *Tetrahedron* 2008, 64, 2906; Li, et al., *Org. Lett.* 2009, 11, 3008; Le Droumaguet, et al., *Chem. Soc. Rev.* 2010, 39, 1223; Chao, et al., *Sci. China Chemistry* 2012, 55, 125.) This type of CuAAC reaction occurring in high efficiency would have broad applications in the emerging field of cell biology and functional proteomics due to the distinct fluorescence properties in formation of the triazole without background fluorescent noise of the starting materials. Unfortunately, the use of CuAAC reactions in living systems has been hindered because the reactions require toxic copper(I) ion as the catalyst.

To circumvent the cytotoxicity associated with metal catalyst, the ring strain-promoted azide-alkyne cycloadditions (SPAAC) without using metal catalyst have been developed. (Agard, et al., *J. Am. Chem. Soc.* 2004, 126, 15046; Codelli, et al., *J. Am. Chem. Soc.* 2008, 130, 11486; Debets, et al., *Acc. Chem. Res.* 2011, 44, 805; Dommerholt, et al., *Angew. Chem. Int. Ed.* 2010, 49, 9422; Friscourt, et al., *J. Am. Chem. Soc.* 2012, 134, 5381; Jewett, et al., *J. Am. Chem. Soc.* 2010, 132, 3688; Ning, et al., *Angew. Chem. Int. Ed.* 2008, 47, 2253; Poloukhtine, et al., *J. Am. Chem. Soc.* 2009, 131, 15769; Varga, et al., *Chem. Eur. J.* 2012, 18, 822.) A cyclooctyne moiety is often incorporated as a stem structure into the SPAAC reagents, such as difluorinated cyclooctynes (DIFO) and the derivatives. An attempt toward this approach was reported by Bertozzi and co-workers using the biarylazacyclooctynone ring fused with a coumarin fluorophore (J. C. Jewett, C. R. Bertozzi, *Org. Lett.* 2011, 13, 5937-5939). Although the compound undergoes a cycloaddition reaction with 2-azidoethanol to give a 10-fold increase in fluorescence intensity, the triazole product exhibited a low quantum yield ($\Phi_f$=0.04) and required relatively high energy excitation (~300 nm), making it unsuitable for imaging in living systems.

SUMMARY OF THE PRESENT DISCLOSURE

The present disclosure relates to novel benzocyclooctyne compounds of formula (I) that undergo strain-promoted azide-alkyne cycloadditions (SPAAC) without using toxic metal catalyst. Exemplary coumarin-cyclooctyne compounds according to the present disclosure react with azide compounds to give the triazole products with enhanced fluorescence to facilitate the detection and imaging. The provided compounds represent a significant advance in live-cell imaging and are applicable to real-time detection of biochemical events in vivo.

One aspect of the present disclosure relates to a compound of Formula (I):

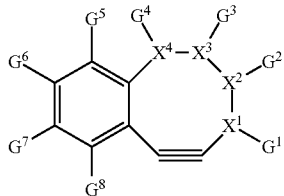

or a salt thereof, wherein $X^1$, $X^2$, $X^3$, $X^4$, $G^1$, $G^2$, $G^3$, $G^4$, $G^5$, $G^6$, $G^7$ and $G^8$ are as described herein.

In some embodiments, the compound is of formula (II).

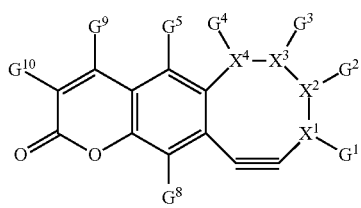

or a salt thereof, wherein $X^1$, $X^2$, $X^3$, $X^4$, $G^1$, $G^2$, $G^3$, $G^4$, $G^5$, $G^6$, $G^7$, $G^8$, $G^9$ and $G^{10}$ are as described herein.

In certain embodiments, the provided compound is Compound 1 or Compound 2 shown below:

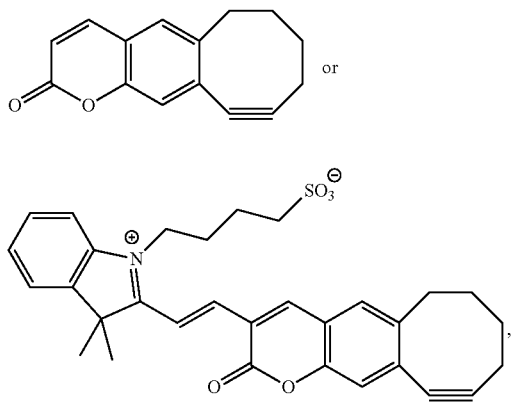

or a salt thereof.

In another aspect, the present disclosure present disclosure provides synthetic methods for preparation of benzocyclooctyne compounds. The present disclosure also demonstrates that the benzocyclooctyne compounds described herein react with organic azides to form triazole products with enhanced fluorescence.

In yet another aspect, present disclosure the present disclosure relates to methods for detecting and/or imaging biomolecules.

In certain embodiments, the present disclosure present disclosure provides a method for imaging an azide-containing molecule, the method comprising
(a) incubating a compound as described herein with a sample containing the azide-containing molecule under conditions allowing for ligation of the compound to an azido group of the molecule to form a triazole product; and
(b) detecting a fluorescent signal released from the triazole product.

In certain embodiments, the present disclosure present disclosure provides a method for detecting an azide-containing molecule in a sample, the method comprising:
(a) contacting a compound as described herein to a sample suspected of having an azide-containing molecule;
(b) detecting a level of a fluorescent signal released from the sample, and
(c) determining presence of the azide-containing molecule in the sample, wherein an enhanced fluorescent signal as compared to a level of the fluorescent signal in the absence of the compound indicates presence of the azide-containing molecule.

In certain embodiments, the compound used in the methods of imaging or detecting an azide-containing molecule as described herein is Compound 1 or Compound 2, or a salt thereof.

DEFINITIONS

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The present disclosure additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

As used herein, "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl and 2-naphthyl). In some embodiments, an aryl group has 14 ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted C$_{6-14}$ aryl. In certain embodiments, the aryl group is a substituted C$_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present present disclosure contemplates any and all such combinations in order to arrive at a stable compound. For purposes of this present disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N $(R^{bb})_2$, —OP(=O)$_2$N($R^{bb}$)$_2$, —P(=O)(N$R^{bb}$)$_2$, —OP(=O)(N$R^{bb}$)$_2$, —N$R^{bb}$P(=O)(O$R^{cc}$)$_2$, —N$R^{bb}$P(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —B$R^{aa}$(O$R^{cc}$), $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$heteroalkynyl, $C_{3-14}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$heteroalkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$R, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$heteroalkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+X^-$, —N(O$R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —NH$_2$($C_{1-6}$ alkyl)$^+X^-$, —NH$_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$alkyl), —C(=O)NH$_2$, —C(=O)N($C_{1-6}$ alkyl)$_2$, —OC(=O)NH($C_{1-6}$ alkyl), —NHC(=O)($C_{1-6}$alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$alkyl), —OC(=NH)($C_{1-6}$alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2C_{1-6}$ alkyl, —SO$_2$O$C_{1-6}$ alkyl, —OSO$_2C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

As used herein, the term "halo" or "halogen" refers to fluorine (fluoro, —F), chlorine (chloro, —Cl), bromine (bromo, —Br), or iodine (iodo, —I).

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4'-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, when two entities are "conjugated" or "ligated" to one another, they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. In certain embodiments, two entities are covalently connected, optionally through a linker group.

As used herein, the term "salt" refers to any and all salts, including pharmaceutically acceptable salt which refers to those salts within the scope of sound medical judgment, suitable for use in contact with the tissues of humans and lower animals without undue toxicity, irritation, allergic response and the like, and are commensurate with a reasonable benefit/risk ratio (see Berge et al. describes pharmaceutically acceptable salts in detail in *J. Pharmaceutical Sciences* (1977) 66:1-19). Examples of pharmaceutically acceptable, nontoxic acid salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

As used herein, the terms "condition," "disease," and "disorder" are used interchangeably.

As used herein "inhibition", "inhibiting", "inhibit" and "inhibitor", and the like, refer to the ability of a compound to reduce, slow, halt, or prevent the activity of a particular biological process.

As used herein, the term "cell" present disclosure is meant to encompass eukaryotic and prokaryotic cells of any genus or species, with mammalian cells being of particular interest. "Cell" is also meant to encompass both normal cells and diseased cells, e.g., cancerous cells. In certain embodiments, the cells described herein are living cells.

As used herein the term "sample" includes any chemical sample or biological sample. Chemical sample refers to any chemical mixtures or chemical compounds. Biological sample includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

The term "physiological conditions" is meant to encompass those conditions compatible with living cells, e.g., predominantly aqueous conditions of a temperature, pH, salinity, etc. that are compatible with living cells.

BRIEF DESCRIPTION OF THE DRAWINGS

FIG. 6 is a table showing the spectroscopic properties of Compound 1 and compounds 1-A and 1-B.

DETAILED DESCRIPTION OF THE PRESENT DISCLOSURE

Figure 1:
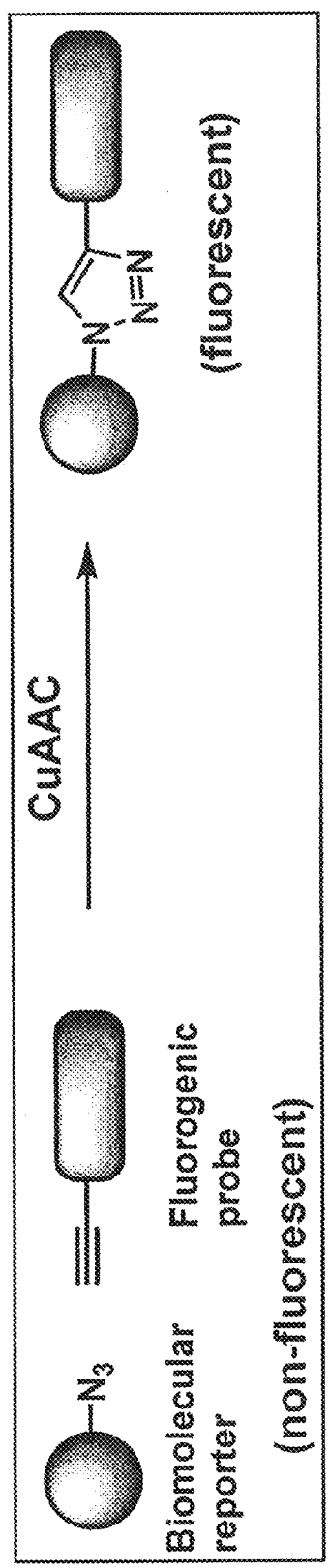
FIG. 1 is a schematic representation of a fluorogenic CuAAC reaction.

The present disclosure provides novel benzocyclooctyne compounds of formula (I). These compounds undergo strain-promoted azide-alkyne cycloadditions (SPAAC) without presence of toxic metal catalyst. Exemplary coumarin-cyclooctyne compounds according to the present disclosure react with azide compounds to give the triazole products with enhanced fluorescence to facilitate the detection in a target molecule. The provided compounds represent a significant advance in live-cell imaging, and are applicable to real-time detection of biochemical events in vivo.

In one aspect, the present disclosure provides a compound of Formula (I):

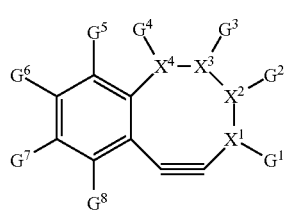

or a salt thereof,
wherein
$X_1$, $X_2$, $X_3$, and $X_4$ are in a 8-membered carbocycle or heterocycle; provided that when the 8-membered ring is a heterocycle, three of $X_1$, $X_2$, $X_3$, and $X_4$ are carbon atoms, and one of $X_1$, $X_2$, $X_3$, and $X_4$ is N, O, P, or S;

each of $G^1$, $G^2$, $G^3$ and $G^4$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, =O, =NOH, =N—OR$^A$, =N—NH$_2$, =N—NHR$^B$, =N—N(R$^B$)$_2$, and —NHSO$_2$R$^A$; or $G^1$ and $G^2$ are taken together with their intervening atoms to form an optionally substituted carbocycle or heterocycle; or $G^3$ and $G^4$ are taken together with their intervening atoms to form an optionally substituted carbocycle or heterocycle;

each of $G^5$ and $G^8$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, and —NHSO$_2$R$^A$;

each of $G^6$ and $G^7$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, and —NHSO$_2$R$^A$, or $G^6$ and $G^7$ are taken together with their intervening atoms to form an optionally substituted carbocycle or heterocycle;

each instance of $R^A$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or an oxygen protecting group when attached to an oxygen, or a sulfur protecting group when attached to sulfur; and each instance of $R^B$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or a nitrogen protecting group, or two $R^B$ taken together with the intervening nitrogen form a heterocycle;

each instance of $R^C$ is independently hydrogen, optionally substituted $C_1$-$C_6$ alkyl, optionally substituted alkenyl, optionally substituted alkynyl, optionally substituted heterocyclyl, optionally substituted aryl, or optionally substituted heteroaryl; and provided that when $G^1$ and $G^2$ are taken together with their intervening atoms to form an optionally substituted phenyl, $G^6$ and $G^7$ are taken together with their intervening atoms to form an optionally substituted heterocycle and $X^4$ is not N.

For the compounds of formula (I), when $G^1$ and $G^2$ are taken together with their intervening atoms to form an optionally substituted phenyl, $G^6$ and $G^7$ are taken together with their intervening atoms to form an optionally substituted heterocycle and $X^4$ is not N.

As generally defined herein, $X_1$, $X_2$, $X_3$, and $X_4$ are in a 8-membered carbocycle or heterocycle; provided that when the 8-membered ring is a heterocycle, three of $X_1$, $X_2$, $X_3$, and $X_4$ are carbon atoms, and one of $X_1$, $X_2$, $X_3$, and $X_4$ is N, O, P, or S. In certain embodiments, $X_1$, $X_2$, $X_3$, and $X_4$ are in a 8-membered carbocycle. In certain embodiments, $X_1$, $X_2$, $X_3$, and $X_4$ are in a 8-membered heterocycle. In certain embodiments, $X_1$, $X_2$, and $X_3$ are carbon atoms, and $X_4$ is N, O, P, or S. In certain embodiments, $X_1$, $X_2$, and $X_4$ are carbon atoms, and $X_3$ is N, O, P, or S. In certain embodiments, $X_1$, $X_3$, and $X_4$ are carbon atoms, and $X_2$ is N, O, P, or S. In certain embodiments, $X_2$, $X_3$, and $X_4$ are carbon atoms, and $X_1$ is N, O, P, or S.

As generally defined herein, $G^1$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)

$OR^A$, —S(O)$R^C$, —SO$_2R^A$, —SO$_2$N($R^B$)$_2$, =O, =NOH, =N—$OR^A$, =N—NH$_2$, =N—NH$R^B$, =N—N($R^B$)$_2$, and —NHSO$_2R^A$. In certain embodiments, $G^1$ is H. In certain embodiments, $G^1$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —CH$_2OR^A$, —OC(O)$R^C$, —S$R^A$, —N($R^B$)$_2$, —N($R^B$)C(O)$R^C$, —C(O)N($R^B$)$_2$, —CN, —NO$_2$, —C(O)$R^C$, —C(O)$OR^A$, —S(O)$R^C$, —SO$_2R^A$, —SO$_2$N($R^B$)$_2$, =O, =NOH, =N—$OR^A$, =N—NH$_2$, =N—NH$R^B$, =N—N($R^B$)$_2$, and —NHSO$_2R^A$. In certain embodiments, $G^1$ is halogen. In certain embodiments, $G^1$ is optionally substituted $C_1$-$C_6$ alkyl. In certain embodiments, $G^1$ is methyl, ethyl, or n-propyl. In certain embodiments, $G^1$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or an oxygen protecting group when attached to an oxygen, or a sulfur protecting group when attaching to sulfur. In certain embodiments, $G^1$ is —OH. In certain embodiments, $G^1$ is —$OR^A$, wherein $R^A$ is optionally substituted $C_1$-$C_6$ alkyl. In certain embodiments, $G^1$ is —OCH$_3$ or —OC$_2$H$_5$. In certain embodiments, $G^1$ is —$OR^A$, wherein $R^A$ is an oxygen protecting group. In certain embodiments, $G^1$ is —N($R^B$)$_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^1$ is NH$_2$. In certain embodiments, $G^1$ is NH$R^B$, wherein $R^B$ is optionally substituted $C_1$-$C_6$ alkyl. In certain embodiments, $G^1$ is NHCH$_3$ or NHC$_2$H$_5$. In certain embodiments, $G^1$ is NH$R^B$, wherein $R^B$ is a nitrogen protecting group.

As generally defined herein, $G^2$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —CH$_2OR^A$, —OC(O)$R^C$, —S$R^A$, —N($R^B$)$_2$, —N($R^B$)C(O)$R^C$, —C(O)N($R^B$)$_2$, —CN, —NO$_2$, —C(O)$R^C$, —C(O)$OR^A$, —S(O)$R^C$, —SO$_2R^A$, —SO$_2$N($R^B$)$_2$, =O, =NOH, =N—$OR^A$, =N—NH$_2$, =N—NH$R^B$, =N—N($R^B$)$_2$, and —NHSO$_2R^A$. In certain embodiments, $G^2$ is H. In certain embodiments, $G^2$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —CH$_2OR^A$, —OC(O)$R^C$, —S$R^A$, —N($R^B$)$_2$, —N($R^B$)C(O)$R^C$, —C(O)N($R^B$)$_2$, —CN, —NO$_2$, —C(O)$R^C$, —C(O)$OR^A$, —S(O)$R^C$, —SO$_2R^A$, —SO$_2$N($R^B$)$_2$, =O, =NOH, =N—$OR^A$, =N—NH$_2$, =N—NH$R^B$, =N—N($R^B$)$_2$, and —NHSO$_2R^A$. In certain embodiments, $G^2$ is halogen. In certain embodiments, $G^2$ is optionally substituted $C_1$-$C_6$ alkyl. In certain embodiments, $G^2$ is methyl, ethyl, or n-propyl. In certain embodiments, $G^7$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^2$ is —OH. In certain embodiments, $G^2$ is —$OR^A$, wherein $R^A$ is optionally substituted $C_1$-$C_6$ alkyl. In certain embodiments, $G^2$ is —OCH$_3$ or —OC$_2$H$_5$. In certain embodiments, $G^2$ is —$OR^A$, wherein $R^A$ is an oxygen protecting group. In certain embodiments, $G^2$ is —N($R^B$)$_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^2$ is NH$_2$. In certain embodiments, $G^2$ is NH$R^B$, wherein $R^B$ is optionally substituted $C_1$-$C_6$ alkyl. In certain embodiments, $G^2$ is NHCH$_3$ or NHC$_2$H$_5$. In certain embodiments, $G^2$ is NH$R^B$, wherein $R^B$ is a nitrogen protecting group.

As generally defined herein, $G^3$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —CH$_2OR^A$, —OC(O)$R^C$, —S$R^A$, —N($R^B$)$_2$, —N($R^B$)C(O)$R^C$, —C(O)N($R^B$)$_2$, —CN, —NO$_2$, —C(O)$R^C$, —C(O)$OR^A$, —S(O)$R^C$, —SO$_2R^A$, —SO$_2$N($R^B$)$_2$, =O, =NOH, =N—$OR^A$, =N—NH$_2$, =N—NH$R^B$, =N—N($R^B$)$_2$, and —NHSO$_2R^A$. In certain embodiments, $G^3$ is H. In certain embodiments, $G^3$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —CH$_2OR^A$, —OC(O)$R^C$, —S$R^A$, —N($R^B$)$_2$, —N($R^B$)C(O)$R^C$, —C(O)N($R^B$)$_2$, —CN, —NO$_2$, —C(O)$R^C$, —C(O)$OR^A$, —S(O)$R^C$, —SO$_2R^A$, —SO$_2$N($R^B$)$_2$, =O, =NOH, =N—$OR^A$, =N—NH$_2$, =N—NH$R^B$, =N—N($R^B$)$_2$, and —NHSO$_2R^A$. In certain embodiments, $G^3$ is halogen. In certain embodiments, $G^3$ is optionally substituted $C_1$-$C_6$ alkyl. In certain embodiments, $G^3$ is methyl, ethyl, or n-propyl. In certain embodiments, $G^7$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^3$ is —OH. In certain embodiments, $G^3$ is —$OR^A$, wherein $R^A$ is optionally substituted $C_1$-$C_6$ alkyl. In certain embodiments, $G^3$ is —OCH$_3$ or —OC$_2$H$_5$. In certain embodiments, $G^3$ is —$OR^A$, wherein $R^A$ is an oxygen protecting group. In certain embodiments, $G^3$ is —N($R^B$)$_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^3$ is NH$_2$. In certain embodiments, $G^3$ is NH$R^B$, wherein $R^B$ is optionally substituted $C_1$-$C_6$ alkyl. In certain embodiments, $G^3$ is NHCH$_3$ or NHC$_2$H$_5$. In certain embodiments, $G^3$ is NH$R^B$, wherein $R^B$ is a nitrogen protecting group.

As generally defined herein, $G^4$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —CH$_2OR^A$, —OC(O)$R^C$, —S$R^A$, —N($R^B$)$_2$, —N($R^B$)C(O)$R^C$, —C(O)N($R^B$)$_2$, —CN, —NO$_2$, —C(O)$R^C$, —C(O)$OR^A$, —S(O)$R^C$, —SO$_2R^A$, —SO$_2$N($R^B$)$_2$, =O, =NOH, =N—$OR^A$, =N—NH$_2$, =N—NH$R^B$, =N—N($R^B$)$_2$, and —NHSO$_2R^A$. In certain embodiments, $G^4$ is H. In certain embodiments, $G^4$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, =O, =NOH, =N—$OR^A$, =N—$NH_2$, =N—$NHR^B$, =N—$N(R^B)_2$, and —$NHSO_2R^A$. In certain embodiments, $G^4$ is halogen. In certain embodiments, $G^4$ is optionally substituted $C_1$-$C_6$ alkyl. In certain embodiments, $G^4$ is methyl, ethyl, or n-propyl. In certain embodiments, $G^4$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^4$ is —OH. In certain embodiments, $G^4$ is —$OR^A$, wherein $R^A$ is optionally substituted $C_1$-$C_6$ alkyl. In certain embodiments, $G^4$ is —$OCH_3$ or —$OC_2H_5$. In certain embodiments, $G^4$ is —$OR^A$, wherein $R^A$ is an oxygen protecting group. In certain embodiments, $G^4$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^4$ is $NH_2$. In certain embodiments, $G^4$ is $NHR^B$, wherein $R^B$ is optionally substituted $C_1$-$C_6$ alkyl. In certain embodiments, $G^4$ is $NHCH_3$ or $NHC_2H_5$. In certain embodiments, $G^4$ is $NHR^B$, wherein $R^B$ is a nitrogen protecting group.

In certain embodiments, $G^1$ and $G^2$ are taken together with their intervening atoms to form an optionally substituted carbocycle or heterocycle. In certain embodiments, $G^1$ and $G^2$ are taken together with their intervening atoms to form an optionally substituted carbocycle. In certain embodiments, $G^1$ and $G^2$ are taken together with their intervening atoms to form an optionally substituted 5-membered carbocycle. In certain embodiments, $G^1$ and $G^2$ are taken together with their intervening atoms to form an optionally substituted 6-membered carbocycle. In certain embodiments, $G^1$ and $G^2$ are taken together with their intervening atoms to form an optionally substituted phenyl. In certain embodiments, $G^1$ and $G^2$ are taken together with their intervening atoms to form an unsubstituted phenyl. In certain embodiments, $G^1$ and $G^2$ are taken together with their intervening atoms to form an optionally substituted heterocycle. In certain embodiments, $G^1$ and $G^2$ are taken together with their intervening atoms to form an optionally substituted 5-membered heterocycle with one heteroatom of S, N, or O. In certain embodiments, $G^1$ and $G^2$ are taken together with their intervening atoms to form an optionally substituted 5-membered heterocycle with two heteroatom each independently selected from the group of S, N, and O. In certain embodiments, $G^1$ and $G^2$ are taken together with their intervening atoms to form an optionally substituted 6-membered carbocycle with one heteroatom of S, N, or O. In certain embodiments, $G^1$ and $G^2$ are taken together with their intervening atoms to form an optionally substituted 6-membered carbocycle with two heteroatoms each independently selected from the group consisting of S, N, and O.

In certain embodiments, $G^3$ and $G^4$ are taken together with their intervening atoms to form an optionally substituted carbocycle or heterocycle. In certain embodiments, $G^3$ and $G^4$ are taken together with their intervening atoms to form an optionally substituted carbocycle. In certain embodiments, $G^3$ and $G^4$ are taken together with their intervening atoms to form an optionally substituted cyclopropyl. In certain embodiments, $G^3$ and $G^4$ are taken together with their intervening atoms to form an optionally substituted 4-membered carbocycle. In certain embodiments, $G^3$ and $G^4$ are taken together with their intervening atoms to form an optionally substituted 5-membered carbocycle. In certain embodiments, $G^3$ and $G^4$ are taken together with their intervening atoms to form an optionally substituted 6-membered carbocycle. In certain embodiments, $G^3$ and $G^4$ are taken together with their intervening atoms to form an optionally substituted heterocycle. In certain embodiments, $G^3$ and $G^4$ are taken together with their intervening atoms to form an optionally substituted 5-membered heterocycle with one heteroatom of S, N, or O. In certain embodiments, $G^3$ and $G^4$ are taken together with their intervening atoms to form an optionally substituted 5-membered heterocycle with two heteroatom each independently selected from the group of S, N, and O. In certain embodiments, $G^3$ and $G^4$ are taken together with their intervening atoms to form an optionally substituted 6-membered carbocycle with one heteroatom of S, N, or O. In certain embodiments, $G^3$ and $G^4$ are taken together with their intervening atoms to form an optionally substituted 6-membered carbocycle with two heteroatoms each independently selected from the group consisting of S, N, and O.

As generally defined herein, $G^5$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^5$ is H. In certain embodiments, $G^5$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^5$ is halogen. In certain embodiments, $G^5$ is optionally substituted $C_1$-$C_6$ alkyl. In certain embodiments, $G^5$ is methyl, ethyl, or n-propyl. In certain embodiments, $G^5$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^5$ is —OH. In certain embodiments, $G^5$ is —$OR^A$, wherein $R^A$ is optionally substituted $C_1$-$C_6$ alkyl. In certain embodiments, $G^5$ is —$OCH_3$ or —$OC_2H_5$. In certain embodiments, $G^5$ is —$OR^A$, wherein $R^A$ is an oxygen protecting group. In certain embodiments, $G^5$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^5$ is $NH_2$. In certain embodiments, $G^5$ is $NHR^B$, wherein $R^B$ is optionally substituted $C_1$-$C_6$ alkyl. In certain embodiments, $G^5$ is $NHCH_3$ or $NHC_2H_5$. In certain embodiments, $G^5$ is $NHR^B$, wherein $R^B$ is a nitrogen protecting group.

As generally defined herein, $G^8$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^8$ is H. In certain embodiments, $G^8$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^8$ is halogen. In certain embodiments, $G^8$ is optionally substituted $C_1$-$C_6$ alkyl. In certain embodiments, $G^8$ is methyl, ethyl, or n-propyl. In certain embodiments, $G^8$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attaching to an oxygen, or a sulfur protecting group when attaching to sulfur. In certain embodiments, $G^8$ is —OH. In certain embodiments, $G^8$ is —$OR^A$, wherein $R^A$ is optionally substituted $C_1$-$C_6$ alkyl. In certain embodiments, $G^8$ is —$OCH_3$ or —$OC_2H_5$. In certain embodiments, $G^8$ is —$OR^A$, wherein $R^A$ is an oxygen protecting group. In certain embodiments, $G^8$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^8$ is $NH_2$. In certain embodiments, $G^8$ is $NHR^B$, wherein $R^B$ is optionally substituted $C_1$-$C_6$ alkyl. In certain embodiments, $G^8$ is $NHCH_3$ or $NHC_2H_5$. In certain embodiments, $G^8$ is $NHR^B$, wherein $R^B$ is a nitrogen protecting group.

As generally defined herein, $G^6$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^6$ is H. In certain embodiments, $G^6$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^6$ is halogen. In certain embodiments, $G^6$ is optionally substituted $C_1$-$C_6$ alkyl. In certain embodiments, $G^6$ is methyl, ethyl, or n-propyl. In certain embodiments, $G^6$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^6$ is —OH. In certain embodiments, $G^6$ is —$OR^A$, wherein $R^A$ is optionally substituted $C_1$-$C_6$ alkyl. In certain embodiments, $G^6$ is —$OCH_3$ or —$OC_2H_5$. In certain embodiments, $G^6$ is —$OR^A$, wherein $R^A$ is an oxygen protecting group. In certain embodiments, $G^6$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^6$ is $NH_2$. In certain embodiments, $G^6$ is $NHR^B$, wherein $R^B$ is optionally substituted $C_1$-$C_6$ alkyl. In certain embodiments, $G^6$ is $NHCH_3$ or $NHC_2H_5$. In certain embodiments, $G^6$ is $NHR^B$, wherein $R^B$ is a nitrogen protecting group.

As generally defined herein, $G^7$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^7$ is H. In certain embodiments, $G^7$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^7$ is halogen. In certain embodiments, $G^7$ is optionally substituted $C_1$-$C_6$ alkyl. In certain embodiments, $G^7$ is methyl, ethyl, or n-propyl. In certain embodiments, $G^7$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^7$ is —OH. In certain embodiments, $G^7$ is —$OR^A$, wherein $R^A$ is optionally substituted $C_1$-$C_6$ alkyl. In certain embodiments, $G^7$ is —$OCH_3$ or —$OC_2H_5$. In certain embodiments, $G^7$ is —$OR^A$, wherein $R^A$ is an oxygen protecting group. In certain embodiments, $G^7$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^7$ is $NH_2$. In certain embodiments, $G^7$ is $NHR^B$, wherein $R^B$ is optionally substituted $C_1$-$C_6$ alkyl. In certain embodiments, $G^7$ is $NHCH_3$ or $NHC_2H_5$. In certain embodiments, $G^7$ is $NHR^B$, wherein $R^B$ is a nitrogen protecting group.

In certain embodiments, $G^6$ and $G^7$ are taken together with their intervening atoms to form an optionally substituted carbocycle or heterocycle. In certain embodiments, $G^6$ and $G^7$ are taken together with their intervening atoms to form an optionally substituted carbocycle. In certain embodiments, $G^6$ and $G^7$ are taken together with their intervening atoms to form an optionally substituted 5-membered carbocycle. In certain embodiments, $G^6$ and $G^7$ are taken together with their intervening atoms to form an optionally substituted 6-membered carbocycle. In certain embodiments, $G^6$ and $G^7$ are taken together with their intervening atoms to form an optionally substituted heterocycle. In certain embodiments, $G^6$ and $G^7$ are taken together with their intervening atoms to form an optionally substituted 5-membered heterocycle with one heteroatom of S, N, or O. In certain embodiments, $G^6$ and $G^7$ are taken together with their intervening atoms to form an optionally substituted 5-membered heterocycle with two heteroatom each independently selected from the group of S, N, and O. In certain embodiments, $G^6$ and $G^7$ are taken together with their intervening atoms to form an optionally substituted 6-membered carbocycle with one heteroatom of S, N, or O. In certain embodiments, $G^6$ and $G^7$ are taken together with their intervening atoms to form an optionally substituted 6-membered carbocycle with two heteroatoms each independently selected from the group consisting of S, N, and O.

In certain embodiments, the compounds described herein are of formula (II)

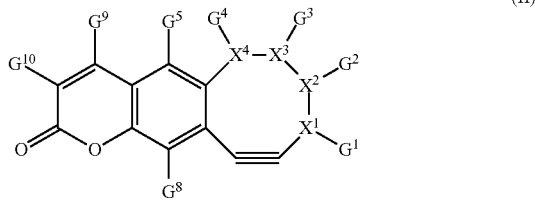

(II)

or a salt thereof,
wherein
each of $G^9$ and $G^{10}$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$.

As generally defined herein, $G^9$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^9$ is H. In certain embodiments, $G^9$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^9$ is halogen. In certain embodiments, $G^9$ is optionally substituted $C_1$-$C_6$ alkyl. In certain embodiments, $G^9$ is methyl, ethyl, or n-propyl. In certain embodiments, $G^9$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^9$ is —OH. In certain embodiments, $G^9$ is —$OR^A$, wherein $R^A$ is optionally substituted $C_1$-$C_6$ alkyl. In certain embodiments, $G^9$ is —$OCH_3$ or —$OC_2H_5$. In certain embodiments, $G^9$ is —$OR^A$, wherein $R^A$ is an oxygen protecting group. In certain embodiments, $G^9$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^9$ is $NH_2$. In certain embodiments, $G^9$ is $NHR^B$, wherein $R^B$ is optionally substituted $C_1$-$C_6$ alkyl. In certain embodiments, $G^9$ is $NHCH_3$ or $NHC_2H_5$. In certain embodiments, $G^9$ is $NHR^B$, wherein $R^B$ is a nitrogen protecting group.

As generally defined herein, $G^{10}$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^{10}$ is H. In certain embodiments, $G^{10}$ is halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$. In certain embodiments, $G^{10}$ is halogen. In certain embodiments, $G^{10}$ is optionally substituted $C_1$-$C_6$ alkyl. In certain embodiments, $G^{10}$ is methyl, ethyl, or n-propyl. In certain embodiments, $G^{10}$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^{10}$ is —OH. In certain embodiments, $G^{10}$ is —$OR^A$, wherein $R^A$ is optionally substituted $C_1$-$C_6$ alkyl. In certain embodiments, $G^{10}$ is —$OCH_3$ or —$OC_2H_5$. In certain embodiments, $G^{10}$ is —$OR^A$, wherein $R^A$ is an oxygen protecting group. In certain embodiments, $G^{10}$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^{10}$ is $NH_2$. In certain embodiments, $G^{10}$ is $NHR^B$, wherein $R^B$ is optionally substituted $C_1$-$C_6$ alkyl. In certain embodiments, $G^{10}$ is $NHCH_3$ or $NHC_2H_5$. In certain embodiments, $G^{10}$ is $NHR^B$, wherein $R^B$ is a nitrogen protecting group. In certain embodiments, $G^{10}$ is —$C(O)R^C$, wherein $R^C$ is hydrogen or optionally substituted $C_{1-6}$ alkyl. In certain embodiments, $G^{10}$ is —C(O)H. In certain embodiments, $G^{10}$ is —$C(O)R^C$, wherein $R^C$ is optionally $C_{1-6}$ substituted alkyl. In certain embodiments, $G^{10}$ is optionally substituted alkenyl. In certain embodiments, $G^{10}$ is of the formula

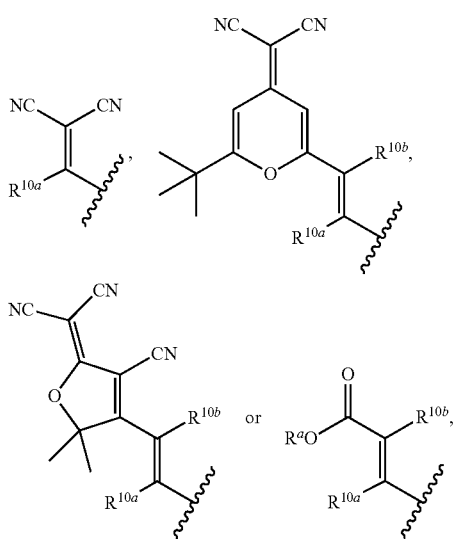

wherein $R^A$ is as defined herein; and each instance of $R^{10a}$ and $R^{10b}$ is independently hydrogen, halogen, or optionally substituted $C_{1-6}$ alkyl.

As generally defined herein, each instance of $R^{10a}$ and $R^{10b}$ is independently hydrogen, halogen, or optionally substituted $C_{1-6}$ alkyl. In certain embodiments, $R^{10a}$ is hydrogen. In certain embodiments, $R^{10a}$ is halogen. In certain embodiments, $R^{10b}$ is hydrogen. In certain embodiments, $R^{10b}$ is halogen. In certain embodiments, $G^{10}$ is one of the following formulae:

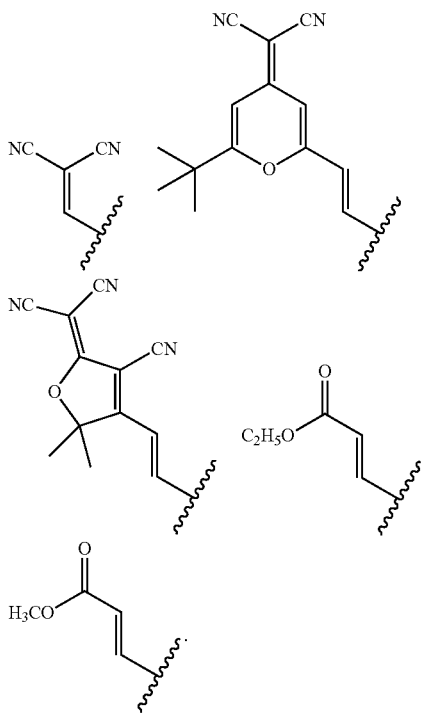

As generally defined herein, each instance of $R^A$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or an oxygen protecting group when attached to an oxygen, or a sulfur protecting group when attaching to sulfur. In certain embodiments, $R^A$ is hydrogen. In certain embodiments, $R^A$ is optionally substituted $C_1$-$C_6$ alkyl. In certain embodiments, $R^A$ is methyl or ethyl. In certain embodiments, $R^A$ is an oxygen protecting group. In certain embodiments, $R^A$ is a sulfur protecting group.

As generally defined herein, each instance of $R^B$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or a nitrogen protecting group, or two $R^B$ taken together with the intervening nitrogen form a heterocycle. In certain embodiments, $R^B$ is hydrogen. In certain embodiments, $R^B$ is optionally substituted $C_1$-$C_6$ alkyl. In certain embodiments, $R^B$ is methyl or ethyl. In certain embodiments, $R^B$ is a nitrogen protecting group. In certain embodiments, two $R^B$ are taken together with the intervening nitrogen form a heterocycle.

As generally defined herein, each instance of $R^C$ is independently hydrogen, optionally substituted $C_1$-$C_6$ alkyl, optionally substituted alkenyl, optionally substituted alkynyl, optionally substituted heterocyclyl, optionally substituted aryl, or optionally substituted heteroaryl. In certain embodiments, $R^C$ is hydrogen. In certain embodiments, $R^C$ is optionally substituted $C_1$-$C_6$ alkyl. In certain embodiments, $R^C$ is methyl or ethyl. In certain embodiments, $R^C$ is a nitrogen protecting group. In certain embodiments, two $R^C$ are taken together with the intervening nitrogen form a heterocycle.

In certain embodiments of formulae (I) and (II), $X^1$—$X^2$ is —CH=CH—. In certain embodiments of formula (I), $X^3$—$X^4$ is —CH=CH—.

In certain embodiments of formula (II), $G^9$ is hydrogen and $G^{10}$ is optionally substituted alkenyl. In certain embodiments, $G^{10}$ is of Formula (G-i).

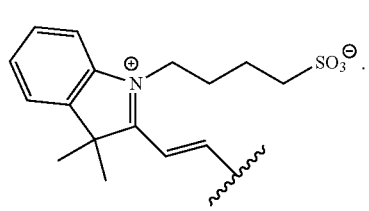

(G-i)

In certain embodiments, the provided compounds are of one of following formulae:

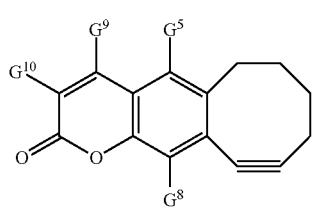

(II-a)

-continued (II-b)
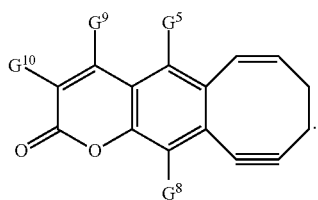

(II-c)
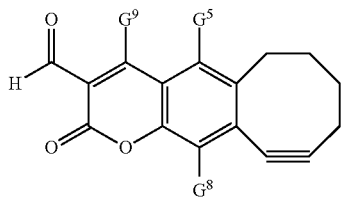

(II-d)
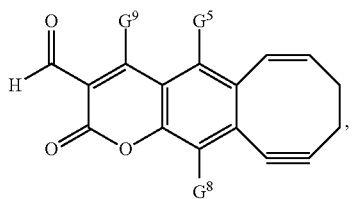

(II-e)
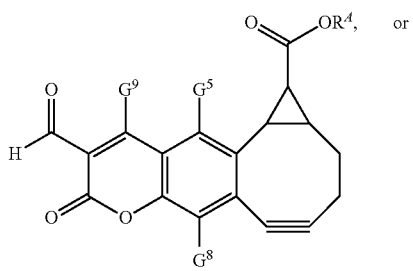

(II-f)
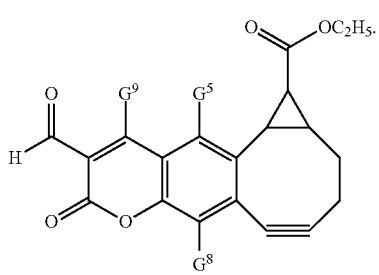

In certain embodiments of formulae (II-a) to (II-f), $G^5$ is hydrogen. In certain embodiments of formulae (II-a) to (II-f), $G^8$ is hydrogen. In certain embodiments of formulae (II-a) to (II-f), $G^9$ is hydrogen. In certain embodiments of formulae (II-a) to (II-f), $G^5$, $G^8$, and $G^9$ are all hydrogen. In certain embodiments of formula (II-e), $R^A$ is hydrogen or optionally substituted $C_{1-6}$ alkyl. In certain embodiments of formula (II-e), $R^A$ is hydrogen. In certain embodiments of formula (II-e), $R^A$ is methyl or ethyl.

In certain embodiments of formula (II-a) and (II-b), $G^{10}$ is of the formula:

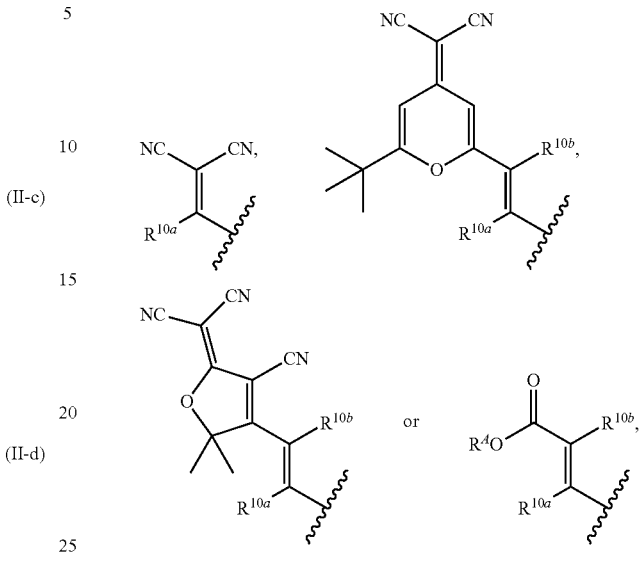

wherein $R^A$ is as defined herein; and each instance of $R^{10a}$ and $R^{10b}$ is independently hydrogen, halogen, or optionally substituted $C_{1-6}$ alkyl. In certain embodiments of formula (II-a) and (II-b), $G^{10}$ is of one of following the formulae:

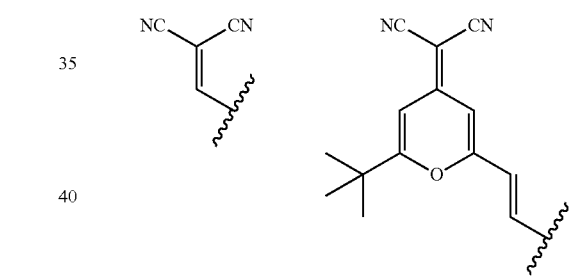

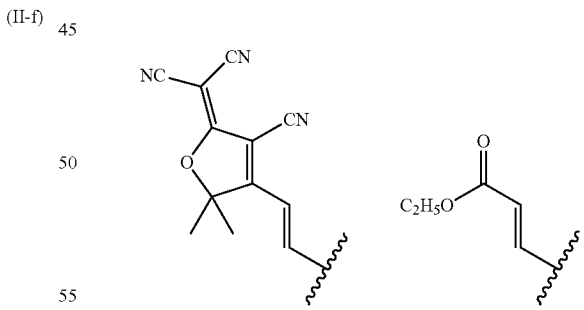

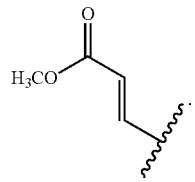

Exemplary compounds of formulae (I) and (II) are shown in Table 1:

TABLE 1
Exemplary compounds of formulae (I) and (II).
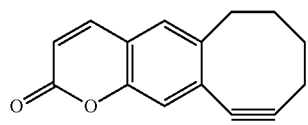 [SMILES: O=c1ccc2cc3c(cc2o1)C#CCCCC3] (1)
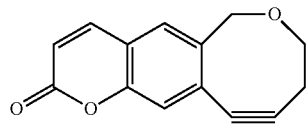 (T2)
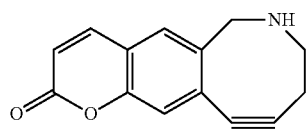 [SMILES: O=c1ccc2cc3c(cc2o1)C#CCCNC3] (T3)
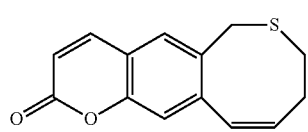 (T4)
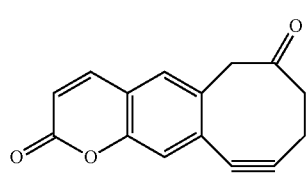 [SMILES: O=C1CCC#Cc2cc3oc(=O)ccc3cc2C1] (T5)
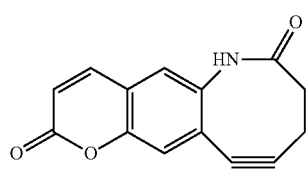 [SMILES: O=C1CCC#Cc2cc3oc(=O)ccc3cc2N1] (T6)
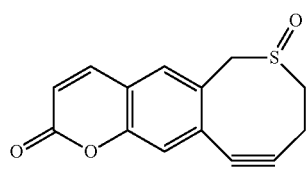 [SMILES: O=c1ccc2cc3c(cc2o1)C#CCCS(=O)C3] (T7)
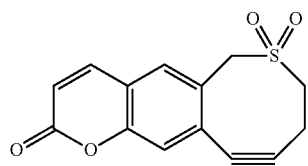 [SMILES: O=c1ccc2cc3c(cc2o1)C#CCCS(=O)(=O)C3] (T8)
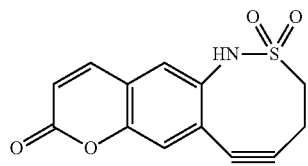 [SMILES: O=c1ccc2cc3c(cc2o1)C#CCCS(=O)(=O)N3] (T9)
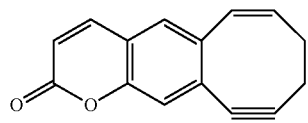 (T10)

TABLE 1-continued
Exemplary compounds of formulae (I) and (II).
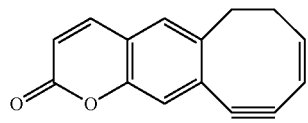 [SMILES: O=c1ccc2cc3c(cc2o1)C#C/C=C\CC3] (T11)
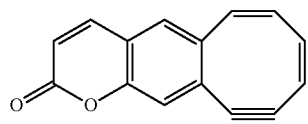 [SMILES: O=c1ccc2cc3c(cc2o1)C#C/C=C\C=C/3] (T12)
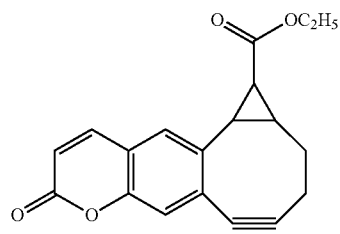 [SMILES: CCOC(=O)C1C2CCC#Cc3cc4oc(=O)ccc4cc3C21] (T13)
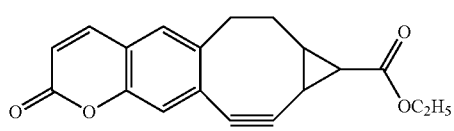 [SMILES: CCOC(=O)C1C2C#Cc3cc4oc(=O)ccc4cc3CCC21] (T14)
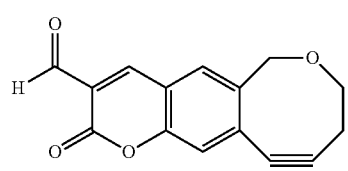 (T15)
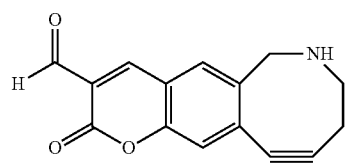 [SMILES: O=Cc1cc2cc3c(cc2oc1=O)C#CCCNC3] (T16)
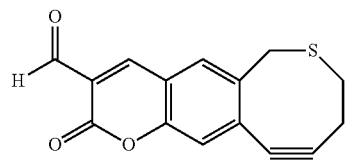 (T17)
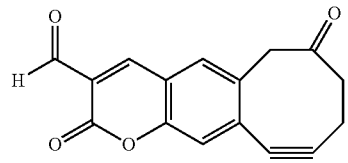 [SMILES: O=Cc1cc2cc3c(cc2oc1=O)C#CCCC(=O)C3] (T18)
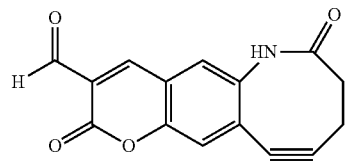 [SMILES: O=Cc1cc2cc3c(cc2oc1=O)C#CCCC(=O)N3] (T19)

TABLE 1-continued
Exemplary compounds of formulae (I) and (II).
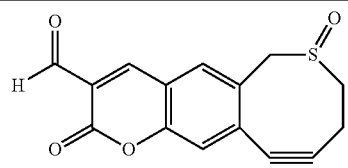 (T20)
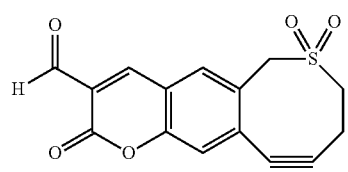 [SMILES: O=Cc1cc2cc3c(cc2oc1=O)C#CCCS(=O)(=O)C3] (T21)
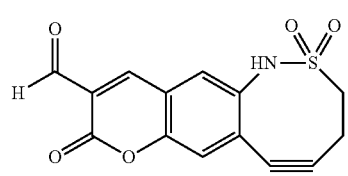 [SMILES: O=Cc1cc2cc3c(cc2oc1=O)C#CCCS(=O)(=O)N3] (T22)
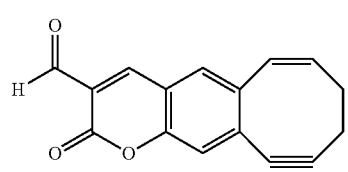 [SMILES: O=Cc1cc2cc3c(cc2oc1=O)C#CCC/C=C\3] (T23)
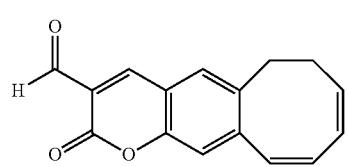 (T24)
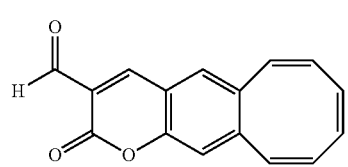 (T25)
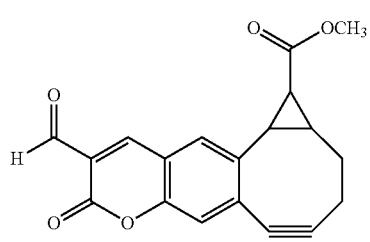 [SMILES: COC(=O)C1C2CCC#Cc3cc4oc(=O)c(C=O)cc4cc3C21] (T26)
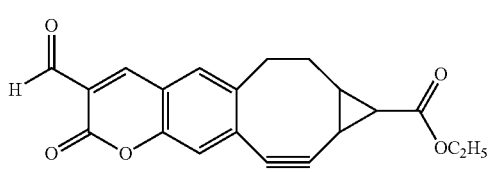 [SMILES: CCOC(=O)C1C2C#Cc3cc4oc(=O)c(C=O)cc4cc3CCC21] (T27)
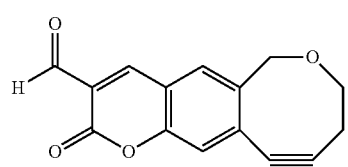 [SMILES: O=Cc1cc2cc3c(cc2oc1=O)C#CCCOC3] (T28)

TABLE 1-continued
Exemplary compounds of formulae (I) and (II).
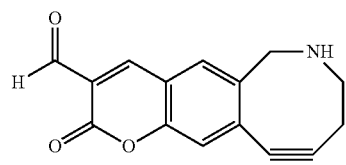 [SMILES: O=Cc1cc2cc3c(cc2oc1=O)C#CCCNC3] (T29)
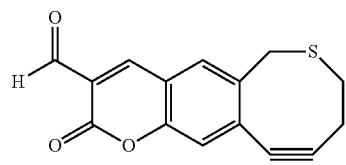 (T30)
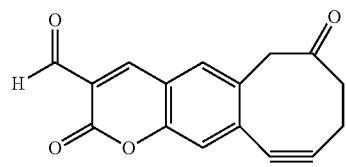 (T31)
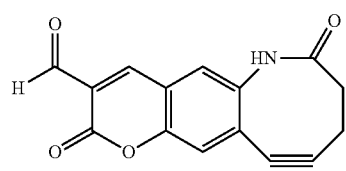 [SMILES: O=Cc1cc2cc3c(cc2oc1=O)C#CCCC(=O)N3] (T32)
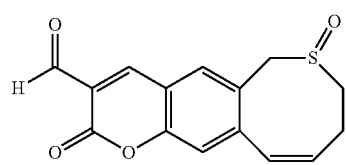 (T33)
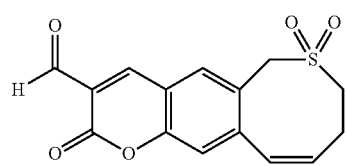 (T34)
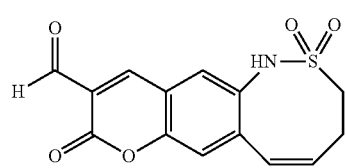 (T35)
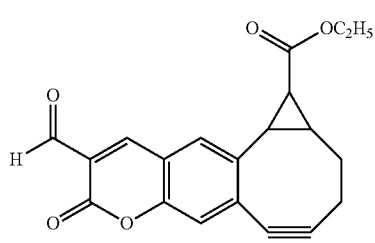 [SMILES: CCOC(=O)C1C2CCC#Cc3cc4oc(=O)c(C=O)cc4cc3C21] (T36)

TABLE 1-continued
Exemplary compounds of formulae (I) and (II).
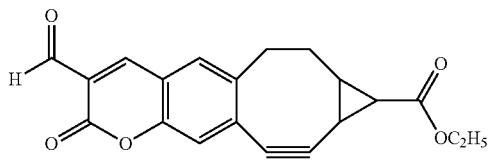 [SMILES: CCOC(=O)C1C2C#Cc3cc4oc(=O)c(C=O)cc4cc3CCC21]
(T37)
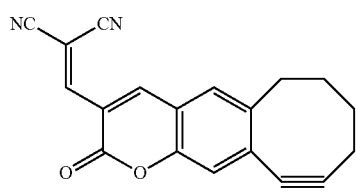 [SMILES: N#CC(C#N)=Cc1cc2cc3c(cc2oc1=O)C#CCCCC3]
(T38)
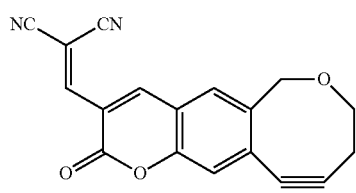 [SMILES: N#CC(C#N)=Cc1cc2cc3c(cc2oc1=O)C#CCCOC3]
(T39)
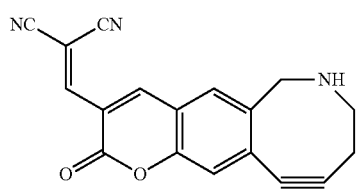
(T40)
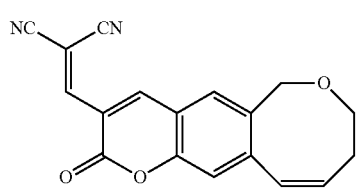
(T41)
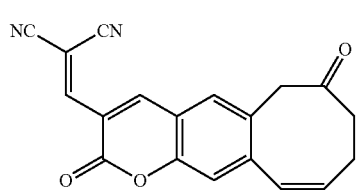
(T42)
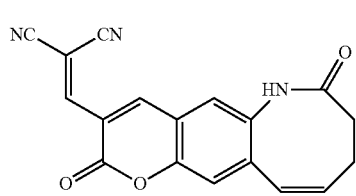
(T43)
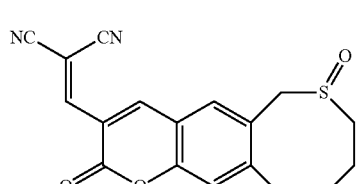
(T44)

TABLE 1-continued
Exemplary compounds of formulae (I) and (II).
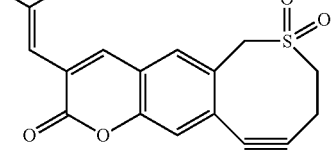 (T45)
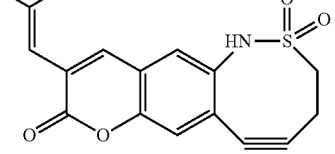 (T46)
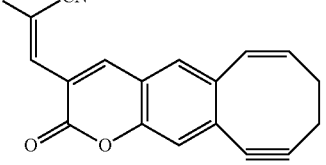 (T47)
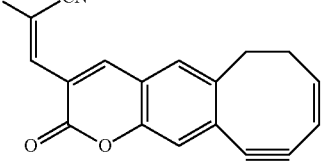 (T48)
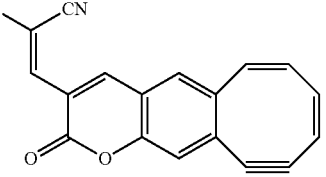 (T49)
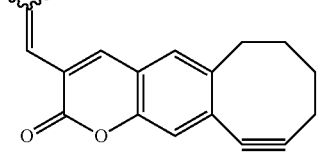 (T50)
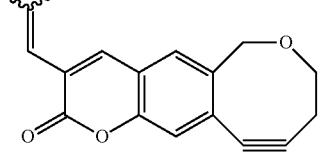 (T51)
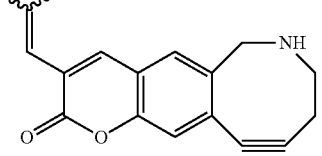 (T52)

TABLE 1-continued
Exemplary compounds of formulae (I) and (II).
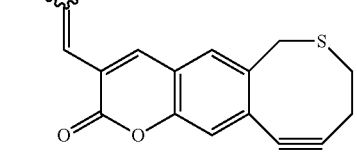
(T53)
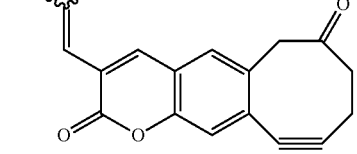
(T54)
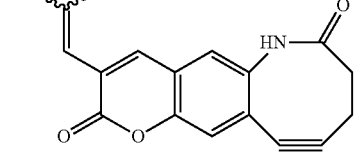
(T55)
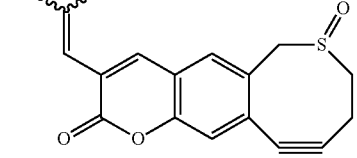
(T56)
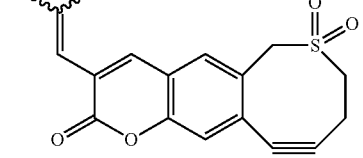
(T57)
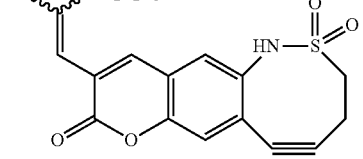
(T58)
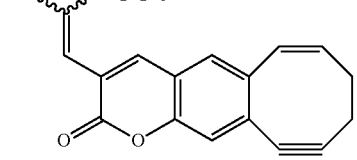
(T59)
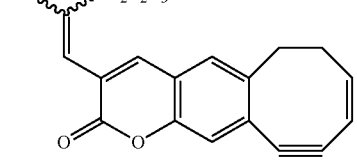
(T60)

TABLE 1-continued
Exemplary compounds of formulae (I) and (II).
 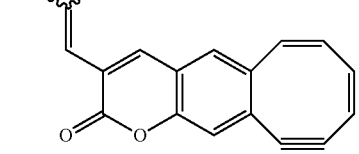 (T61)
 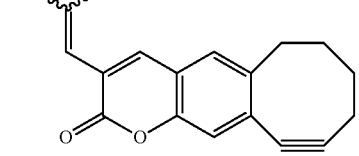 (T62)
 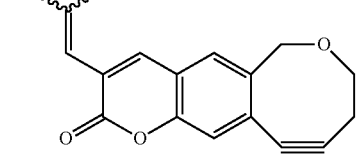 (T63)
 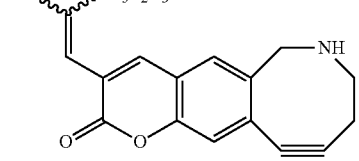 (T64)
 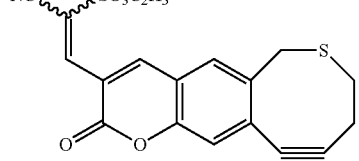 (T65)
 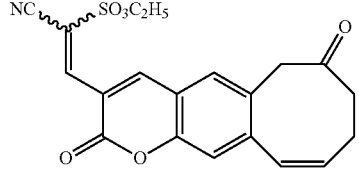 (T66)
 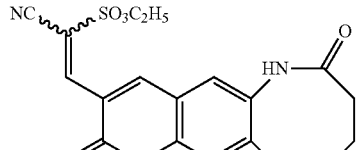 (T67)
 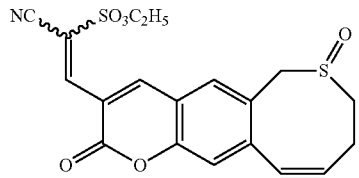 (T68)

US 9,547,009 B2
TABLE 1-continued
Exemplary compounds of formulae (I) and (II).
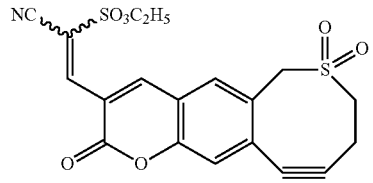 (T69)
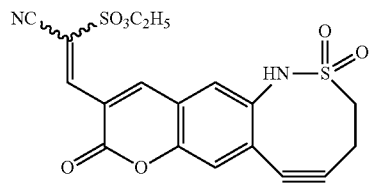 (T70)
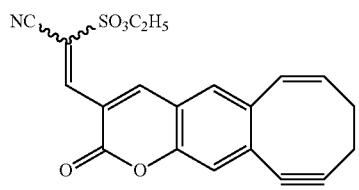 (T71)
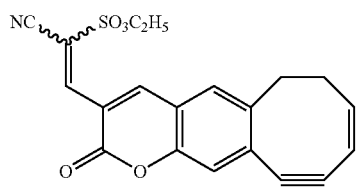 (T72)
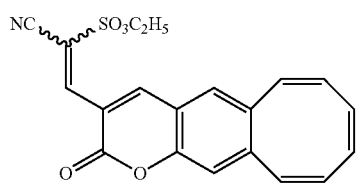 (T73)
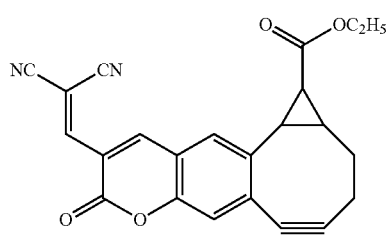 [SMILES: CCOC(=O)C1C2CCC#Cc3cc4oc(=O)c(C=C(C#N)C#N)cc4cc3C21] (T74)
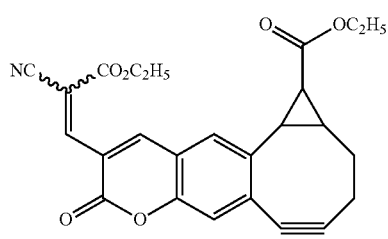 (T75)

TABLE 1-continued
Exemplary compounds of formulae (I) and (II).
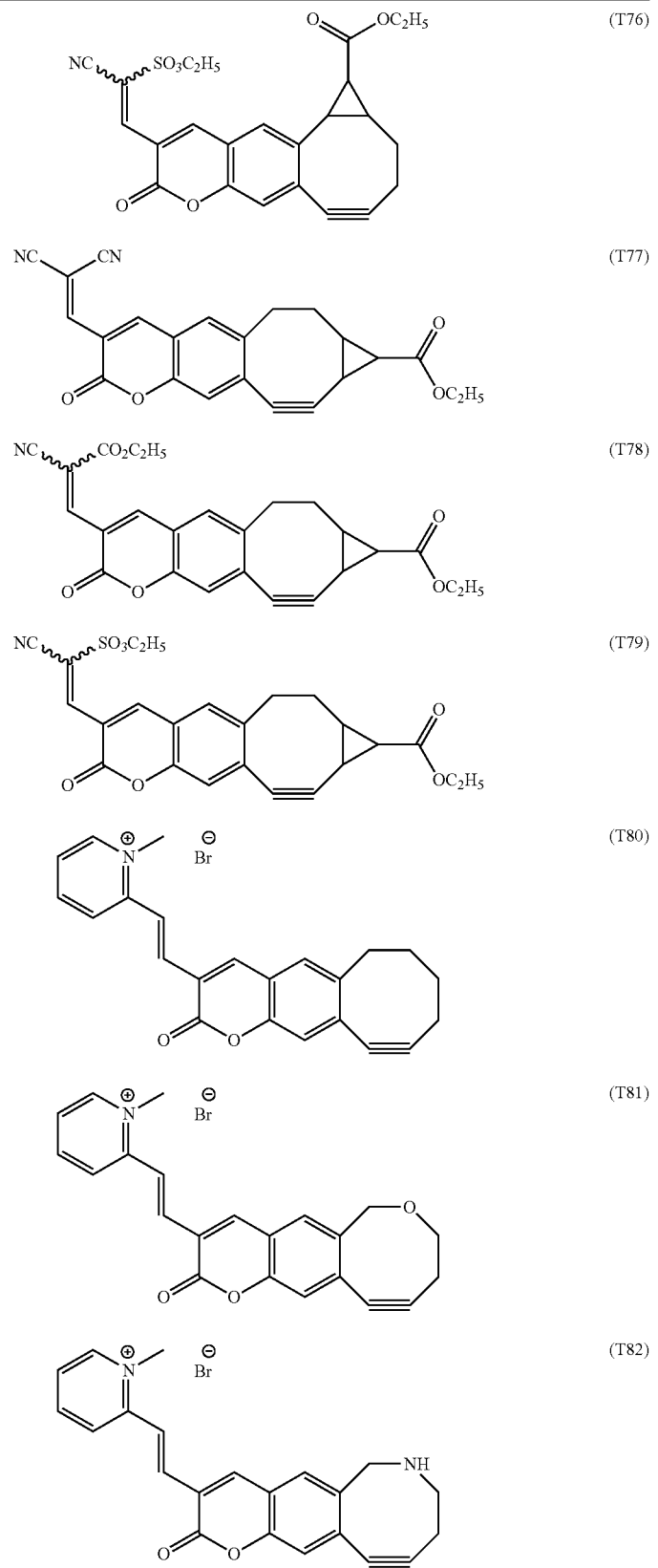
(T76)
(T77)
(T78)
(T79)
(T80)
(T81)
(T82)

TABLE 1-continued
Exemplary compounds of formulae (I) and (II).
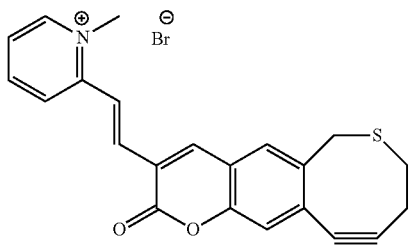 [SMILES: C[n+]1ccccc1/C=C/c1cc2cc3c(cc2oc1=O)C#CCCOC3 ; [Br-]]
(T83)
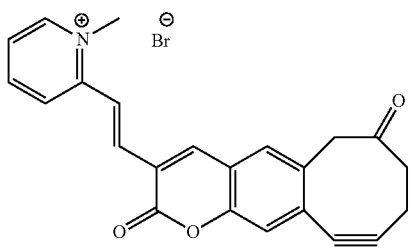 [SMILES: C[n+]1ccccc1/C=C/c1cc2cc3c(cc2oc1=O)C#CCCC(=O)C3 ; [Br-]]
(T84)
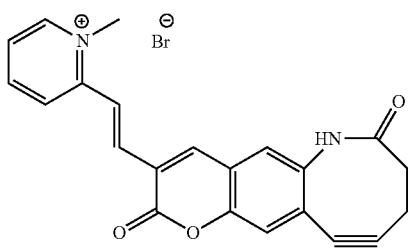 [SMILES: C[n+]1ccccc1/C=C/c1cc2cc3c(cc2oc1=O)C#CCCC(=O)N3 ; [Br-]]
(T85)
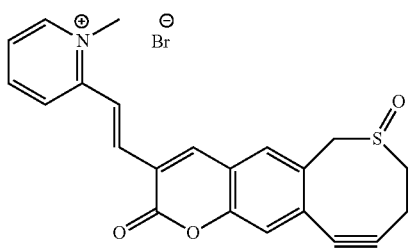 [SMILES: C[n+]1ccccc1/C=C/c1cc2cc3c(cc2oc1=O)C#CCCS(=O)C3 ; [Br-]]
(T86)
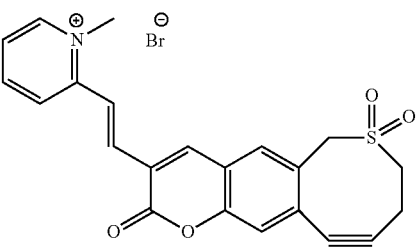 [SMILES: C[n+]1ccccc1/C=C/c1cc2cc3c(cc2oc1=O)C#CCCS(=O)(=O)C3 ; [Br-]]
(T87)
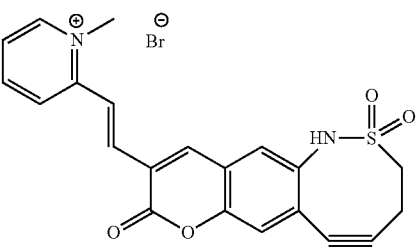 [SMILES: C[n+]1ccccc1/C=C/c1cc2cc3c(cc2oc1=O)C#CCCS(=O)(=O)N3 ; [Br-]]
(T88)

TABLE 1-continued
Exemplary compounds of formulae (I) and (II).
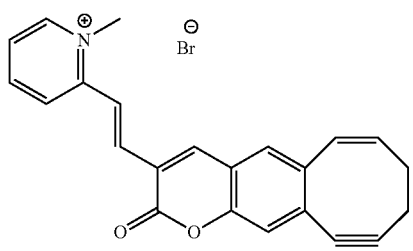 [SMILES: C[n+]1ccccc1/C=C/c1cc2cc3c(cc2oc1=O)C#CCC/C=C\3 ; [Br-]] (T89)
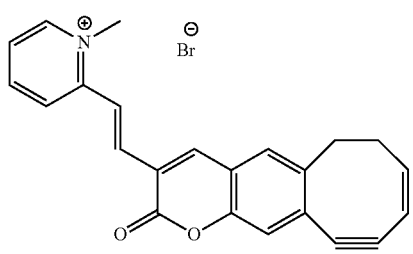 [SMILES: C[n+]1ccccc1/C=C/c1cc2cc3c(cc2oc1=O)C#C/C=C\CC3 ; [Br-]] (T90)
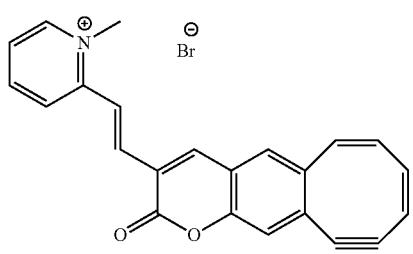 [SMILES: C[n+]1ccccc1/C=C/c1cc2cc3c(cc2oc1=O)C#C/C=C\C=C/3 ; [Br-]] (T91)
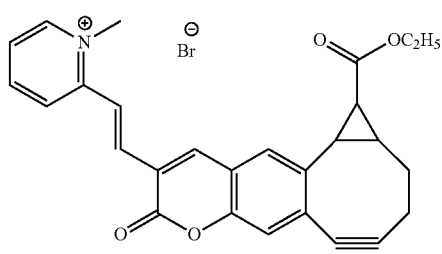 [SMILES: CCOC(=O)C1C2CCC#Cc3cc4oc(=O)c(/C=C/c5cccc[n+]5C)cc4cc3C21 ; [Br-]] (T92)
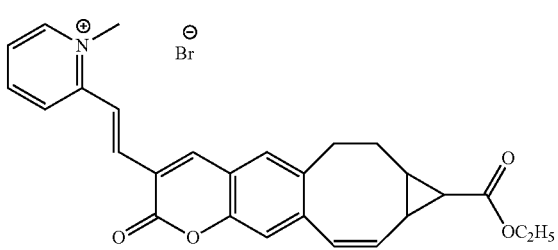 (T93)
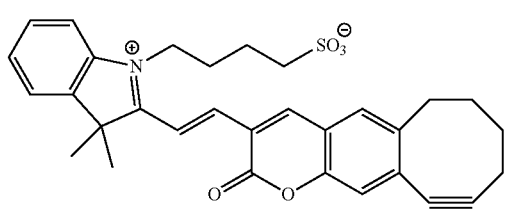 (2)

TABLE 1-continued
Exemplary compounds of formulae (I) and (II).
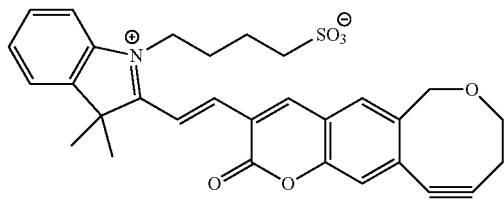 (T95)
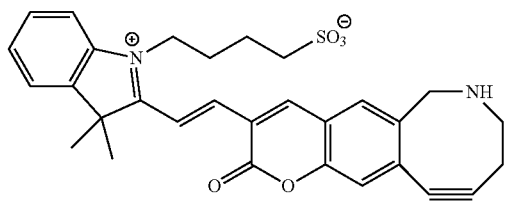 (T96)
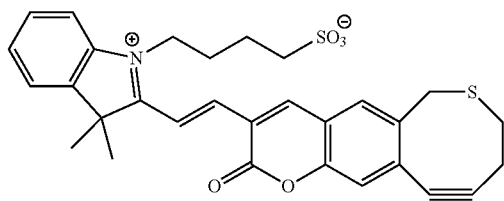 (T97)
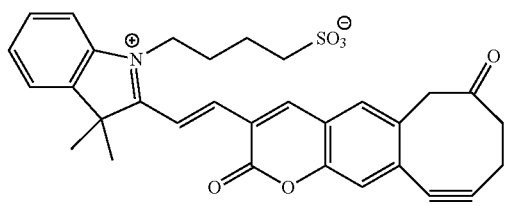 (T98)
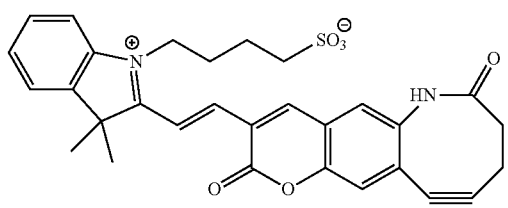 (T99)
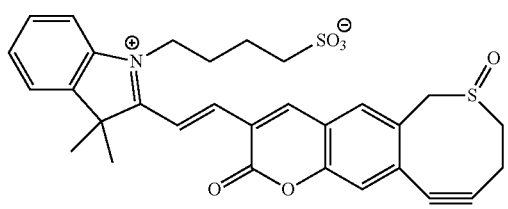 (T100)
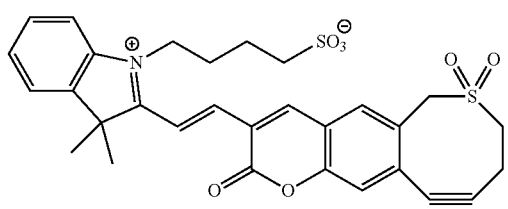 (T101)

TABLE 1-continued
Exemplary compounds of formulae (I) and (II).
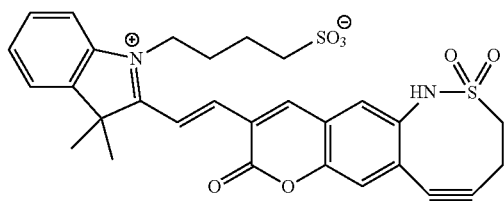 (T102)
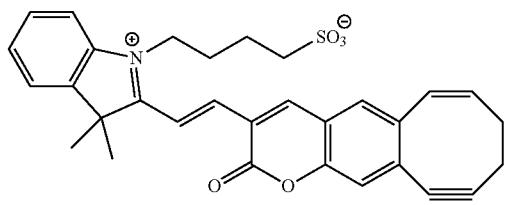 (T103)
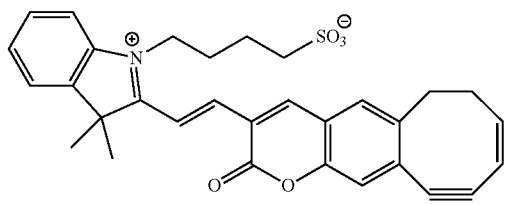 (T104)
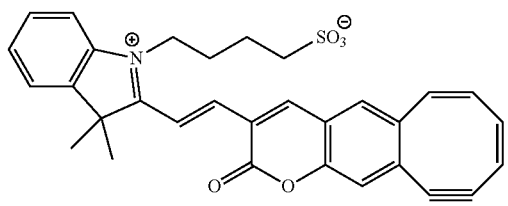 (T105)
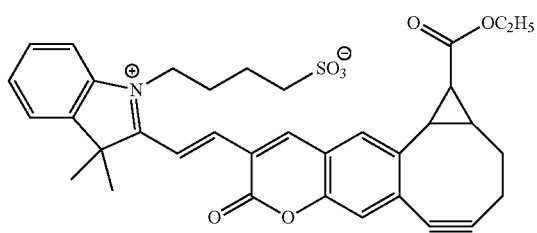 (T106)
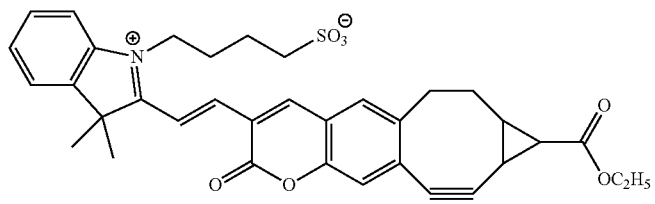 (T107)
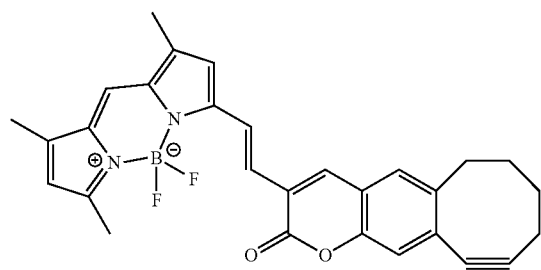 [SMILES: CC1=CC(C)=[N+]2C1=Cc1c(C)cc(/C=C/c3cc4cc5c(cc4oc3=O)C#CCCCC5)n1[B-]2(F)F] (T108)

TABLE 1-continued
Exemplary compounds of formulae (I) and (II).
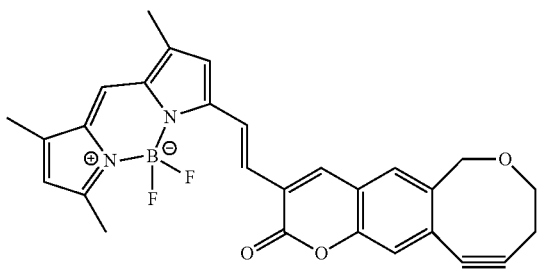 [SMILES: CC1=CC(C)=[N+]2C1=Cc1c(C)cc(/C=C/c3cc4cc5c(cc4oc3=O)C#CCCOC5)n1[B-]2(F)F]
(T109)
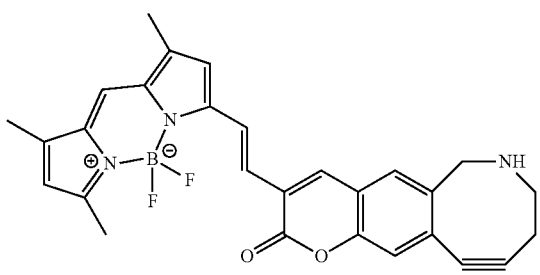 [SMILES: CC1=CC(C)=[N+]2C1=Cc1c(C)cc(/C=C/c3cc4cc5c(cc4oc3=O)C#CCCNC5)n1[B-]2(F)F]
(T110)
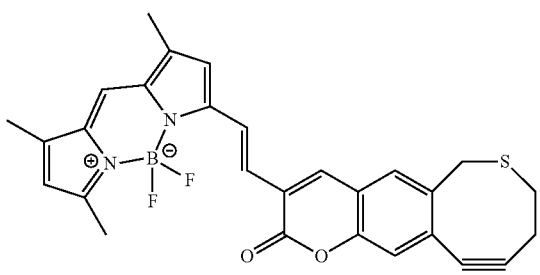
(T111)
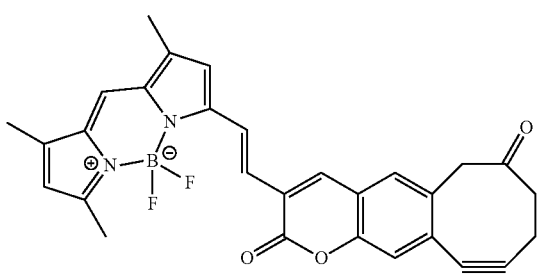 [SMILES: CC1=CC(C)=[N+]2C1=Cc1c(C)cc(/C=C/c3cc4cc5c(cc4oc3=O)C#CCCC(=O)C5)n1[B-]2(F)F]
(T112)
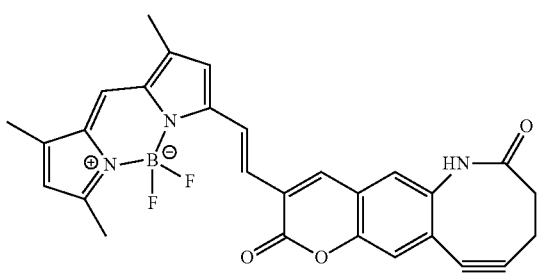 [SMILES: CC1=CC(C)=[N+]2C1=Cc1c(C)cc(/C=C/c3cc4cc5c(cc4oc3=O)C#CCCC(=O)N5)n1[B-]2(F)F]
(T113)

TABLE 1-continued
Exemplary compounds of formulae (I) and (II).
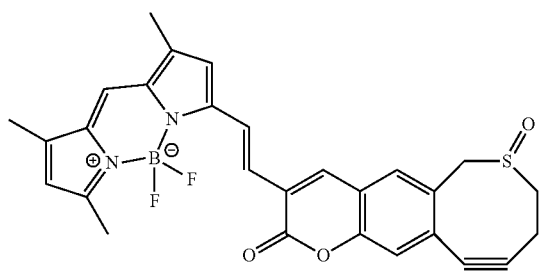 [SMILES: CC1=CC(C)=[N+]2C1=Cc1c(C)cc(/C=C/c3cc4cc5c(cc4oc3=O)C#CCCS(=O)C5)n1[B-]2(F)F]
(T114)
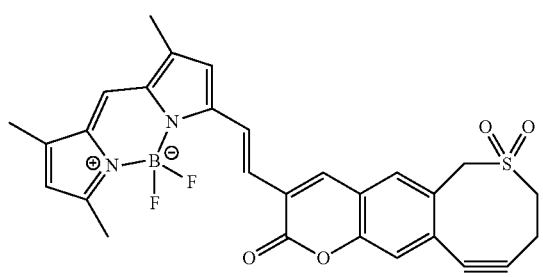 [SMILES: CC1=CC(C)=[N+]2C1=Cc1c(C)cc(/C=C/c3cc4cc5c(cc4oc3=O)C#CCCS(=O)(=O)C5)n1[B-]2(F)F]
(T115)
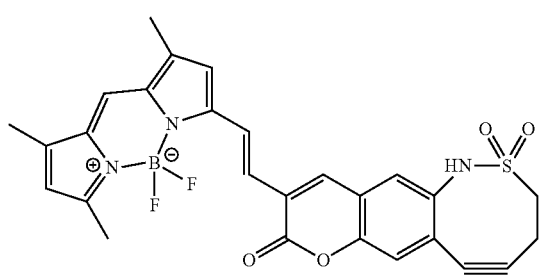 [SMILES: CC1=CC(C)=[N+]2C1=Cc1c(C)cc(/C=C/c3cc4cc5c(cc4oc3=O)C#CCCS(=O)(=O)N5)n1[B-]2(F)F]
(T116)
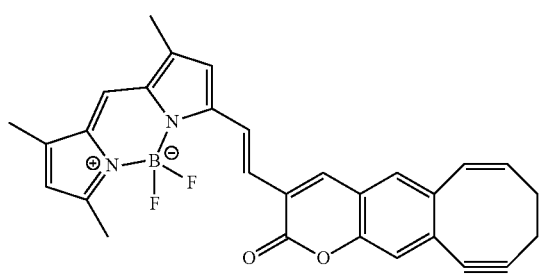 [SMILES: CC1=CC(C)=[N+]2C1=Cc1c(C)cc(/C=C/c3cc4cc5c(cc4oc3=O)C#CCC/C=C\5)n1[B-]2(F)F]
(T117)
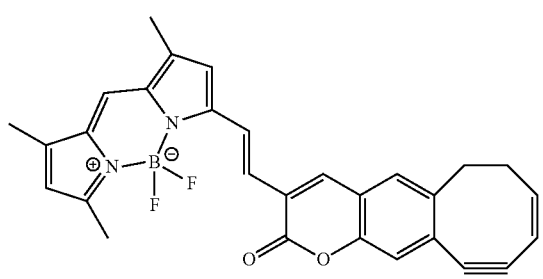 [SMILES: CC1=CC(C)=[N+]2C1=Cc1c(C)cc(/C=C/c3cc4cc5c(cc4oc3=O)C#C/C=C\CC5)n1[B-]2(F)F]
(T118)

TABLE 1-continued
Exemplary compounds of formulae (I) and (II).
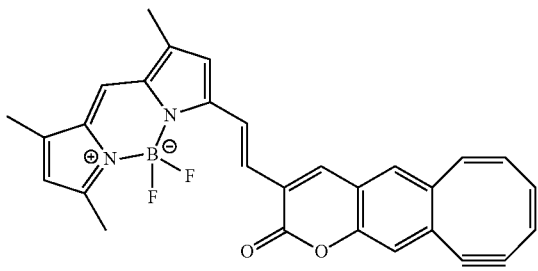 [SMILES: CC1=CC(C)=[N+]2C1=Cc1c(C)cc(/C=C/c3cc4cc5c(cc4oc3=O)C#C/C=C\C=C/5)n1[B-]2(F)F]
(T119)
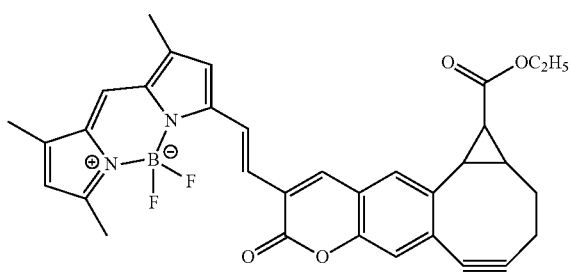 [SMILES: CCOC(=O)C1C2CCC#Cc3cc4oc(=O)c(/C=C/c5cc(C)c6n5[B-](F)(F)[N+]5=C(C)C=C(C)C5=C6)cc4cc3C21]
(T120)
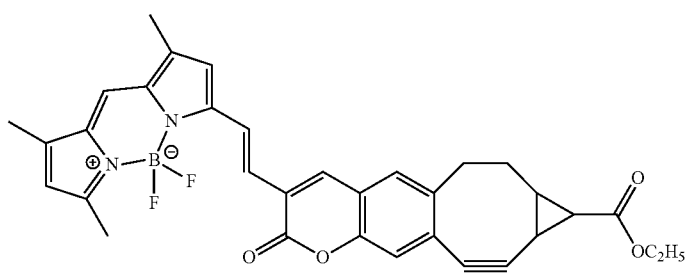 [SMILES: CCOC(=O)C1C2C#Cc3cc4oc(=O)c(/C=C/c5cc(C)c6n5[B-](F)(F)[N+]5=C(C)C=C(C)C5=C6)cc4cc3CCC21]
(T121)
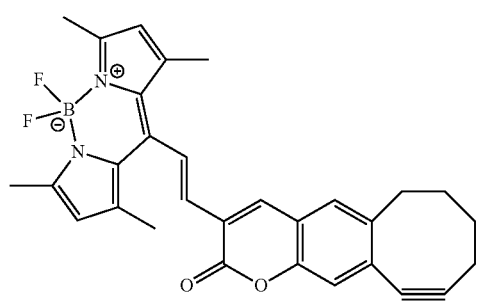 [SMILES: CC1=CC(C)=[N+]2C1=C(/C=C/c1cc3cc4c(cc3oc1=O)C#CCCCC4)c1c(C)cc(C)n1[B-]2(F)F]
(T122)
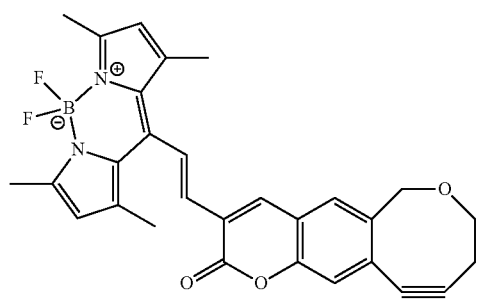 [SMILES: CC1=CC(C)=[N+]2C1=C(/C=C/c1cc3cc4c(cc3oc1=O)C#CCCOC4)c1c(C)cc(C)n1[B-]2(F)F]
(T123)

TABLE 1-continued
Exemplary compounds of formulae (I) and (II).
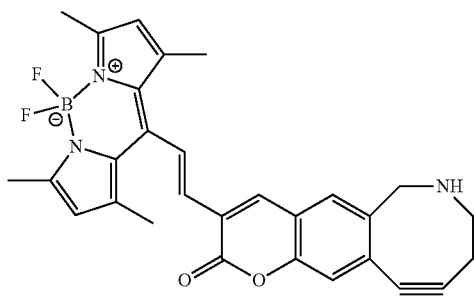 [SMILES: CC1=CC(C)=[N+]2C1=C(/C=C/c1cc3cc4c(cc3oc1=O)C#CCCNC4)c1c(C)cc(C)n1[B-]2(F)F]
(T124)
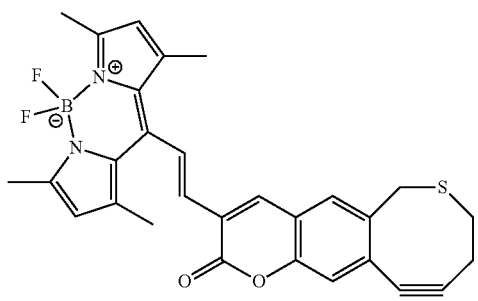
(T125)
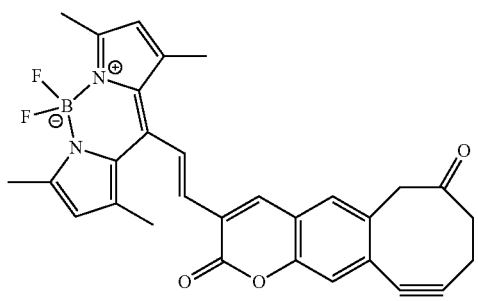 [SMILES: CC1=CC(C)=[N+]2C1=C(/C=C/c1cc3cc4c(cc3oc1=O)C#CCCC(=O)C4)c1c(C)cc(C)n1[B-]2(F)F]
(T126)
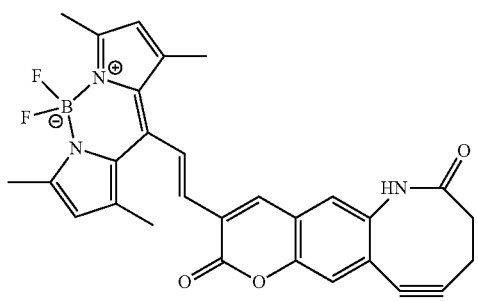 [SMILES: CC1=CC(C)=[N+]2C1=C(/C=C/c1cc3cc4c(cc3oc1=O)C#CCCC(=O)N4)c1c(C)cc(C)n1[B-]2(F)F]
(T127)
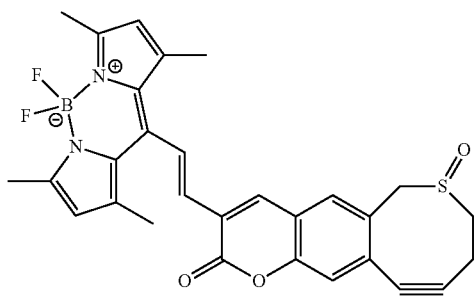 [SMILES: CC1=CC(C)=[N+]2C1=C(/C=C/c1cc3cc4c(cc3oc1=O)C#CCCS(=O)C4)c1c(C)cc(C)n1[B-]2(F)F]
(T128)

TABLE 1-continued
Exemplary compounds of formulae (I) and (II).
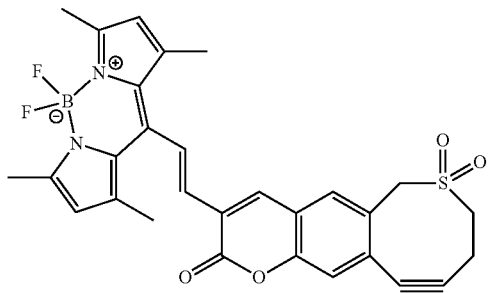 [SMILES: CC1=CC(C)=[N+]2C1=C(/C=C/c1cc3cc4c(cc3oc1=O)C#CCCS(=O)(=O)C4)c1c(C)cc(C)n1[B-]2(F)F]
(T129)
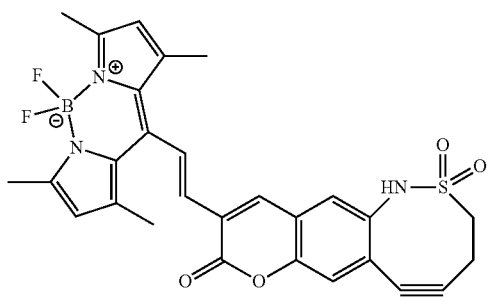 [SMILES: CC1=CC(C)=[N+]2C1=C(/C=C/c1cc3cc4c(cc3oc1=O)C#CCCS(=O)(=O)N4)c1c(C)cc(C)n1[B-]2(F)F]
(T130)
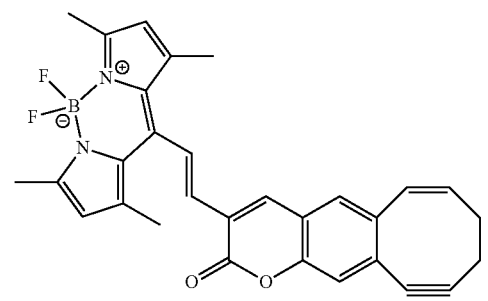 [SMILES: CC1=CC(C)=[N+]2C1=C(/C=C/c1cc3cc4c(cc3oc1=O)C#CCC/C=C\4)c1c(C)cc(C)n1[B-]2(F)F]
(T131)
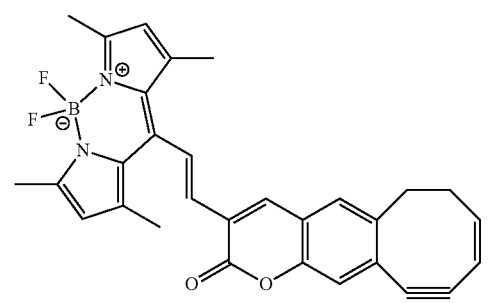 [SMILES: CC1=CC(C)=[N+]2C1=C(/C=C/c1cc3cc4c(cc3oc1=O)C#C/C=C\CC4)c1c(C)cc(C)n1[B-]2(F)F]
(T132)
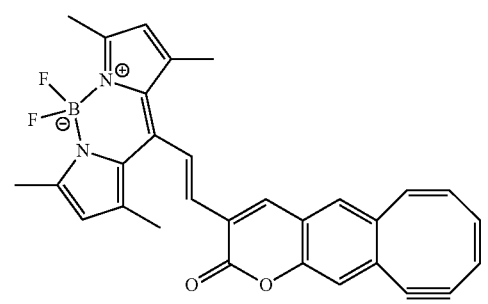 [SMILES: CC1=CC(C)=[N+]2C1=C(/C=C/c1cc3cc4c(cc3oc1=O)C#C/C=C\C=C/4)c1c(C)cc(C)n1[B-]2(F)F]
(T133)

TABLE 1-continued
Exemplary compounds of formulae (I) and (II).
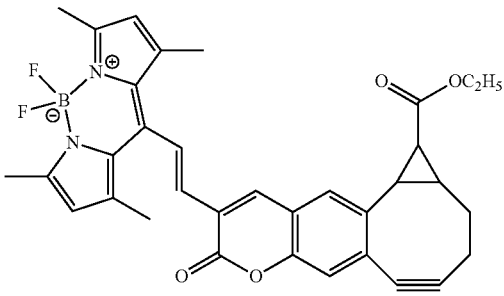 [SMILES: CCOC(=O)C1C2CCC#Cc3cc4oc(=O)c(/C=C/C5=C6C(C)=CC(C)=[N+]6[B-](F)(F)n6c(C)cc(C)c65)cc4cc3C21]
(T134)
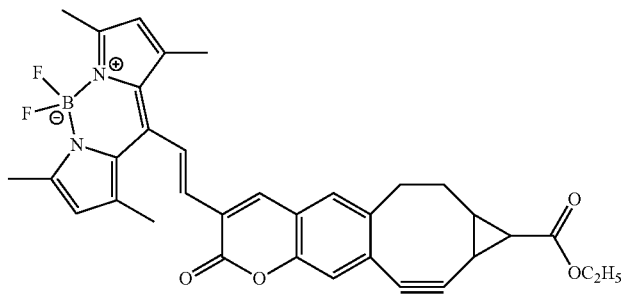 [SMILES: CCOC(=O)C1C2C#Cc3cc4oc(=O)c(/C=C/C5=C6C(C)=CC(C)=[N+]6[B-](F)(F)n6c(C)cc(C)c65)cc4cc3CCC21]
(T135)
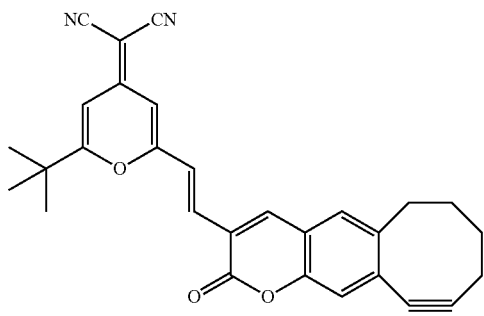 [SMILES: CC(C)(C)C1=CC(=C(C#N)C#N)C=C(/C=C/c2cc3cc4c(cc3oc2=O)C#CCCCC4)O1]
(T136)
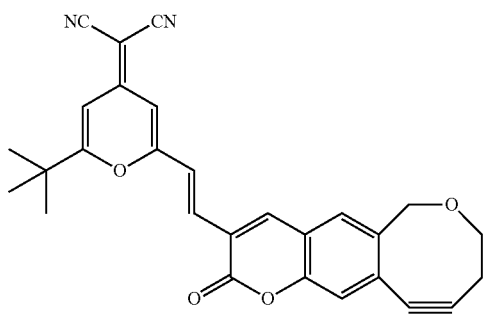 [SMILES: CC(C)(C)C1=CC(=C(C#N)C#N)C=C(/C=C/c2cc3cc4c(cc3oc2=O)C#CCCOC4)O1]
(T137)
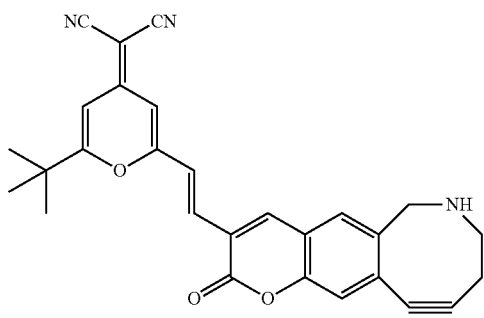 [SMILES: CC(C)(C)C1=CC(=C(C#N)C#N)C=C(/C=C/c2cc3cc4c(cc3oc2=O)C#CCCNC4)O1]
(T138)

TABLE 1-continued
Exemplary compounds of formulae (I) and (II).
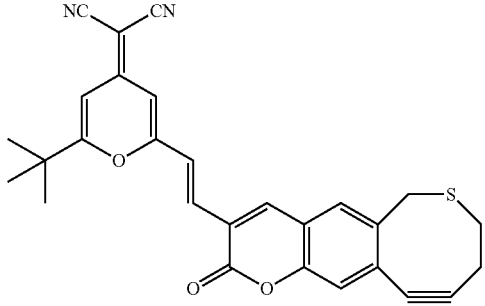 [SMILES: CC(C)(C)C1=CC(=C(C#N)C#N)C=C(/C=C/c2cc3cc4c(cc3oc2=O)C#CCCSC4)O1] (T139)
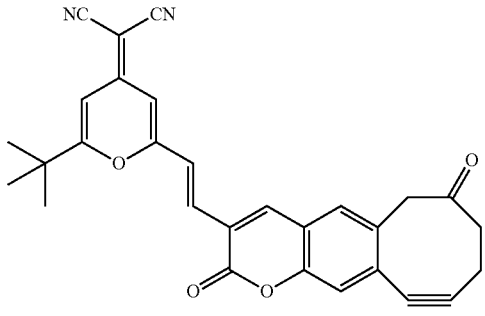 [SMILES: CC(C)(C)C1=CC(=C(C#N)C#N)C=C(/C=C/c2cc3cc4c(cc3oc2=O)C#CCCC(=O)C4)O1] (T140)
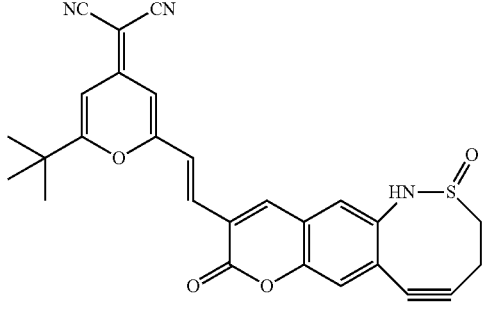 [SMILES: CC(C)(C)C1=CC(=C(C#N)C#N)C=C(/C=C/c2cc3cc4c(cc3oc2=O)C#CCCS(=O)N4)O1] (T141)
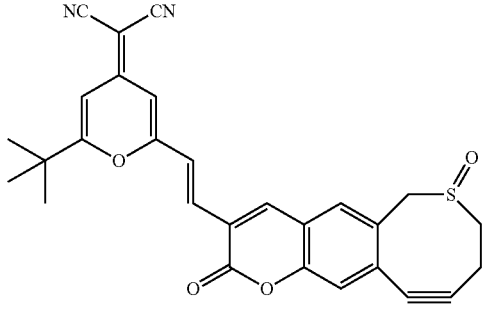 [SMILES: CC(C)(C)C1=CC(=C(C#N)C#N)C=C(/C=C/c2cc3cc4c(cc3oc2=O)C#CCCS(=O)C4)O1] (T142)
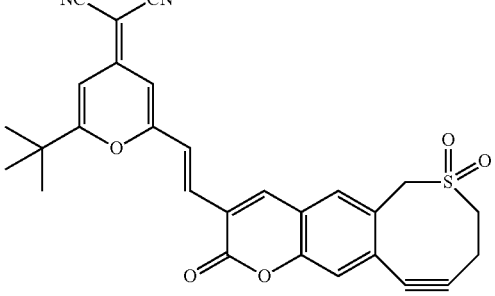 (T143)

TABLE 1-continued
Exemplary compounds of formulae (I) and (II).
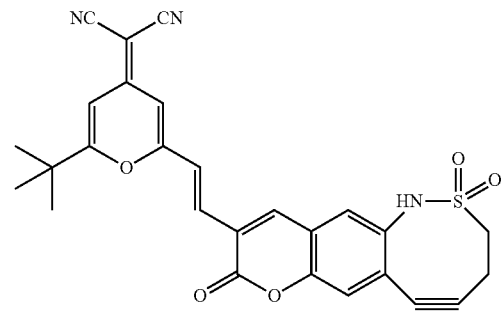 [SMILES: CC(C)(C)C1=CC(=C(C#N)C#N)C=C(/C=C/c2cc3cc4c(cc3oc2=O)C#CCCS(=O)(=O)N4)O1] (T144)
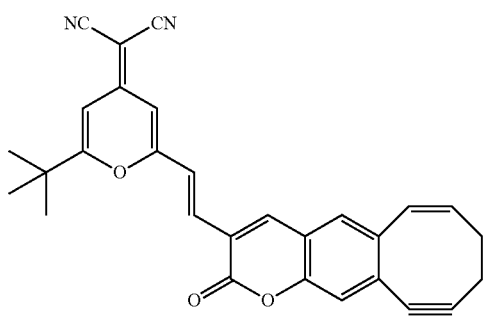 [SMILES: CC(C)(C)C1=CC(=C(C#N)C#N)C=C(/C=C/c2cc3cc4c(cc3oc2=O)C#CCC/C=C\4)O1] (T145)
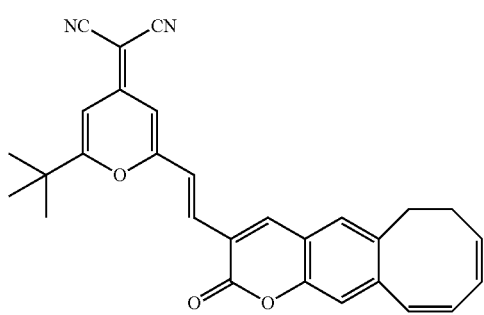 (T146)
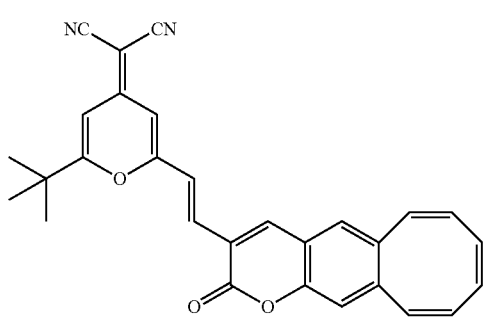 (T147)
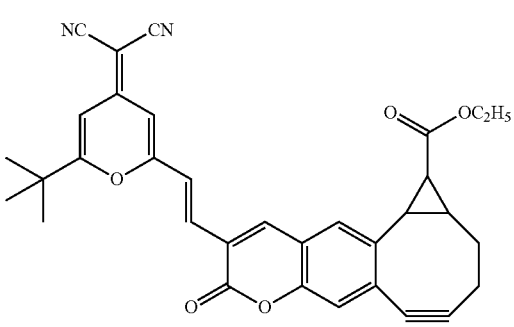 [SMILES: CCOC(=O)C1C2CCC#Cc3cc4oc(=O)c(/C=C/C5=CC(=C(C#N)C#N)C=C(C(C)(C)C)O5)cc4cc3C21] (T148)

TABLE 1-continued
Exemplary compounds of formulae (I) and (II).
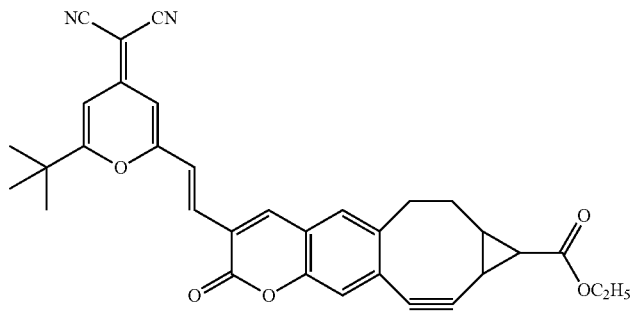 [SMILES: CCOC(=O)C1C2C#Cc3cc4oc(=O)c(/C=C/C5=CC(=C(C#N)C#N)C=C(C(C)(C)C)O5)cc4cc3CCC21]
(T149)
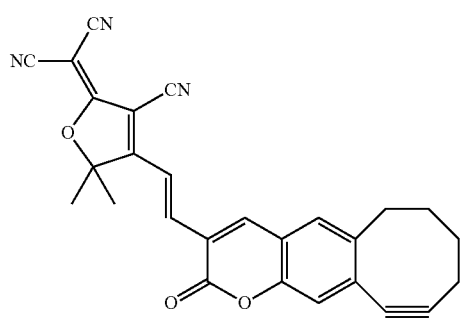 [SMILES: CC1(C)OC(=C(C#N)C#N)C(C#N)=C1/C=C/c1cc2cc3c(cc2oc1=O)C#CCCCC3]
(T150)
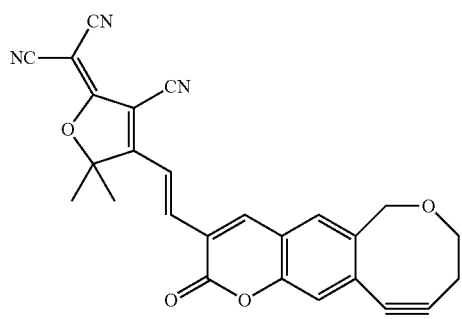 [SMILES: CC1(C)OC(=C(C#N)C#N)C(C#N)=C1/C=C/c1cc2cc3c(cc2oc1=O)C#CCCOC3]
(T151)
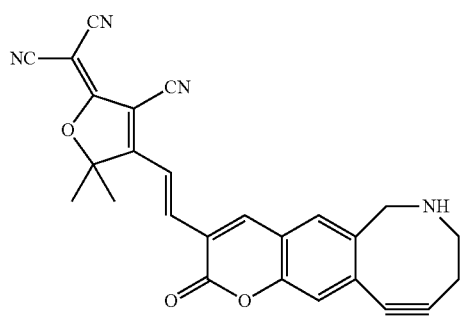 [SMILES: CC1(C)OC(=C(C#N)C#N)C(C#N)=C1/C=C/c1cc2cc3c(cc2oc1=O)C#CCCNC3]
(T152)
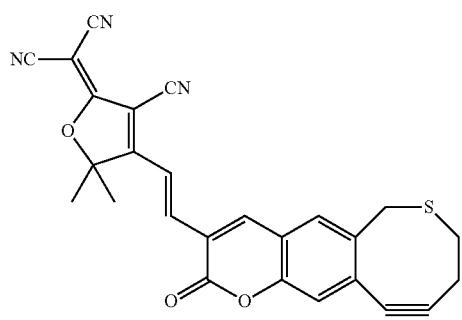 [SMILES: CC1(C)OC(=C(C#N)C#N)C(C#N)=C1/C=C/c1cc2cc3c(cc2oc1=O)C#CCCSC3]
(T153)

TABLE 1-continued
Exemplary compounds of formulae (I) and (II).
(T154)
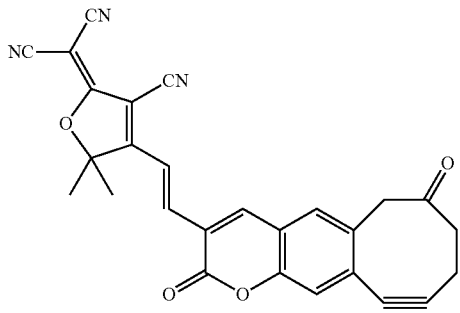 [SMILES: CC1(C)OC(=C(C#N)C#N)C(C#N)=C1/C=C/c1cc2cc3c(cc2oc1=O)C#CCCC(=O)C3]
(T155)
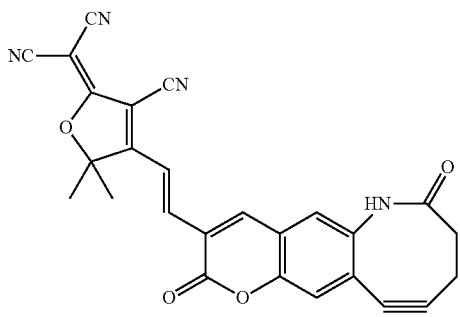 [SMILES: CC1(C)OC(=C(C#N)C#N)C(C#N)=C1/C=C/c1cc2cc3c(cc2oc1=O)C#CCCC(=O)N3]
(T156)
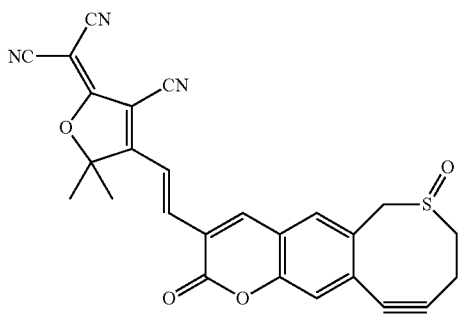 [SMILES: CC1(C)OC(=C(C#N)C#N)C(C#N)=C1/C=C/c1cc2cc3c(cc2oc1=O)C#CCCS(=O)C3]
(T157)
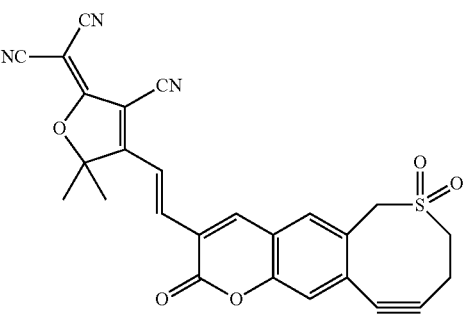 [SMILES: CC1(C)OC(=C(C#N)C#N)C(C#N)=C1/C=C/c1cc2cc3c(cc2oc1=O)C#CCCS(=O)(=O)C3]
(T158)
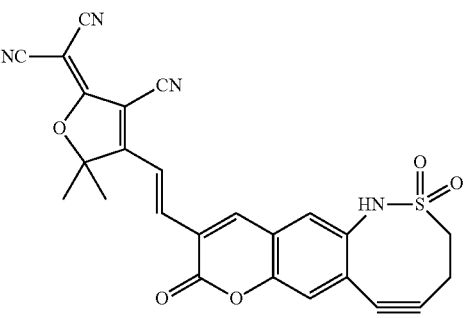 [SMILES: CC1(C)OC(=C(C#N)C#N)C(C#N)=C1/C=C/c1cc2cc3c(cc2oc1=O)C#CCCS(=O)(=O)N3]

TABLE 1-continued
Exemplary compounds of formulae (I) and (II).
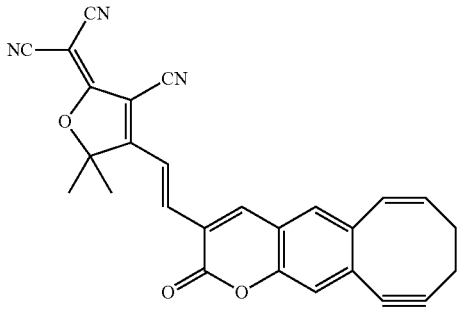 [SMILES: CC1(C)OC(=C(C#N)C#N)C(C#N)=C1/C=C/c1cc2cc3c(cc2oc1=O)C#CCC/C=C\3]
(T159)
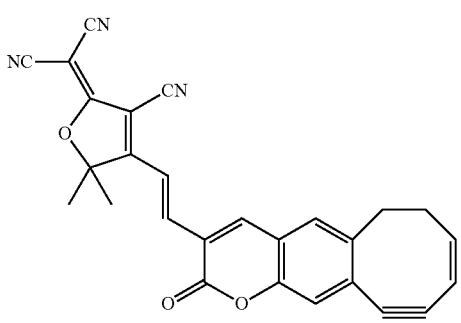 [SMILES: CC1(C)OC(=C(C#N)C#N)C(C#N)=C1/C=C/c1cc2cc3c(cc2oc1=O)C#C/C=C\CC3]
(T160)
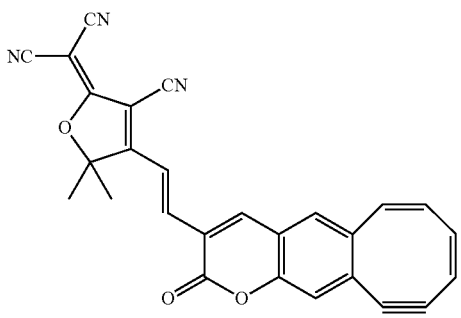 [SMILES: CC1(C)OC(=C(C#N)C#N)C(C#N)=C1/C=C/c1cc2cc3c(cc2oc1=O)C#C/C=C\C=C/3]
(T161)
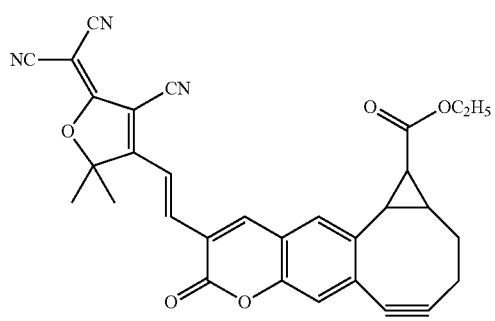 [SMILES: CCOC(=O)C1C2CCC#Cc3cc4oc(=O)c(/C=C/C5=C(C#N)C(=C(C#N)C#N)OC5(C)C)cc4cc3C21]
(T162)
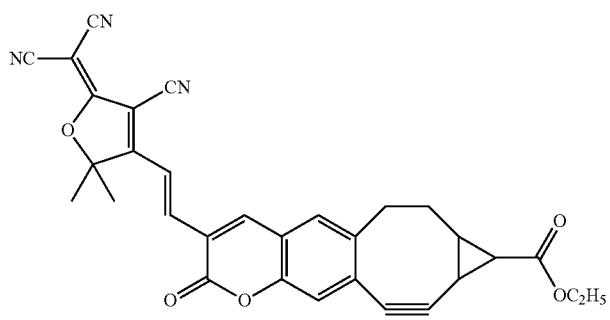 [SMILES: CCOC(=O)C1C2C#Cc3cc4oc(=O)c(/C=C/C5=C(C#N)C(=C(C#N)C#N)OC5(C)C)cc4cc3CCC21]
(T163)

Coumarin-fused cyclooctyne probes were used to detect azide compounds, including the azido-annexed biomolecules. After SPAAC reaction with an azide compound under copper-free condition, the formation of triazole ring will release the fluorescence quenching, and lead to a fluorogenic phenomenon. Compound 1 is an example of such type of probes that undergo SPAAC with azides to give fluorescent triazole products.

In another embodiment, a green-emitting coumarin-based fluorogenic compound 2 was used. An indolium moiety as an electron-withdrawing group is introduced to the 3-position of the coumarin core. Upon excitation, bathochromic shift of the emission wavelength by an ICT process is anticipated.

In another aspect, the present disclosure provides compounds of formula

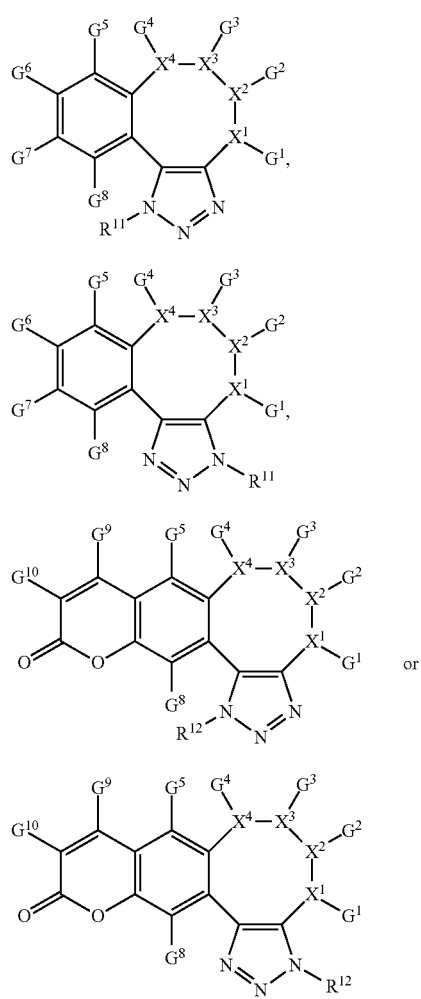

or a salt thereof,
wherein
$X_1$, $X_2$, $X_3$, and $X_4$ are in a 8-membered carbocycle or heterocycle; provided that when the 8-membered ring is a heterocycle, three of $X_1$, $X_2$, $X_3$, and $X_4$ are carbon atoms, and one of $X_1$, $X_2$, $X_3$, and $X_4$ is N, O, P, or S;
each of $G^1$, $G^2$, $G^3$ and $G^4$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, =O, =NOH, =N—$OR^A$, =N—$NH_2$, =N—$NHR^B$, =N—$N(R^B)_2$, and —$NHSO_2R^A$; or $G^1$ and $G^2$ are taken together with their intervening atoms to form an optionally substituted carbocycle or heterocycle; or $G^3$ and $G^4$ are taken together with their intervening atoms to form an optionally substituted carbocycle or heterocycle;
each of $G^5$ and $G^8$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$;
each of $G^6$ and $G^7$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$, or $G^6$ and $G^7$ are taken together with their intervening atoms to form an optionally substituted carbocycle or heterocycle;
each of $G^9$ and $G^{10}$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, optionally substituted heteoaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$.
each of $R^{11}$ and $R^{12}$ is independently selected from the group consisting of hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, optionally substituted heterocyclylalkyl, optionally substituted arylalkyl, optionally substituted heteoarylalkyl, —$OR^A$, —$CH_2OR^A$, —$(CH_2)_tOC(O)R^C$, —$SR^A$, —$N(R^B)_2$, —$(CH_2)_t$—$N(R^B)C(O)R^C$, —$(CH_2)_t$—$C(O)N(R^B)_2$, —CN, —$NO_2$, —$C(O)R^C$, —$(CH_2)_tC(O)OR^A$, —$S(O)R^C$, —$SO_2R^A$, —$SO_2N(R^B)_2$, and —$NHSO_2R^A$;
t is an integer of 1 to 5, inclusive;
each instance of $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur;
each instance of $R^B$ is independently hydrogen, optionally substituted $C_1$-$C_6$ alkyl, optionally substituted alkenyl, optionally substituted alkynyl, optionally substituted heterocyclyl, optionally substituted aryl, or a nitrogen protecting group, or two $R^B$ taken together with the intervening nitrogen form a heterocycle; and each instance of $R^C$ is independently hydrogen, optionally substituted $C_1$-$C_6$ alkyl, optionally substituted alkenyl, optionally substituted alkynyl, optionally substituted heterocyclyl, optionally substituted aryl, or optionally substituted heteroaryl; and provided that when $G^1$ and $G^2$ are taken together with their intervening atoms to form an optionally substituted phenyl, $G^6$ and $G^7$ are taken together with their intervening atoms to form an optionally substituted heterocycle and $X^4$ is not N.

For compounds of formula (II), when $G^1$ and $G^2$ are taken together with their intervening atoms to form an optionally substituted phenyl, $G^6$ and $G^7$ are taken together with their intervening atoms to form an optionally substituted heterocycle and $X^4$ is not N.

For compounds of formula (II), variables $X_1$, $X_2$, $X_3$, $X_4$, $G^1$, $G^2$, $G^3$, $G^5$, $G^6$, $G^7$, $G^8$, $G^9$, and $G^{10}$ are as defined herein.

As generally defined herein, $R^{11}$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, optionally substituted heterocyclylalkyl, optionally substituted arylalkyl, optionally substituted heteoarylalkyl, $-OR^A$, $-CH_2OR^A$, $-(CH_2)_tOC(O)R^C$, $-SR^A$, $-N(R^B)_2$, $-(CH_2)_t-N(R^B)C(O)R^C$, $-(CH_2)_t-C(O)N(R^B)_2$, $-CN$, $-NO_2$, $-C(O)R^C$, $-(CH_2)_tC(O)OR^A$, $-S(O)R^C$, $-SO_2R^A$, $-SO_2N(R^B)_2$, and $-NHSO_2R^A$. In certain embodiments, $R^{11}$ is H. In certain embodiments, $R^{11}$ is halogen. In certain embodiments, $R^{11}$ is optionally substituted $C_1$-$C_6$ alkyl. In certain embodiments, $R^{11}$ is methyl, ethyl, or n-propyl. In certain embodiments, $R^{11}$ is optionally substituted heterocyclylalkyl, optionally substituted arylalkyl, optionally substituted heteoarylalkyl. In certain embodiments, $R^{11}$ is optionally substituted arylalkyl. In certain embodiments, $R^{11}$ is $-CH_2Ph$. In certain embodiments, $R^{11}$ is $-(CH_2)_t-C(O)N(R^B)_2$. In certain embodiments, $R^{11}$ is $-CH_2-C(O)NHR^B$, wherein $R^B$ is independently hydrogen, optionally substituted $C_1$-$C_6$ alkyl, optionally substituted heterocyclyl, optionally substituted aryl, or optionally substituted heteoaryl. In certain embodiments, $R^{11}$ is $-CH_2-C(O)NHR^B$, wherein $R^B$ is of formula

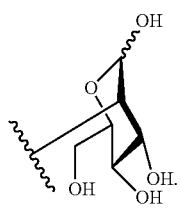

In certain embodiments, $R^{11}$ is $-OR^A$, wherein $R^A$ is independently hydrogen or optionally substituted $C_1$-$C_6$ alkyl. In certain embodiments, $R^{11}$ is $-OH$. In certain embodiments, $R^{11}$ is $-OR^A$, wherein $R^A$ is optionally substituted $C_1$-$C_6$ alkyl. In certain embodiments, $R^{11}$ is $-OCH_3$ or $-OC_2H_5$. In certain embodiments, $R^{11}$ is $-OR^A$, wherein $R^A$ is an oxygen protecting group. In certain embodiments, $R^{11}$ is $-N(R^B)_2$, wherein each instance of $R^B$ is independently hydrogen or optionally substituted $C_1$-$C_6$ alkyl. In certain embodiments, $R^{11}$ is $NH_2$. In certain embodiments, $R^{11}$ is $NHR^B$, wherein $R^B$ is optionally substituted $C_1$-$C_6$ alkyl. In certain embodiments, $R^{11}$ is $NHCH_3$ or $NHC_2H_5$. In certain embodiments, $R^{11}$ is $NHR^B$, wherein $R^B$ is a nitrogen protecting group.

As generally defined herein, $R^{12}$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, optionally substituted heterocyclylalkyl, optionally substituted arylalkyl, optionally substituted heteoarylalkyl, $-OR^A$, $-CH_2OR^A$, $-(CH_2)_tOC(O)R^C$, $-SR^A$, $-N(R^B)_2$, $-(CH_2)_t-N(R^B)C(O)R^C$, $-(CH_2)_t-C(O)N(R^B)_2$, $-CN$, $-NO_2$, $-C(O)R^C$, $-(CH_2)_tC(O)OR^A$, $-S(O)R^C$, $-SO_2R^A$, $-SO_2N(R^B)_2$, and $-NHSO_2R^A$. In certain embodiments, $R^{12}$ is H. In certain embodiments, $R^{12}$ is halogen. In certain embodiments, $R^{12}$ is optionally substituted $C_1$-$C_6$ alkyl. In certain embodiments, $R^{12}$ is methyl, ethyl, or n-propyl. In certain embodiments, $R^{12}$ is optionally substituted heterocyclylalkyl, optionally substituted arylalkyl, optionally substituted heteoarylalkyl. In certain embodiments, $R^{12}$ is optionally substituted arylalkyl. In certain embodiments, $R^{12}$ is $-CH_2Ph$. In certain embodiments, $R^{12}$ is $-(CH_2)_t-C(O)N(R^B)_2$. In certain embodiments, $R^{12}$ is $-CH_2-C(O)NHR^B$, wherein $R^B$ is independently hydrogen, optionally substituted $C_1$-$C_6$ alkyl, optionally substituted heterocyclyl, optionally substituted aryl, or optionally substituted heteoaryl. In certain embodiments, $R^{12}$ is $-CH_2-C(O)NHR^B$, wherein $R^B$ is of formula

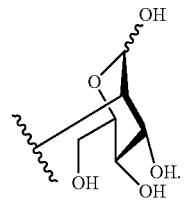

In certain embodiments, $R^{12}$ is $-OR^A$, wherein $R^A$ is independently hydrogen or optionally substituted $C_1$-$C_6$ alkyl. In certain embodiments, $R^{12}$ is $-OH$. In certain embodiments, $R^{12}$ is $-OR^A$, wherein $R^A$ is optionally substituted $C_1$-$C_6$ alkyl. In certain embodiments, $R^{12}$ is $-OCH_3$ or $-OC_2H_5$. In certain embodiments, $R^{12}$ is $-OR^A$, wherein $R^A$ is an oxygen protecting group. In certain embodiments, $R^{12}$ is $-N(R^B)_2$, wherein each instance of $R^B$ is independently hydrogen or optionally substituted $C_1$-$C_6$ alkyl. In certain embodiments, $R^{12}$ is $NH_2$. In certain embodiments, $R^{12}$ is $NHR^B$, wherein $R^B$ is optionally substituted $C_1$-$C_6$ alkyl. In certain embodiments, $R^{12}$ is $NHCH_3$ or $NHC_2H_5$. In certain embodiments, $R^{12}$ is $NHR^B$, wherein $R^B$ is a nitrogen protecting group.

In certain embodiments of formula (I) or (II),

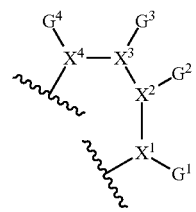

is $-CH_2-CH_2-CH_2-CH_2-$.

The present disclosure also relates to synthetic methods for preparation of benzocyclooctyne compounds as described herein. The present disclosure also demonstrates that such benzocyclooctyne compounds react with organic azides to form triazole products with enhanced fluorescence.

Figure 2:
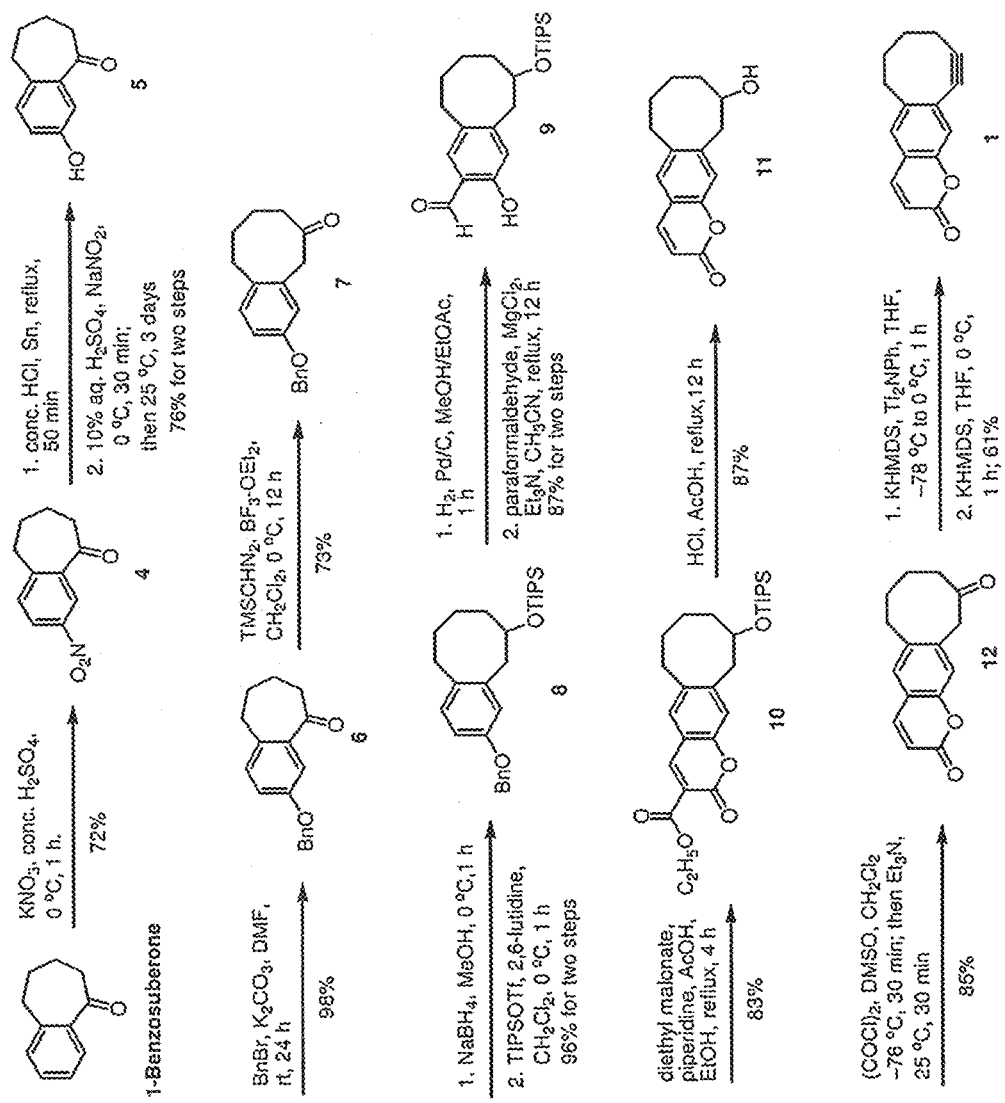
FIG. 2 shows an exemplary synthesis scheme of Compound 1.

FIG. 2 shows the synthesis of Compound 1 comprising steps: (a) treatment of 1-benzosuberone with potassium nitrate in concentrated sulfuric acid at 0° C. to afford compound 4; (Murineddu, G., et al. *J. Med. Chem.* 2005, 48, 7351.)

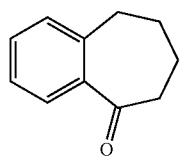

1-Benzosuberone

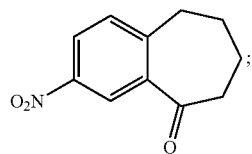

4

(b) treatment of compound 4 with tin metal as the reducing reagent in concentrated HCl to afford an amine intermediate, followed by diazotized with sodium nitrite in acid condition, and hydroxylation to give compound 5; (Smith, P. A. S.; Berry, W. L. *J. Org. Chem.* 1961, 26, 27.)

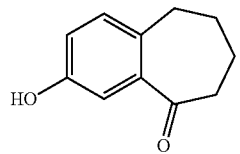

5

(c) treatment of compound 5 in anhydrous N,N-dimethylformamide (DMF) with benz bromide in the presence of potassium carbonate to afford a benzyloxy compound 6:

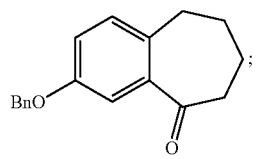

6

(d) ring expansion reaction of compound 6 using (trimethylsilyl)diazomethane in the presence of $BF_3 \cdot OEt_2$ at 0° C. to afford a cyclooctanone product 7:

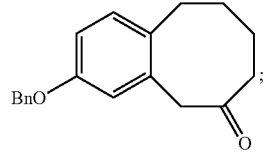

7

(e) treatment of compound 7 with $NaBH_4$ in methanol, followed by treatment with triisopropylsilyl trifluoromethylsulfonate (TIPSOTf) in the presence of 2,6-lutidine, to give a silyl ether 8:

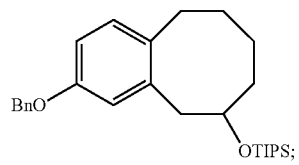

8

(f) removal of the benzyl group in compound 8 by hydrogenation, followed by treatment with anhydrous $MgCl_2$, triethylamine and paraformaldehyde in acetonitrile to afford a salicylaldehyde product 9:

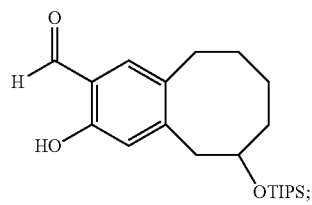

9

(g) treatment of compound 9 with diethyl malonate, piperidine and acetic acid in ethanol to afford a coumarin product 10:

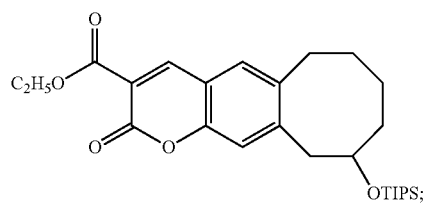

10

(h) treating compound 10 in the media of acetic acid and concentrated HCl to give compound 11:

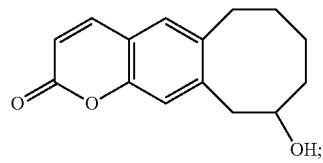

11

(i) Swern oxidation of compound 11 to give ketone 12:

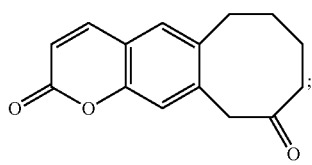

(j) converting compound 12 to an enol triflate, followed by treatment with potassium hexamethyldisilazide (KHMDS) to afford Compound 1.

In one embodiment, Compound 1 reacted with benzyl azide in ethanol/water (1:1) in the absence of copper(I) catalyst to afford the cycloaddition product as a mixture of two triazole reigoisomers 3a and 3b. These two trizaole isomers were separated, and their photophysical properties were investigated, respectively. Similar to Compound 1, compounds 3a and 3b exhibited an absorption band at $\lambda_{max}$=330 nm, albeit with substantially higher extinction coefficients (~2.5 fold). Upon irradiation, compounds 1, 3a and 3b all showed fluorescence emission at $\lambda X_{max}$=400 nm. The quantum yields of triazole compounds 3a ($\Phi_f$=0.23) and 3b ($\Phi_f$=0.22) were 20-fold higher than Compound 1 ($\Phi_f$=0.011). The alkyne-annexed coumarin compound A exhibits the optical property similar to Compound 1; however, compound A requires copper(I) catalyst to proceed the CuAAC reaction.

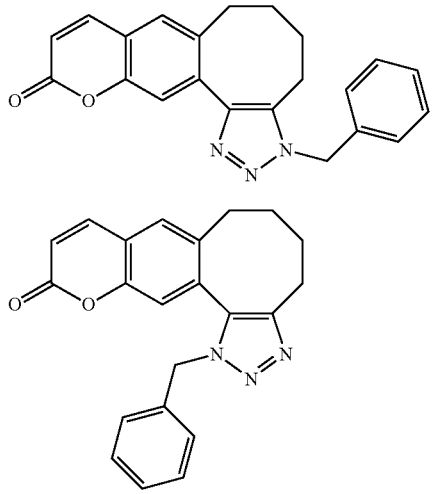

Figure 3:
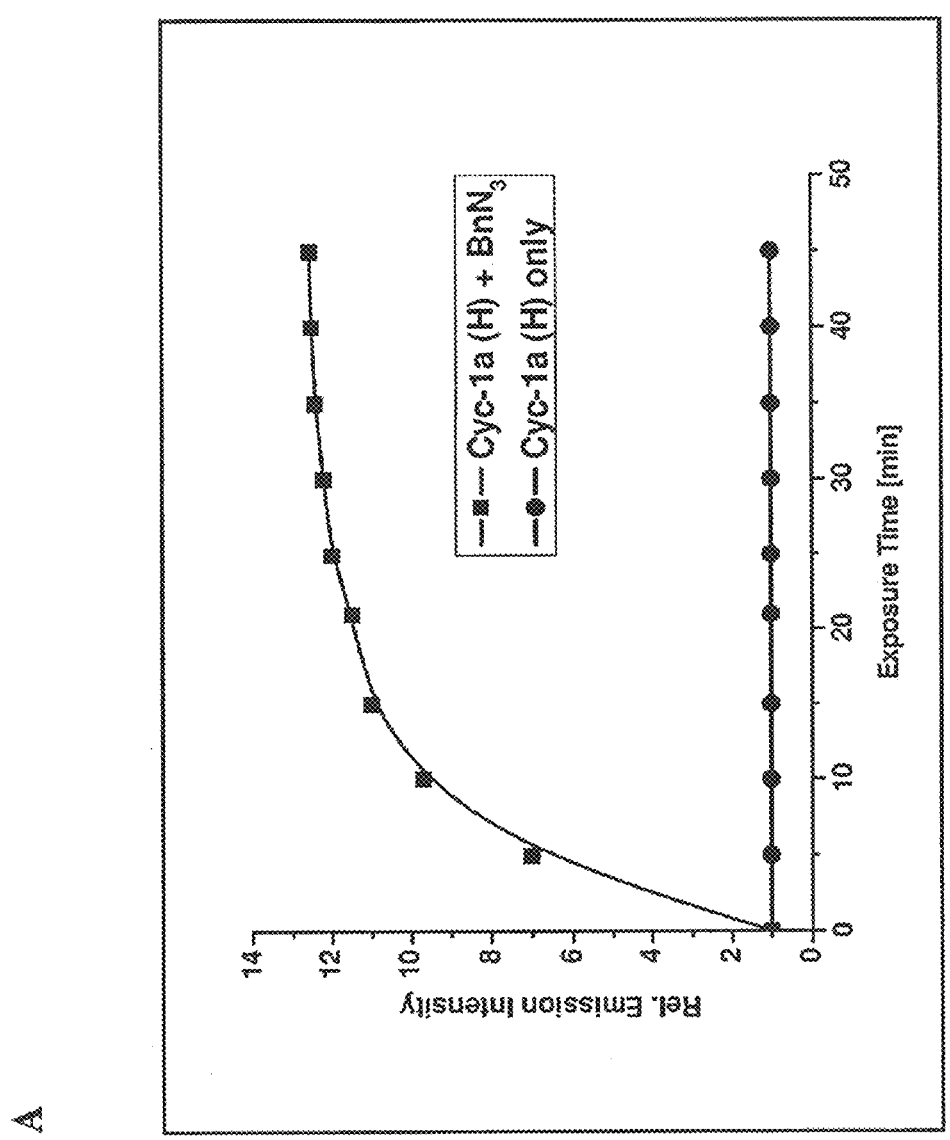
FIG. 3 is a diagram showing the reaction between Compound 1 and benzyl azide. (3a) Time course of normalized fluorescence intensity in the SPAAC reaction of Compound 1 with benzyl azide. (3b) Plot of 1/[compound 1] vs. time for the reaction of Compound 1 and benzyl azide in $CD_3CN$ as monitored by $^1$H-NMR. The measurement was repeated 3 times with a concentration of 19 mM.
Figure 3:
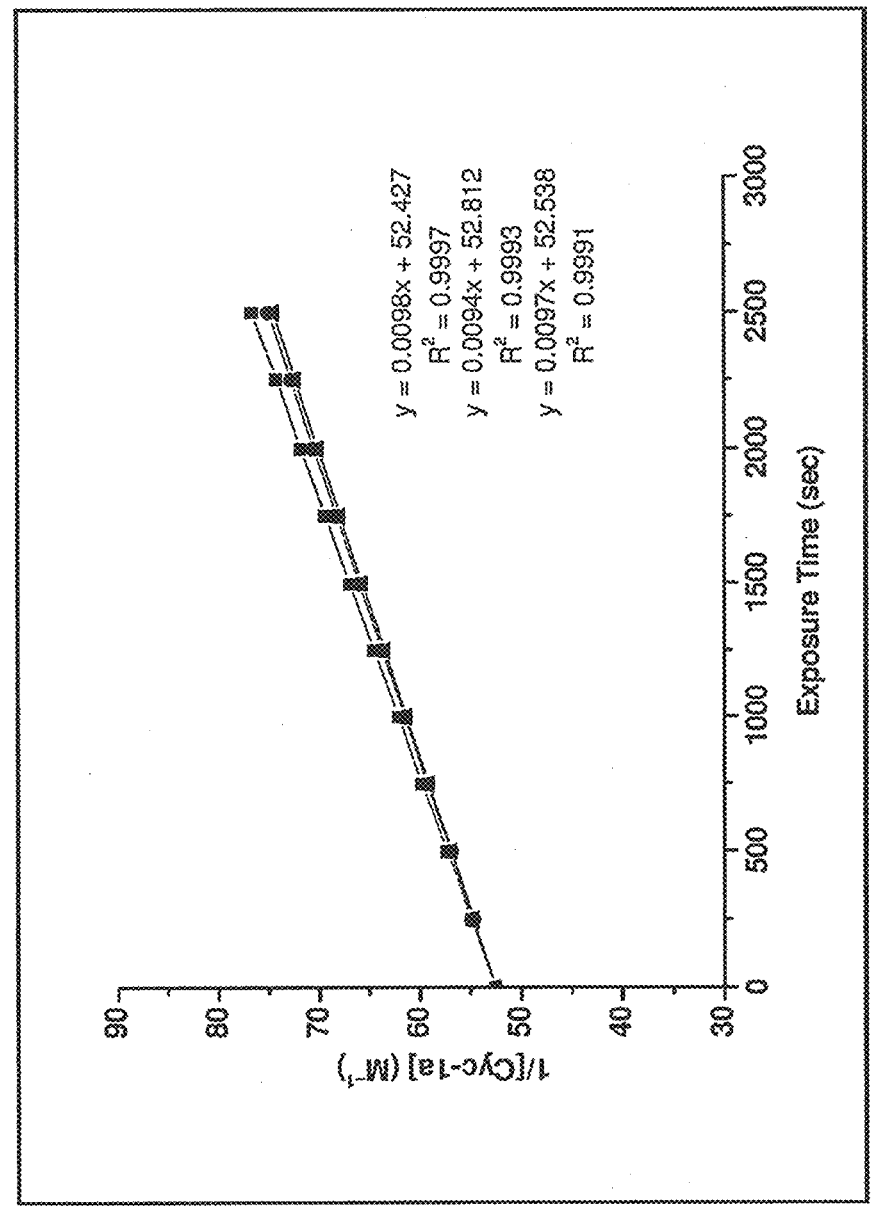

The cycloaddition of compound 1 with benzyl azide was a second-order reaction. FIG. 3a shows the time course of normalized fluorescence intensity during the reaction. FIG. 3b shows the progress of the cycloaddition reaction in CD$_3$CN (19 mM) as monitored by the integration area of the benzylic proton signals in the $^1$H-NMR spectra. The second-order rate constant (k) was determined to be 0.015 M$^{-1}$s$^{-1}$ at 25° C. In comparison, Compound 1 is more reactive than 3-alkoxycyclooctayne (OCT, k=0.002 M$^{-1}$s$^{-1}$) but inferior to 11-alkoxy-dibenzocyclooctyne (DIBO, k=0.06 M$^{-1}$s$^{-1}$). (Agard, et al., *J. Am. Chem. Soc.* 2004, 126, 15046; Ning, et al., *Angew. Chem. Int. Ed.* 2008, 47, 2253).

For biological applications, a fluorogenic compound 2 exhibits the absorption and fluorescence in long wavelengths (~500 nm). The triazole product derived from SPAAC reaction of 2 shows high fluorescence quantum yield in aqueous solution. Compound C containing an indolium moiety at the 3-position of the 7-alkynylcoumarin scaffold was used as a model of compound 2.

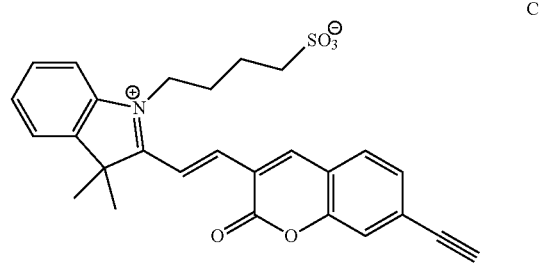

Figure 4:
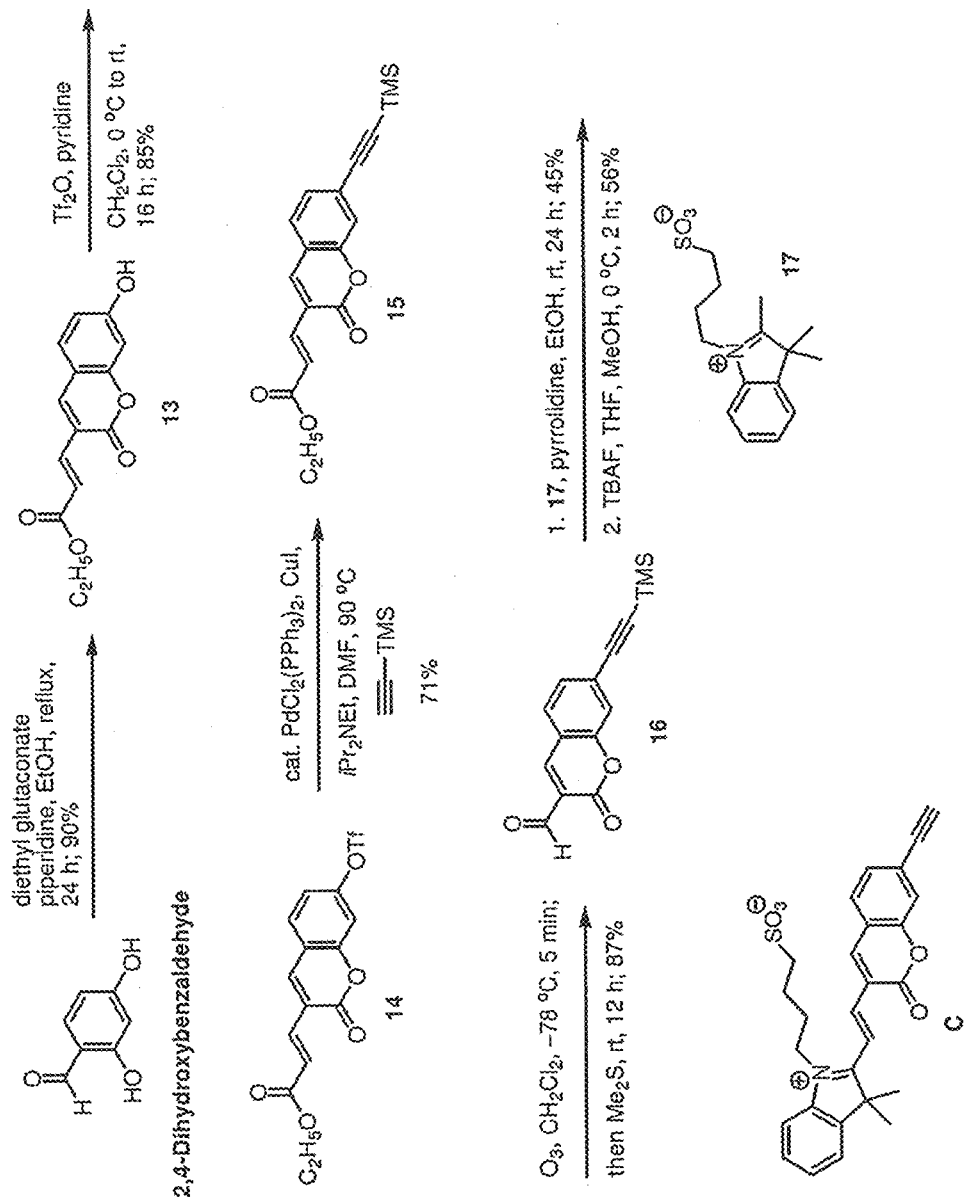
FIG. 4 shows an exemplary synthetic scheme of compound C, a green-emitting coumarin having an alkyne group.
Figure 5:
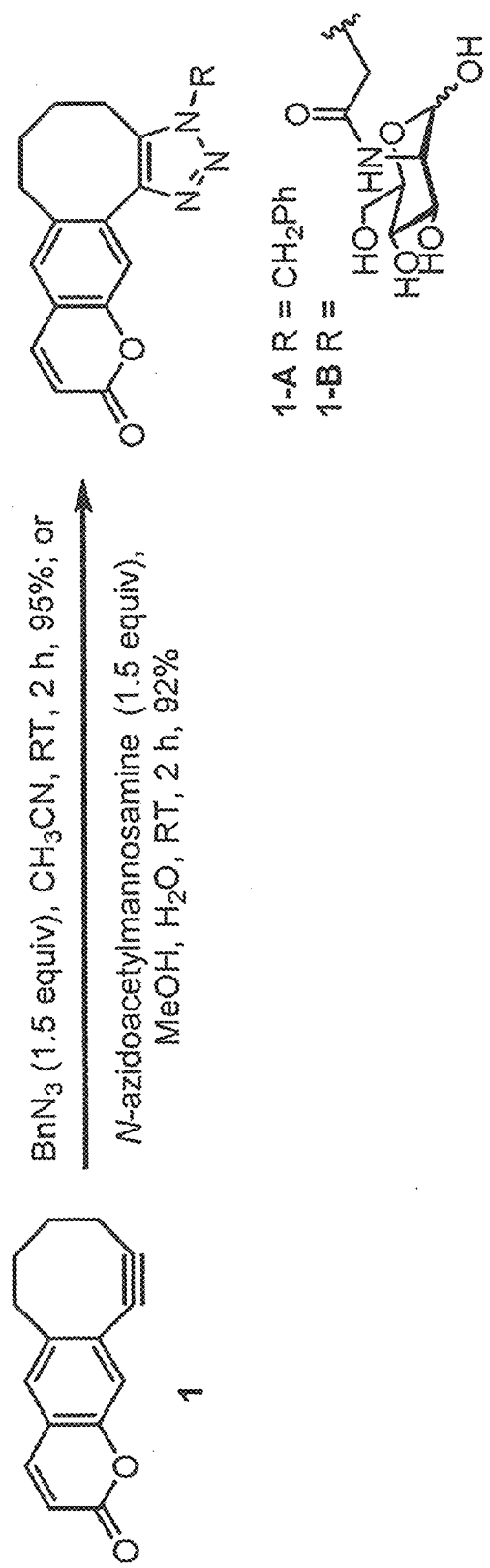
FIG. 5 shows exemplary synthetic schemes Compounds 1-A and 1-B.
Figure 7:
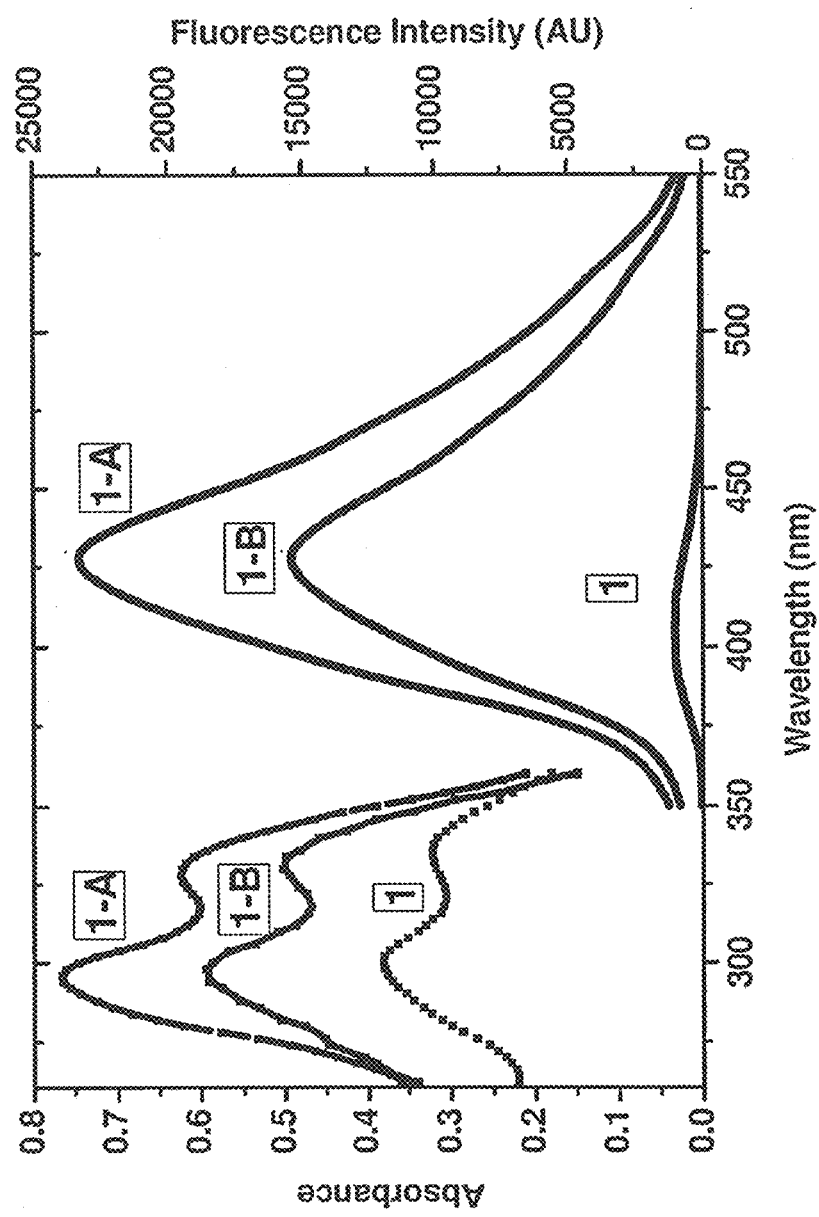
FIG. 7 shows the (7a) absorption and Fluorescence emission spectra ($\lambda_{ex}$=330 nm) of Compounds 1, 1-A, and 1-B (45 µM, PBS buffer containing 10% DMSO, pH 7.4, 37° C.) (8a) and the time course of normalized fluorescence intensity at 435 nm ($\lambda_{ex}$=330 nm) for the ligation reaction of 1 with N-azidoacetylmannosamine in PBS buffer containing 10% DMSO at 37° C. (7b)
Figure 7:
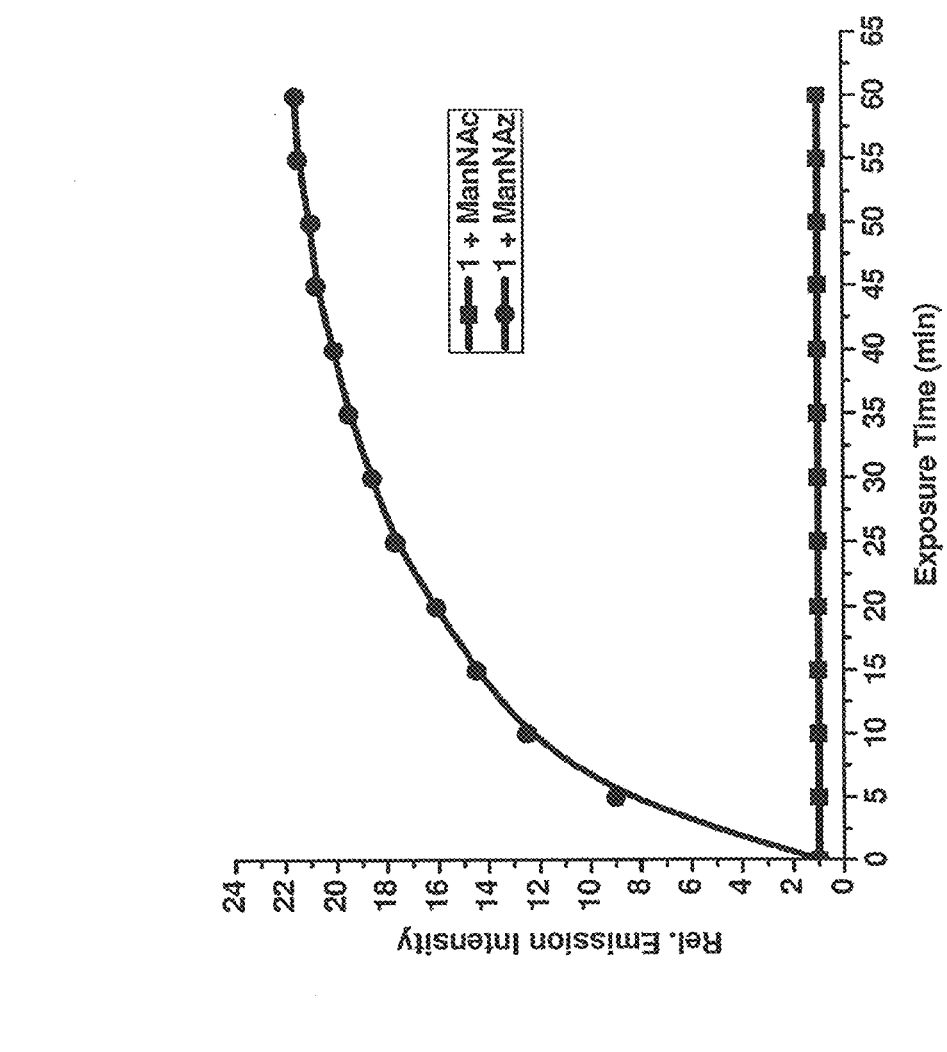

FIG. 4 shows the synthesis of Compound C comprising steps:

(a) treatment of 2,4-dihydroxybenzaldehyde with diethyl glutaconate in the presence of piperidine to afford a coumarin ester 13:

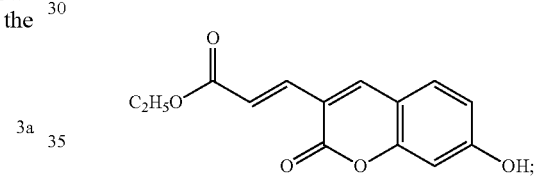

(b) treatment of Compound 13 with trifluoromethylsulfonic anhydride (Tf$_2$O) and pyridine to afford a triflate 14:

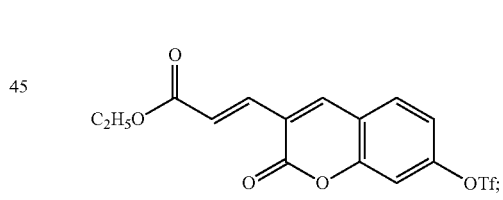

(c) Sonogashira reaction of Compound 14 with trimethylsilylacetylene in the presence of PdCl$_2$(PPh$_3$)$_2$, CuI and diisopropylethylamine to afford a alkynyl-annexed coumarin 15:

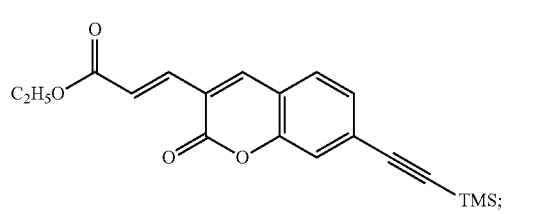

(d) ozonolysis of Compound 15 to give Compound 16:

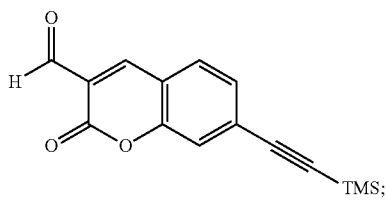

(e) base-mediated condensation reaction of Compound 16 with N-(4-sulfonatobutyl)-2,3,3-trimethylindolium 17, followed by desilylstion with tetrabutylammonium fluoride, to give compound C.

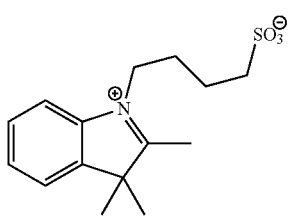

Compound C showed an absorption at $\lambda_{max}$ 500 nm ($\epsilon$=8,600 M$^{-1}$ cm$^{-1}$) and a weak fluorescence at $\lambda_{max}$ 515 nm ($\Phi_f$=0.017). Under standard CuAAC conditions, compound C reacted with benzyl azide to give triazole product 18, which showed an absorption at $\lambda_{max}$ 500 nm ($\Sigma$=32,000 M$^{-1}$ cm$^{-1}$) and a strong fluorescence at $\lambda_{max}$ 520 nm ($\Phi_f$=0.56) in aqueous solution.

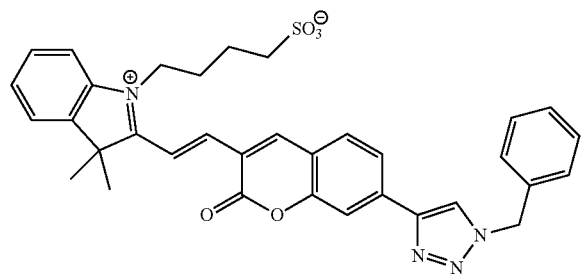

In one aspect, the present disclosure relates to methods (in vivo or in vitro) for detecting and/or imaging organic molecules or biomolecules, particularly those that contains azide groups. Examples include, but are not limited to, amino acids, polypeptides (including peptides and proteins), sugars (including monosaccharides, oligosaccharides, and polysaccharides), and the like. Such molecules may contain or may be modified to contain at least one azide group.

In certain embodiments, the present disclosure provides a method for imaging an azide-containing molecule as described herein. The method can comprise: (a) incubating a compound as described herein (e.g., Compound 1 or Compound 2) with a sample containing an azide-containing molecule under conditions allowing for ligation of the compound to an azido group of the molecule to form a triazole product; and (b) detecting a fluorescent signal released from the triazole product.

In certain embodiments, the present disclosure provides methods (in vivo or in vitro) for detecting an azide-containing molecule as described herein in a sample, such as a biosample. The method comprises: (a) contacting a compound as described herein (e.g., Compound 1 or Compound 2) to a sample suspected of having an azide-containing molecule;

(b) detecting a level of a fluorescent signal released from the sample, and (c) determining presence of the azide-containing molecule in the sample.

An enhanced fluorescent signal as compared to a level of the fluorescent signal in the absence of the compound indicates presence of the azide-containing molecule.

In certain embodiments of the imaging and/or detecting methods described herein, the incubating step is carried out in the absence of a metal catalyst. In certain embodiments, the compound is covalently linked to the azido group. In certain embodiments, the sample contains cells and the azide-containing molecule is located on or inside the cells. In certain embodiments, the azide-containing molecule is a biomolecule molecule. In certain embodiments, the biomolecule is a DNA, RNA, protein or glycan. In certain embodiments, the biomolecule is on a cell surface. In certain embodiments, the biomolecule is intracellular. In certain embodiments, the biomolecule is of avian, mammalian, viral, parasitical, fungal, or bacterial origin. In certain embodiments, the biomolecule is of human origin. In certain embodiments, the biomolecule is associated with a disease or physical condition. In certain embodiments, the disease or physical condition is selected from the group consisting of cancer (such as malignant tumor), rheumatoid arthritis, and inflammation. In certain embodiments, the molecule is an organic molecule.

In some embodiments, the present present disclosure is used for in vivo imaging, e.g., to determine the metabolic or other state of a cell in an organism (e.g., a human). As one non-limiting example, a subject method may be applied to in vivo imaging of cancer cells in an individual (e.g., a mammal, including rodents, lagomorphs, felines, canines, equines, bovines, ovines, caprines, non-human primates, and humans).

Exemplary cancers include, but are not limited to, lung cancer, prostate cancer, breast cancer, colorectal cancer, ovarian cancer, lymphoma, and leukemia.

The term "inflammation" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammations include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease).

The azide-containing molecules to be examined in the methods described herein can be naturally occurring. Alternatively, it can be prepared by modifying a molecule that originally does not contain azide groups using methods known in the art. The azide-containing molecules can be on a cell surface or inside a cell, which can be either a cultured cell or a cell within including a host animal, e.g., a mammalian animal, such as a murine host (e.g., rat, mouse), hamster, canine, feline, bovine, swine, and the like). In some embodiments, the azide-containing molecule is present in vitro in a cell-free reaction. In other embodiments, the molecule is present in a cell and/or displayed on the surface of a cell. In many embodiments of interest, the azide-containing molecule is in a living cell; on the surface of a living cell; in a living organism, e.g., in a living multicellular organism. Suitable living cells include cells that are part of a living multicellular organism; cells isolated from a multicellular organism; immortalized cell lines; and the like.

Where the azide-containing molecule is a polypeptide, the polypeptide may be composed of D-amino acids, L-amino acids, or both, and may be further modified, either naturally, synthetically, or recombinantly, to include other moieties. For example, the polypeptide may be a lipoprotein, a glycoprotein, or other such modified protein.

In general, the azide-containing molecule comprises at least one azide for reaction with modified cycloalkyne according to the present disclosure, but may comprise 2 or more, 3 or more, 5 or more, 10 or more azides. The number of azides that may be present in a target molecule will vary according to the intended application of the final product of the reaction, the nature of the azide-containing molecule itself, and other considerations which will be readily apparent to the ordinarily skilled artisan in practicing the present disclosure as disclosed herein.

In certain embodiments, the compounds provided herein can be further conjugated with a therapeutic agent (e.g., an anti-cancer drug) to deliver the therapeutic agent to a target substrate containing an azide moiety. In certain embodiments, the compounds as described herein are used in delivering cancer drugs.

In certain embodiments, the exemplary compound in any of the methods as described herein (such as imaging or detecting biomolecule) is of the formula

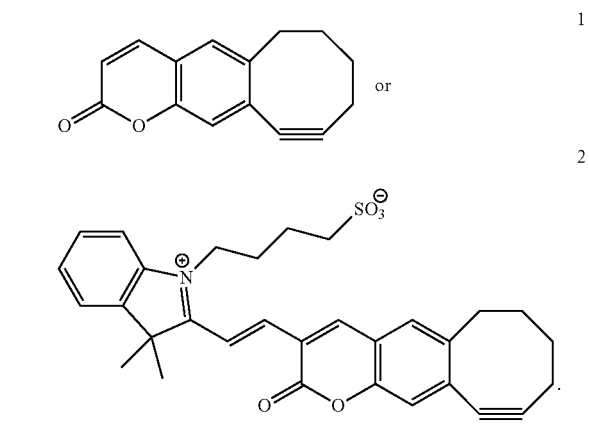

EXAMPLES

Example 1

Synthesis of Exemplary Compounds

Methods and Material

All the reagents were commercially available and used without further purification unless indicated otherwise. All solvents were anhydrous grade unless indicated otherwise. All non-aqueous reactions were carried out in oven-dried glassware under a slight positive pressure of argon unless otherwise noted. Reactions were magnetically stirred and monitored by thin-layer chromatography on silica gel. Column chromatography was performed on silica gel of 40-63 μm particle size. Yields are reported for spectroscopically pure compounds. Melting points were recorded on an Electrothermal MEL-TEMP® 1101D melting point apparatus and are not corrected. NMR spectra were recorded on Bruker AVANCE 600 spectrometer. Chemical shifts are given in δ values relative to tetramethylsilane (TMS); coupling constants J are given in Hz. Internal standards were CDCl$_3$ ($δ_H$=7.24), MeOH-d$_4$ ($δ_H$=3.31) or D$_2$O ($δ_H$=4.79) for $^1$H-NMR spectra, CDCl$_3$ (δ, =77.0 of central line) or MeOH-d$_4$ ($δ_c$=49.15) for $^{13}$C-NMR spectra. The splitting patterns are reported as s (singlet), d (doublet), t (triplet), q (quartet), m (multiplet), br (broad) and dd (double of doublets). IR spectra were recorded on a Thermo Nicolet 380 FT-IR spectrometer. Optical rotations were recorded on a Perkin-Elmer Model 341 polarimeter. High resolution ESI mass spectra were recorded on a Bruker Daltonics spectrometer.

3-Nitro-6,7,8,9-tetrahydrobenzo[7]annulen-5-one (4)

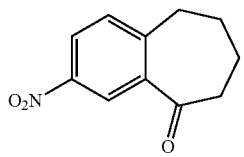 [SMILES: O=C1CCCCc2ccc([N+](=O)[O-])cc21]

A solution of KNO$_3$ (2.8 g, 27.7 mmol) in concentrated H$_2$SO$_4$ (7.5 mL) was added dropwise to a mixture of benzosuberone (4.0 g, 25 mmol) in concentrated H$_2$SO$_4$ (28 mL) at 0° C. in 30 min. The mixture was stirred for 1 h at 0° C., and then the poured into crushed ice. The precipitate was filtered, rinsed with water and dried. The crude product was purified by column chromatography on silica gel (EtOAc/hexane, 1:4) to afford the pure nitro product 4 (3.69 g, 72%). C$_{11}$H$_{11}$NO$_3$; white needles, mp 90-92° C. (lit.[S1] mp 89-90° C.) (Murineddu, G., et al. J. Med. Chem. 2005, 48, 7351.); TLC (EtOAc/hexane, 1:4) R$_f$=0.31; $^1$H NMR (600 MHz, CDCl$_3$) δ 8.53 (1 H, d, J=2.5 Hz), 8.22 (1 H, dd, J=8.3, 2.5 Hz), 7.37 (1 H, d, J=8.3 Hz), 3.01 (2 H, t, J=6.4 Hz), 2.77 (2 H, t, J=6.1 Hz), 1.94-1.90 (2 H, m), 1.85-1.81 (2 H, m); $^{13}$C NMR (150 MHz, CDCl$_3$) δ 203.4, 148.0, 147.0, 139.8, 131.0, 126.2, 123.9, 40.4, 32.4, 24.7, 20.5.

3-Hydroxy-6,7,8,9-tetrahydrobenzo[7]annulen-5-one (5)

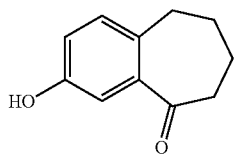 [SMILES: O=C1CCCCc2ccc(O)cc21]

A mixture of compound 4 (2.05 g, 10 mmol) and Sn (8.31 g, 70 mmol) in concentrated HCl (45 mL) and ethanol (25 mL) was heated at reflux for 50 min. The mixture was cooled to room temperature, and the solution was basified with 30% NaOH aqueous solution. The mixture was filtered through a pad of Celite, and washed with ethanol. The filtrate was extracted with EtOAc (5×50 mL). The combined organic extracts were washed with brine (100 mL), dried over MgSO4, filtered, and concentrated under reduced pressure to afford a practically pure amine product (1.45 g) as yellowish solids.

To a cold (0° C.) solution of the above-prepared amine compound (1.45 g, 8.3 mmol) in 10% H$_2$SO$_4$ aqueous solution (40 mL) was cautiously added a solution of NaNO$_2$ (687 mg, 9.96 mmol) in water (3 mL). The mixture was stirred for 30 min at 0° C., and then sulfamic acid was added to destroy excess nitrous acid. The suspension was filtered, and the filtrate was poured into 10% H$_2$SO$_4$ aqueous solution (100 mL) and toluene (50 mL). The mixture was stirred for 3 days at room temperature. The aqueous layer was separated, and extracted with EtoAc (5×30 mL). The combined organic extracts were washed with brine (100 mL), dried over MgSO$_4$, filtered, and concentrated. The crude product was purified by column chromatography on silica gel (EtOAc/hexane, 1:4) to afford a practically pure phenol product 5 (1.11 g, 76% overall yield). C$_{11}$H$_{12}$O$_2$; yellow solid, mp 98-100° C. (lit.[S2] mp 96-99° C.) (Smith, P. A. S.; Berry, W. L. J. Org. Chem. 1961, 26, 27.); TLC (EtOAc/hexane, 3:7) R$_f$=0.37; $^1$H NMR (600 MHz, CDCl$_3$) δ 7.33 (1 H, d, J=2.8 Hz), 7.07 (1 H, d, J=8.2 Hz), 6.94 (1 H, dd, J=8.2, 2.8 Hz), 6.27 (1 H, s, OH), 2.84 (2 H, t, J=5.7 Hz), 2.72 (2 H, t, J=6.4 Hz), 1.86-1.76 (4 H, m); $^{13}$C NMR (150 MHz, CDCl$_3$) δ 206.7, 154.7, 139.2, 133.9, 131.3, 119.8, 114.9, 40.8, 31.6, 25.3, 20.8.

3-Benzyloxy-6,7,8,9-tetrahydrobenzo[7]annulen-5-one (6)

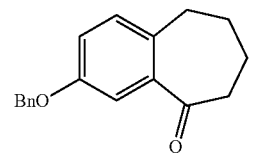 [SMILES: O=C1CCCCc2ccc(OCc3ccccc3)cc21]

A solution of compound 5 (1.25 g, 7.1 mmol) in anhydrous DMF (10 mL) was treated with potassium carbonate (2.1 g, 15.2 mmol) and benzyl bromide (1 mL, 8.4 mmol). The suspension was vigorously stirred for 24 h at room temperature. The mixture was poured into water (20 mL) and extracted with Et$_2$O (4×30 mL). The combined organic extracts were washed with water (3×20 mL) and brine (100 mL), dried over MgSO$_4$, filtered, and concentrated. The crude product was purified by column chromatography on silica gel (EtOAc/hexane, 1:9) to afford a pure benzyloxy product 6 (1.85 g, 98%). C$_{18}$H$_{18}$O$_2$; pale yellow oil; TLC (EtOAc/hexane, 1:9) R$_f$=0.37; $^1$H NMR (600 MHz, CDCl$_3$) δ 7.41 (2 H, d, J=7.2 Hz), 7.37-7.35 (3 H, m), 7.31 (1 H, d, J=7.4 Hz), 7.10 (1 H, d, J=8.3 Hz), 7.02 (1 H, dd, J=8.3, 2.9 Hz), 5.06 (2 H, s), 2.86 (2 H, t, J=5.8 Hz), 2.71 (2 H, t, J=6.2 Hz), 1.84-1.78 (4 H, m); $^{13}$C NMR (150 MHz, CDCl$_3$) δ 205.6, 157.4, 139.5, 136.7, 134.2, 131.0, 128.5 (2×), 127.9, 127.5 (2×), 119.7, 113.2, 70.1, 40.7, 31.6, 25.3, 20.8.

3-Benzyloxy-7,8,9,10-tetrahydro-5H-benzo[8]annulen-6-one (7)

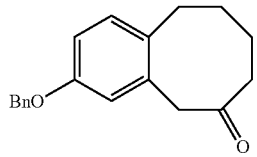 [SMILES: O=C1CCCCc2ccc(OCc3ccccc3)cc2C1]

A solution of (trimethylsilyl)diazomethane (5 mL, ca. 2 M solution in hexane, 10 mmol) in CH$_2$Cl$_2$ (10 mL) was added dropwise over 1 h to a stirred solution of compound 6 (1.6 g, 6 mmol) and BF$_3$.OEt$_2$ (820 µL, 10 mmol) in CH$_2$Cl$_2$ (20 mL) at 0° C. The mixture was stirred for 12 h at 0° C., and then poured into crushed ice. The aqueous layer was extracted with CH$_2$Cl$_2$ (3×20 mL). The combined organic extracts were washed with brine (50 mL), dried over MgSO$_4$, and concentrated to give an orange oil, which was purified by column chromatography on silica gel (EtOAc/hexane, 1:19) to afford the pure cyclooctanone product 7 (1.23 g, 73%). C$_{19}$H$_{20}$O$_2$; colorless oil; TLC (EtOAc/hexane, 1:9) R$_f$=0.29; $^1$H NMR (600 MHz, CDCl$_3$) δ 7.40 (2 H, d, J=7.4 Hz), 7.37-7.34 (2 H, m), 7.31-7.29 (1 H, m), 7.09 (1 H, d, J=8.4 Hz), 6.84 (1 H, dd, J=8.4, 2.7 Hz), 6.75 (1 H, d, J=2.7 Hz), 5.01 (2 H, s), 3.72 (2 H, s), 2.74 (2 H, t, J=5.8 Hz), 2.31 (2 H, t, J=5.3 Hz), 1.81-1.77 (2 H, m), 1.72-1.68 (2 H, m); $^{13}$C NMR (150 MHz, CDCl$_3$) δ 211.8, 157.4, 136.9, 134.7, 133.4, 131.2, 128.5 (2×), 127.9, 127.5 (2×), 116.0, 114.4, 70.0, 48.8, 41.0, 32.3, 31.5, 24.7.

3-Benzyloxy-6-triisopropylsilyloxy-5,6,7,8,9,10-hexahydrobenzo[8]annulene (8)

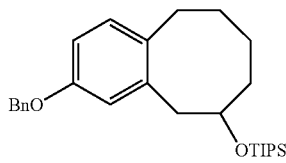

A solution of compound 7 (4.8 g, 17.1 mmol) in methanol (40 mL) was stirred with NaBH$_4$ (970 mg, 25.7 mmol) at 0° C. for 1 h, and then concentrated under reduced pressure. The residue was dissolved in CH$_2$Cl$_2$ (80 mL), and washed with 1 M HCl aqueous solution (50 mL) and brine (50 mL). The organic layer was dried over MgSO$_4$, filtered, and concentrated to provide a crude alcohol product as colorless foam (4.8 g).

Triisopropylsilyl trifluoromethanesulfonate (9.2 mL 34.2 mmol) was added dropwise over a period of 3 min to a cold (0° C.) solution of the above-prepared alcohol (4.8 g, 17.0 mmol) and 2,6-lutidine (8 mL, 68.7 mmol) in anhydrous CH$_2$Cl$_2$ (50 mL). The mixture was stirred for 1 h at room temperature, and then diluted with CH$_2$Cl$_2$ (100 mL). The solution was washed with saturated aqueous NaHCO$_3$ (50 mL), 1 M HCl aqueous solution (50 mL) and brine (50 mL). The organic layer was dried over MgSO$_4$, filtered, and concentrated. The residue was purified by column chromatography on silica gel (EtOAc/hexane, 1:9) to afford a pure silyl ether product 8 (7.2 g, 96% overall yield). C$_{28}$H$_{42}$O$_2$Si; colorless syrup; TLC (EtOAc/hexane, 1:9) R$_f$=0.51; $^1$H NMR (600 MHz, CDCl$_3$) δ 7.41 (2 H, d, J=7.4 Hz), 7.37-7.34 (2 H, m), 7.31-7.28 (1 H, m), 6.99 (1 H, dd, J=6.6, 2.5 Hz), 6.75-6.74 (2 H, m), 5.01 (2 H, s), 3.96-3.93 (1 H, m), 2.91-2.83 (2 H, m), 2.77-2.72 (1 H, m), 2.65-2.61 (1 H, m), 1.76-1.72 (1 H, m), 1.71-1.64 (1 H, m), 1.50-1.41 (3 H, m), 1.18-1.15 (1 H, m), 1.07-1.05 (21 H, m); $^{13}$C NMR (150 MHz, CDCl$_3$) δ 156.8, 138.5, 137.3, 134.1, 130.1, 128.5 (2×), 127.8, 127.5 (2×), 116.7, 112.5, 73.8, 70.0, 40.9, 34.5, 32.3, 32.0, 20.8, 18.2 (6×), 12.4 (3×).

3-Hydroxy-6-triisopropylsilyloxy-5,6,7,8,9,10-hexahydrobenzo[8]annulene-2-carbaldehyde (9)

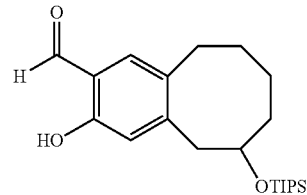

A solution of compound 8 (7.1 g, 16.2 mmol) in methanol (50 mL) and EtOAc (20 mL) was treated with Pd/C (100 mg) under an atmosphere of hydrogen. After stirring for 1 h, the mixture was filtered through Celite, and rinsed with EtOAc. The filtrate was concentrated to give a light brown syrup (5.6 g), which was treated with anhydrous MgCl$_2$ (4.64 g, 48.6 mmol), triethylamine (13.5 mL, 97.2 mmol) and paraformaldehyde (4.86 g, 162 mmol) in anhydrous acetonitrile (150 mL). The suspension was heated at reflux for 12 h. The mixture was cooled to room temperature, and the resulting deep-yellow suspension was acidified with 1 M HCl aqueous solution (200 mL). The solution was extracted with EtOAc (5×150 mL). The combined organic extracts were washed with brine (200 mL), dried over MgSO$_4$, filtered, and concentrated. The crude product was purified by column chromatography on silica gel (EtOAc/hexane, 1:19) to afford a pure salicylaldehyde product 9 (5.3 g, 87% for two steps). C$_{22}$H$_{36}$O$_3$Si; pale yellow syrup; TLC (EtOAc/hexane, 1:9) R$_f$=0.71; $^1$H NMR (600 MHz, CDCl$_3$) δ 10.77 (1 H, s), 9.79 (1 H, s), 7.24 (1 H, s), 6.76 (1 H, s), 4.03-3.99 (1 H, m), 2.94-2.88 (2 H, m), 2.81-2.76 (1 H, m), 2.71-2.67 (1 H, m), 1.80-1.75 (1 H, m), 1.72-1.66 (1 H, m), 1.52-1.46 (2 H, m), 1.43-1.38 (1 H, m), 1.24-1.16 (1 H, m), 1.07-1.05 (21 H, m); $^{13}$C NMR (150 MHz, CDCl$_3$) δ 195.9, 159.5, 148.2, 133.8, 133.7, 119.5, 118.8, 73.2, 41.0, 34.4, 32.2, 32.1, 20.6, 18.1 (6×), 12.4 (3×).

Ethyl 6,7,8,9,10,11-hexahydro-2-oxo-10-triisopropylsilyloxy-2H-cycloocta[g]chromene-3-carboxylate (10)

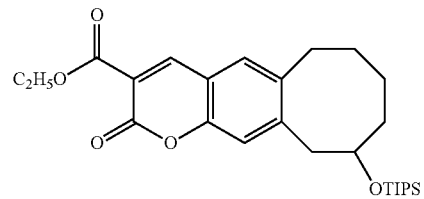

A solution of compound 9 (3.6 g, 9.57 mmol) and diethyl malonate (2.88 mL, 19.0 mmol) in ethanol (30 mL) was treated piperidine (0.3 mL, 3.03 mmol) and glacial AcOH (0.1 mL, 1.73 mmol). The mixture was heated at reflux for 4 h, and then cooled to room temperature. The mixture was concentrated, and purified by column chromatography on silica gel (EtOAc/hexane, 1:9) to afford a pure coumarin product 10 (3.75 g, 83%). C$_{27}$H$_{40}$O$_3$Si; white solid, mp 91-93° C.; TLC (EtOAc/hexane, 1:9) R$_f$=0.20; $^1$H NMR (600 MHz, CDCl$_3$) δ 8.45 (1 H, s), 7.30 (1 H, s), 7.14 (1 H, s), 4.38 (2 H, q, J=7.1 Hz), 4.05-4.02 (1 H, m), 3.03-2.96 (2

H, m), 2.87-2.82 (1 H, m), 2.78-2.76 (1 H, m), 1.76-1.74 (1 H, m), 1.69-1.59 (2 H, m), 1.48-1.44 (2 H, m), 1.38 (3 H, t, J=7.1 Hz), 1.19-1.16 (1 H, m), 1.11-1.03 (21 H, m); $^{13}$C NMR (150 MHz, CDCl$_3$) δ 163.4, 157.2, 153.4, 148.6, 145.6, 139.0, 129.2, 118.0, 117.1, 116.4, 73.1, 61.8, 41.0, 34.5, 32.4, 32.0, 20.6, 18.1 (6×), 14.2, 12.4 (3×).

10-Hydroxy-6,7,8,9,10,11-hexahydro-cycloocta[g]chromene-2-one (11)

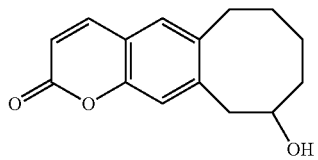 [SMILES: O=c1ccc2cc3c(cc2o1)CC(O)CCCC3]

A solution of compound 10 (473 mg, 1 mmol) in conc. HCl (5 mL) and acetic acid (5 mL) was heated at reflux for 12 h. The mixture was concentrated under reduced pressure. The residue was purified by column chromatography on silica gel (EtOAc/hexane, 1:3) to afford a pure coumarin product 11 (213 mg, 87%) as a colorless solid.

6,7,8,9-Tetrahydro-11H-cycloocta[g]chromene-2,10-dione (12)

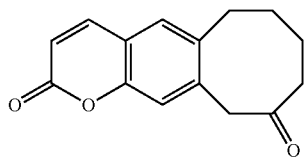 [SMILES: O=C1CCCCc2cc3ccc(=O)oc3cc2C1]

A solution of dimethylsulfoxide (0.25 mL, 3.52 mmol) in CH$_2$Cl$_2$ (3 mL) was added dropwise to a stirred solution of oxalyl chloride (0.15 mL, 1.77 mmol) in CH$_2$Cl$_2$ (3 mL) at –78° C. under nitrogen atmosphere. The solution was stirred for 30 min at –78° C., and then a solution of the alcohol 11 (300 mg, 1.23 mmol) in CH$_2$Cl$_2$ (15 mL) was added. The mixture was stirred for additional 30 min at –78° C., and then triethylamine (1.2 mL, 8.6 mmol) was added. The mixture was allowed to warm to room temperature for 30 min, and then poured into water (20 mL). The mixture was extracted with CH$_2$Cl$_2$ (3×20 mL). The combined organic extracts were washed with water (30 mL) and brine (30 mL), dried over MgSO$_4$, filtered, and concentrated. The residue was purified by column chromatography on silica gel (EtOAc/hexane, 1:4) to afford a pure oxo-coumarin product 12 (253 mg, 85%) as a colorless solid.

10,11-Dehydro-6,7,8,9-tetrahydro-cycloocta[g]chromen-2-one (1)

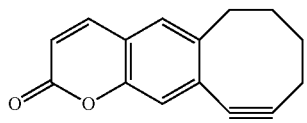 [SMILES: O=c1ccc2cc3c(cc2o1)C#CCCCC3]

KHMDS (0.5 M solution in toluene, 2.2 mL, 1.1 mmol) was added dropwise to solution of compound 12 (242 mg, 1 mmol) in anhydrous THF (20 mL) at –78° C. After stirring for 30 min at –78° C., a solution of N-phenylbis(trifluoromethanesulfonimide) (Tf$_2$NPh, 375 mg, 1.05 mmol) in THF (2 mL) was added dropwise. The mixture was allowed to warm to 0° C. and stirred for 30 min. KHMDS (0.5 M solution in toluene, 2.2 mL, 1.1 mmol) was added dropwise to the mixture again. After stirring for 1 h at 0° C., the mixture was diluted with EtOAc (30 mL), and washed with saturated aqueous solution of NaHCO$_3$ (20 mL) and brine (20 mL). The organic layer was dried over MgSO$_4$, filtered, and concentrated. The residue was purified by column chromatography on silica gel ((EtOAc/hexane, 1:4) to afford a pure coumarin-fused cyclooctyne 1 (137 mg, 61% overall yield) as a colorless solid.

Ethyl(E)-3-(7-hydroxy-2-oxo-2H-chromen-3-yl)-acrylate (13)

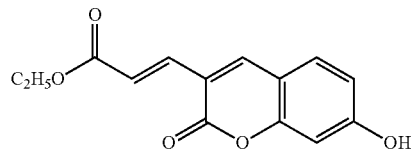

Diethyl glutaconate (4.5 mL, 32 mmol) was added to a solution of 2,4-dihydroxybenzaldehyde (4.14 g, 30 mmol) in methanol (90 mL), followed by addition of 6 drops of piperidine. The mixture was heated at reflux for 24 h, allowed to cool slowly to room temperature, and then chilled to –20° C. The yellow solids were filtered, rinsed with diethyl ether, and dried to yield the desired coumarin compound 13 (7.02 g, 90%). C$_{14}$H$_{12}$O$_5$; pale-yellow solid; TLC (EtOAc/hexane, 3:7) R$_f$=0.25; $^1$H NMR (600 MHz, CD$_3$OD) δ 8.13 (1 H, s), 7.55 (1 H, dd, J=16.5, 0.6 Hz), 7.51 (1 H, d, J=8.6 Hz), 6.91 (1 H, d, J=16.5 Hz), 6.79 (1 H, dd, J=8.6, 2.4 Hz), 6.70 (1 H, d, J=2.4, 0.6 Hz), 4.22 (2 H, q, J=6.9 Hz), 1.30 (3 H, t, J=6.9 Hz).

Ethyl(E)-3-[7-(trimethylsilyl)ethynyl-2-oxo-2H-chromen-3-yl]-acrylate (15)

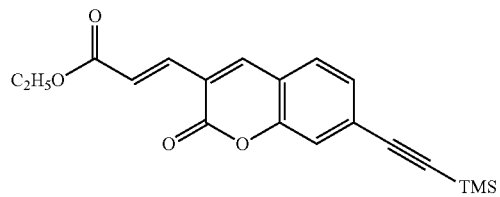

To a cold (0° C.) solution of hydroxycoumarin 13 (7.02 g, 27 mmol) and pyridine (11.8 mL, 145.8 mmol) in CH$_2$Cl$_2$ (150 mL) was added Tf$_2$O (11.8 mL, 70.2 mmol). After stirring for 16 h at room temperature, the mixture was diluted with CH$_2$Cl$_2$ (150 mL), and washed with 1 M HCl aqueous solution (100 mL) and saturated NaHCO$_3$ aqueous solution (100 mL). The organic layer was dried over MgSO$_4$, filtered, and concentrated. The residue was purified by chromatography on a short silica gel column with elution of CH$_2$Cl$_2$ to afford a triflate product 14 (9.0 g, 85%).

A mixture of the above-prepared coumarin triflate (9.0 g, 22.9 mmol), PdCl$_2$(PPh$_3$)$_2$ (0.801 g, 1.14 mmol) and CuI (0.432 g, 2.27 mmol) in anhydrous DMF (100 mL) was flushed with nitrogen for about 1 h. Diisopropylethylamine (7.5 mL) was added. The mixture was heated to 90° C., and then trimethylsilylacetylene (4.9 mL, 35 mmol) was added dropwise. After stirring for 2 h at 90° C., the mixture was concentrated under reduced pressure. The crude product was purified by column chromatography on silica gel (CH$_2$Cl$_2$/hexane, 1:1) to afford a coupling product 15 (5.53 g, 71%) as a pale-yellow solid.

7-(Trimethylsilyl)ethynyl-2-oxo-2H-chromene-3-carbaldehyde (16)

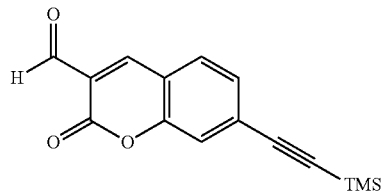 [SMILES: C[Si](C)(C)C#Cc1ccc2cc(C=O)c(=O)oc2c1]

Ozone was bubbled through a solution of ethyl ester 15 (1.04 g, 3.06 mmol) at −78° C. The yellow color of solution faded in about 5 min. Oxygen was bubbled through the solution for 10 min, followed by addition of dimethylsulfide (0.8 mL, 10.82 mmol) in one portion. The mixture was allowed to warm to room temperature, and stirred for additional 6 h. The mixture was concentrated under reduced pressure. The residue was purified by column chromatography on silica gel (EtOAc/hexane, 1:4) to afford the desired 3-formyl coumarin 16 (720 mg, 87%). C$_{15}$H$_{14}$O$_3$Si; pale-yellow solid; TLC (EtOAc/hexane, 3:7) R$_f$=0.51; $^1$H NMR (600 MHz, CDCl$_3$) δ 10.22 (1 H, s), 8.35 (1 H, s), 7.58 (1 H, d, J=8.0 Hz), 7.42 (1 H, s), 7.38 (1 H, d, J=8.1 Hz), 0.26 (9 H, s).

(E)-7-ethynyl-3-[N-(4-sulfonatobutyl)-3,3-dimethyl-3H-indolium-2-yl]ethenyl-2H-chromen-2-one (C)

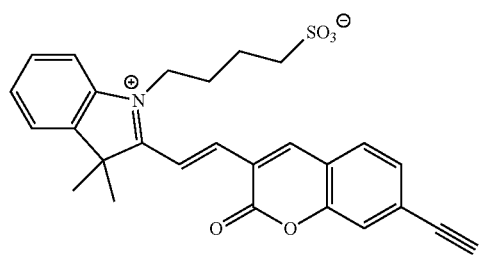

Pyrrolidine (83 μL, 1 mmol) was added to a suspension of 3-formyl coumarin 16 (135 mg, 0.5 mmol) and sulfonated indolium salt 17 (147 mg, 0.5 mmol) in ethanol (10 mL). The mixture was stirred for 24 h at room temperature, and then concentrated under reduced pressure to dryness. The residue was purified by column chromatography on silica gel (CH$_2$Cl$_2$/MeOH, 1:5 to 1:2) to afford an intermediate product (123 mg, 45%).

Tetrabutylammonium fluoride (1 M solution in THF, 0.46 mL, 0.46 mmol) was added to a solution of the above-prepared intermediate compound (123 mg, 0.23 mmol) in methanol (10 mL) at 0° C. The mixture was stirred for 2 h at 0° C., and then concentrated under reduced pressure. The residue was purified by column chromatography (CH$_2$Cl$_2$/MeOH, 1:3) to afford the desired product C (61 mg, 56%) as deep-red solid.

3-Amino-6,7,8,9-tetrahydrobenzocyclohepten-5-one (S1)

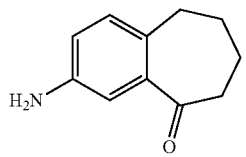

A mixture of nitro compound 4 (2.05 g, 10 mmol) and Sn (8.31 g, 70 mmol) in concentrated HCl (45 mL) and ethanol (25 mL) was heated at reflux for 50 min. The mixture was cooled to room temperature, and basified with 30% NaOH aqueous solution. The mixture was filtered through a pad of Celite, and washed with ethanol. The filtrate was extracted with EtOAc (5×50 mL). The combined organic extracts were washed with brine (100 mL), dried over MgSO$_4$, filtered, and concentrated under reduced pressure to afford the analytically pure amino product S1 (1.44 g, 82%). C$_{11}$H$_{13}$NO, yellowish solid, mp 102-104° C. (lit.[S1] mp 103-105° C.); TLC (EtOAc/hexane, 3:7) R$_f$=0.29; $^1$H NMR (600 MHz, CDCl$_3$) δ 7.02 (1 H, d, J=2.6 Hz), 6.96 (1 H, d, J=8.0 Hz), 6.72 (1 H, dd, J=8.0, 2.6 Hz), 3.65 (2H, br s, NH), 2.79 (2 H, t, J=5.5 Hz), 2.67 (2 H, t, J=6.6 Hz), 1.81-1.74 (4 H, m); $^{13}$C NMR (150 MHz, CDCl$_3$) δ 206.2, 144.9, 139.3, 131.6, 130.7, 118.8, 114.5, 40.8, 31.5, 25.4, 20.9; HRMS calcd for C$_{11}$H$_{14}$NO: 176.1070. found: m/z 176.1069 [M+H]$^+$.

10-Benzyl-6,7,8,9-tetrahydro-cyclooctatriazolo[5,4-g]chromen-2 (2H)-one (1-A)

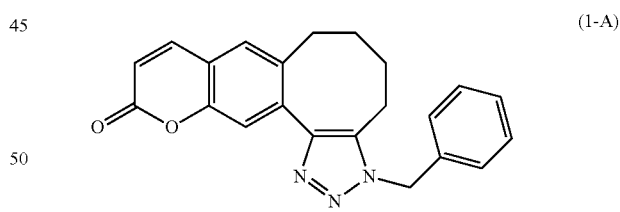

A solution of compound 1 (50 mg, 0.22 mmol) in CH$_3$CN (5 mL) was treated with benzyl azide (44 μL, 0.33 mmol). After stirring for 2 h at room temperature, the mixture was concentrated under reduced pressure. The residue was purified by column chromatography on silica gel (EtOAc/hexane, 3:7) to afford the desired triazole product 1-A (75 mg, 95%). C$_{22}$H$_{19}$N$_3$O$_2$, colorless solid, mp 60-62° C.; TLC (EtOAc/hexane, 1:1) R$_f$=0.35; $^1$H NMR (600 MHz, CDCl$_3$) δ 7.75 (1 H, s), 7.65 (1 H, d, J=9.4 Hz), 7.37-7.32 (3 H, m), 7.24 (1 H, s), 7.20-7.19 (2 H, m), 6.39 (1 H, d, J=9.4 Hz), 5.50 (2 H, s), 2.69-2.67 (2 H, m), 2.65-2.63 (2 H, m), 1.79-1.75 (2 H, m), 1.67-1.64 (2 H, m); $^{13}$C NMR (150 MHz, CDCl$_3$) δ 161.0, 152.4, 143.1, 136.1, 135.3, 135.0, 134.4, 129.0 (2×), 128.7, 128.4, 128.1, 127.1 (2×), 126.9, 116.7, 116.4, 51.9, 30.8, 30.6, 23.9, 20.0; HRMS calcd for $C_{22}H_{20}N_3O_2$: 358.1550. found: m/z 358.1548 [M+H]+.

N-[2-(11-Oxo-4,6,7,11-tetrahydrochromeno[7',6':3,4]cycloocta[1,2-d][1,2,3]triazol-3 (5H)-yl)]acet-amido-2-deoxy-α,β-D-mannopyranose (1-B)

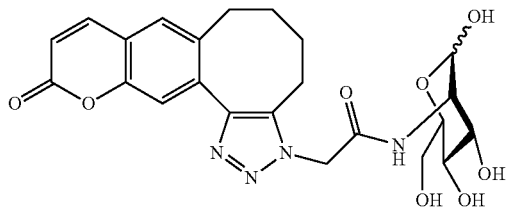

A solution of compound 1 (50 mg, 0.22 mmol) in MeOH (5 mL) and water (1 mL) was treated with N-azidoacetyl-mannosamine (142 mg, 0.33 mmol). After stirring for 2 h at room temperature, the mixture was concentrated under reduced pressure. The residue was purified by column chromatography on silica gel (MeOH/$CH_2Cl_2$, 1:9) to afford the desired triazole product 1-B (98 mg, 92%). $C_{23}H_{26}N_4O_8$, colorless solid, mp 170-172° C. (dec.); TLC (MeOH/$CH_2Cl_2$, 1:8) $R_f$=0.25; $^1$H NMR (600 MHz, DMSO-$d_6$) δ 8.04 (1 H, d, J=9.5 Hz), 7.59 (1 H, s), 7.52 (1 H, s), 6.48 (1 H, d, J=9.5 Hz), 5.15 (1 H, d, J=2.9 Hz), 5.11 (1 H, d, J=6.9 Hz), 4.98-4.85 (1 H, m), 4.89-4.81 (2 H, m), 4.44-4.38 (1 H, m), 3.61-3.59 (3 H, m), 3.53-3.45 (2 H, m), 3.42-3.37 (1 H, m), 3.16-3.14 (2 H, m), 2.86-2.82 (2 H, m), 2.72-2.70 (2 H, m), 1.78 (2 H, br s), 1.61 (2 H, br t, J=5.5 Hz); $^{13}$C NMR (150 MHz, DMSO-$d_6$) δ 165.2, 160.1, 151.9, 143.8, 140.6, 137.0, 135.9, 134.7, 128.8, 118.6, 116.1, 115.2, 92.5, 90.4, 72.9, 72.1, 71.0, 70.5, 68.2, 67.5, 61.5, 61.0, 54.7, 54.2, 50.0, 49.9, 30.6, 29.9, 22.8, 19.6; HRMS calcd for $C_{23}H_{27}N_4O_8$: 487.1829. found: m/z 487.1827 [M+H]+.

Example 2

Detecting and Imaging Biomolecules

Spectroscopic Materials and Methods

Figure 11:
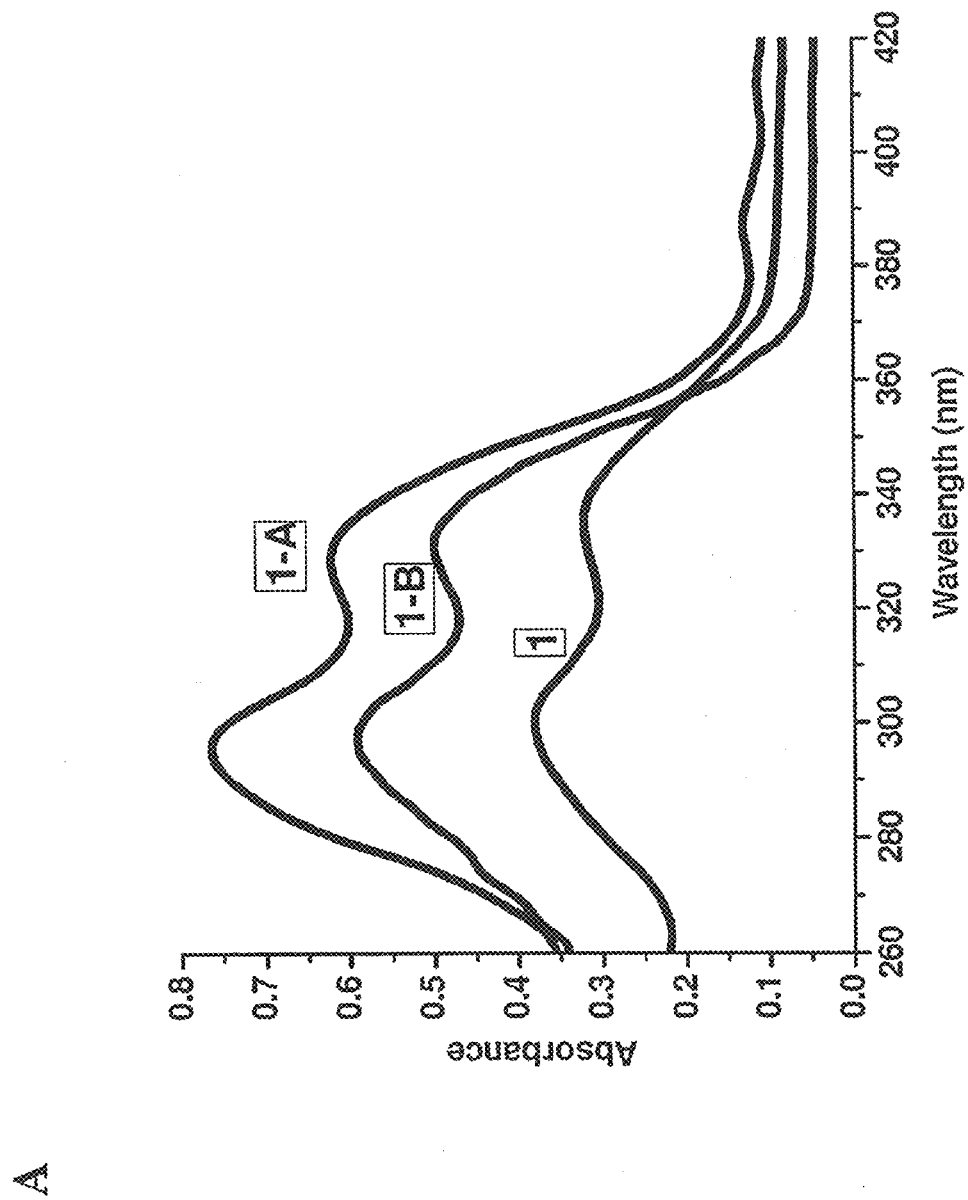
FIG. 11 shows the absorption (11a) and fluorescence emission (11b) spectra ($\lambda_{ex}$=330 nm) of Compounds 1, 1-A and 1-B (45 µM, 10% DMSO in PBS buffer, pH 7.4, 37° C.).
Figure 11:
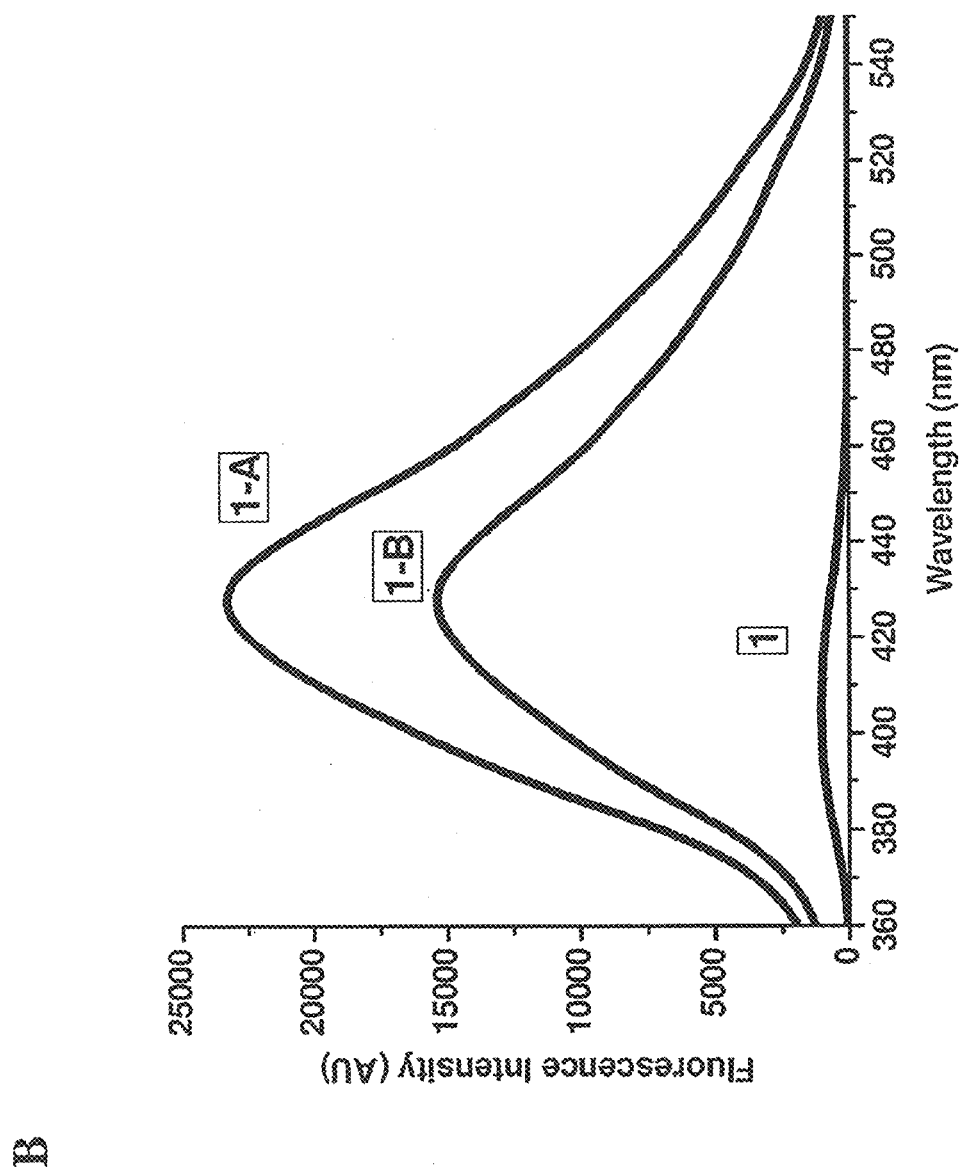

All spectroscopic measurements of Compound 1 and the triazole products 1-A and 1-B were performed in a mixture of 10% DMSO in PBS buffer (FIG. 11). UV-vis spectra and fluorescence spectra were recorded on a Molecular Devices Spectramax M5 spectrometer. For each experiment, the absorbance spectra were measured within an absorbance range of 0.07 to 0.7 (l=10 cm). Quantum yields were determined from the slope of the integrated fluorescence emission between 360 and 550 nm (excitation at 330 nm) versus absorbance using quinine sulfate ($\Phi_f$=0.54±0.03)[S3] as fluorescence standard. The quantum yield was calculated as an average of 4 points according to the following equation:

$$\Phi_{sample} = \Phi_{standard}(A_{standard}/A_{sample})(F_{sample}/F_{standard})(n_{sample}/n_{standard})^2$$

where "Φ" is the quantum yield, "A" is the absorbance at the excitation frequency, "F" is the area under the emission curve, and "n" is the refractive index of the solvent.

Table 1 in FIG. 6 shows the absorption and fluorescence data of Compounds 1 and triazole products 1-A and 1-B recorded under simulated physiological conditions (PBS buffer containing 10% DMSO, pH 7.4, 37° C.). Formation of triazoles 1-A and 1-B were accompanied by a significant increase in fluorescence intensity with a large Stokes shift into a standard range for coumarin emission (FIG. 8a). Upon excitation at 330 nm, Compound 1 produced a weak emission band centered at 405 nm with a low quantum yield ($\Phi_f$=0.011), whereas both triazoles 1-A and 1-B exhibited a strong fluorescence at 435 nm with a quantum yield of 0.23 and 0.21, respectively.

Time Course Measurements by Fluorescence Spectroscopy

To probe the SPAAC reaction under the conditions that would be more typical for biomolecule labeling, the fluorescence response and time course for the reaction of Compound 1 with N-azidoacetylmannosamine (ManNAz) were investigated. The experiments indicated that more than 90% of ManNAz was consumed in 40 min, and the fluorescence intensity reached a plateau in less than 1 h (FIG. 8b).

A solution of Compound 1 (30 mol) and N-azidoacetyl-mannosamine (15 μmol) in a mixture of 10% DMSO in PBS buffer (2.5 mL) was incubated at 37° C. The fluorescence emission intensity at 435 nm upon excitation at 330 nm was monitored in 5 min intervals. For each point the fluorescence intensity was measured over a period of 5 sec and averaged over a total of 3 points. In a control experiment the same conditions were used except that N-acetylmannosamine (15 μmol) was added to the solution.

Kinetics Measurements of Compound (1) by $^1$H NMR

Experiment I: Compound 1 and benzyl azide were pre-dissolved in $CD_3CN$, and then mixed at equimolar concentration of 20 mM. The reaction was monitored by $^1$H-NMR analysis over a period of 1 h. The concentration of each component was determined, based on the concentration of initial compound 1, by integration at multiple chemical shifts in the $^1$H-NMR spectrum. By plotting 1/[1]($M^{-1}$) vs. time (sec), a second order rate constant in unit of $M^{-1}s^{-1}$ was determined using linear regression analysis. This procedure was repeated 3 times with a concentrated of 20 mM to afford a rate constant of 0.012 $M^{-1}s^{-1}$ at 25° C. (FIG. 4B).

Experiment II: Compound 1 and N-azidoacetylman-nosamine were predissolved in $CD_3OD/D_2O$ (5:1, v/v), and then mixed at equimolar concentration of 20 mM. The reaction was monitored by $^1$H-NMR analysis over a period of 1 h. The concentration of each component was determined, based on the concentration of initial compound 1, by integration at multiple chemical shifts in the $^1$H-NMR spectrum. By plotting 1/[1]($M^{-1}$) vs. time (sec), a second order rate constant in unit of $M^{-1}s^{-1}$ was determined using linear regression analysis. This procedure was repeated 3 times with a concentrated of 20 mM to afford a rate constant of 0.010 $M^{-1}s^{-1}$ at 25° C. (FIG. 11).

Example 3

Microscopic Analysis of Fluorescence Labeling in Live Cells

To observe the fluorescence labeled azido-glycoconju-gates in cells, CL1-5 cells (a lung cancer cell line) were seeded on chamber slide (2.5×10$^4$ cells/0.5 mL per wells) and incubated in culture medium (RPMI-1640 supplemented with 10% FBS, 100 U/mL penicillin, 100 μg/mL streptomycin, 1 mM L-glutamine and 1 mM sodium pyruvate) with either 200 μM control sugar (peracetylated N-acetylmannosamine, Ac$_4$ManNAc) or azido-sugar (peracetylated azido-N-acetylmannosamine, Ac$_4$ManNAz) for 3 days.

For Time-lapse imaging of live cells, experiments were carried out using a confocal microscope (TCS-SP5-MP-SMD, Leica) equipped with an incubator to keep the cells in culture conditions. Prewashed cells were incubated with 100 µM compound 1 in PBS buffer with 10% DMSO and images of cell were acquired at 450 nm emission and in 5-min intervals.

Figure 12:
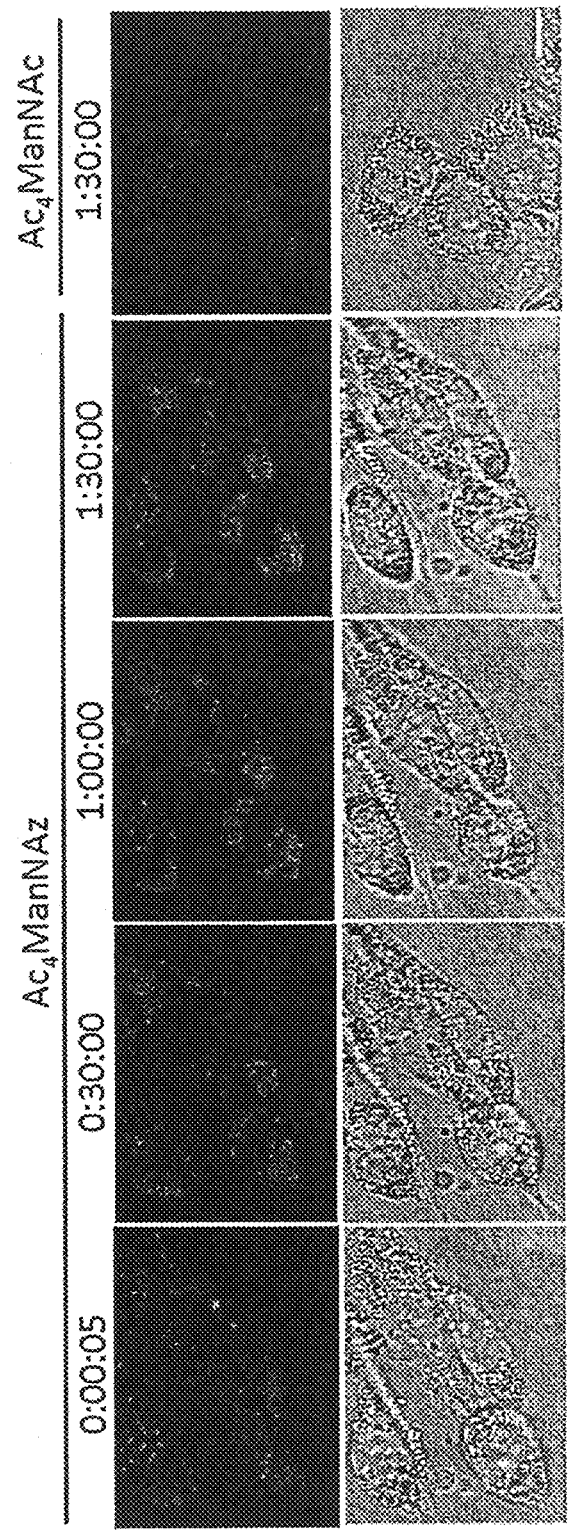
FIG. 12 is a photo showing the time-lapse fluorescence and overlaid images of living CL1-5 cells incubated with Ac$_4$ManNAz and labeled with Compound 1 under no-wash and no-fixation conditions: fluorescence image of cells (upper row) and brightfield overlaid image of cells (bottom row). Control: cells incubated with Ac$_4$ManNAc. (Scale bar: 10 µm).

For comparing the localization of azido-glycans, probe-labeled cells were washed with PBS, fixed with 3% paraformaldehyde in PBS at room temperature for 20 min, permeablized with 0.2% Triton X-100 in PBS at room temperature for 20 min, and blocked with 3% bovine serum albumin in PBS at room temperature for 30 min. Cells were stained with fluorescein conjugated WGA lectin for Golgi, and propidium iodide (PI) for nucleus (FIG. 12).

Figure 8:
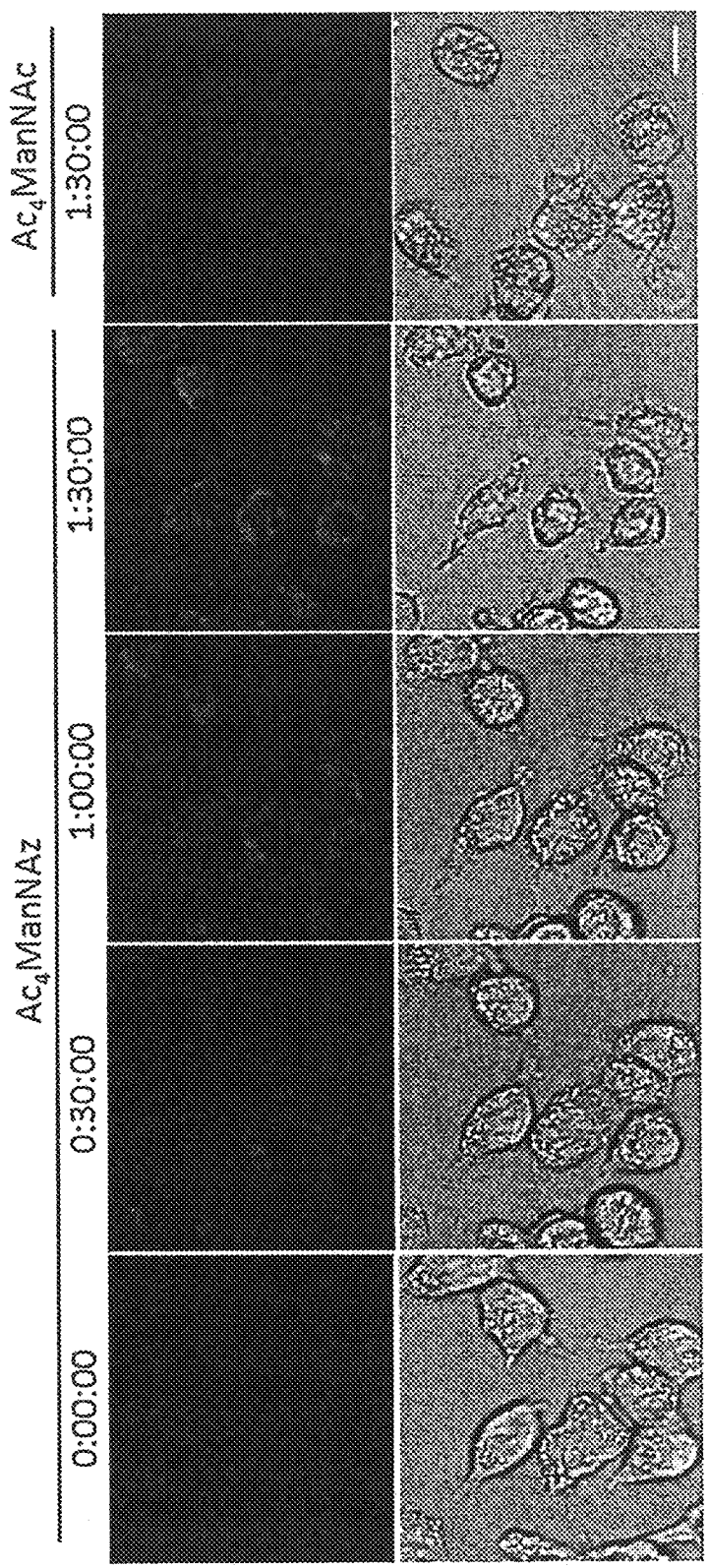
FIG. 8 is a photo showing the time-lapse fluorescence and overlaid images of living CL1-5 cells incubated with Ac4ManNAz and labeled with Compound 1 under no-wash and no-fixation conditions: fluorescence image of cells (upper row) and brightfield overlaid image of cells (bottom row). Control: cells incubated with $Ac_4ManNAc$. (Scale bar: 25 µm).
Figure 9:
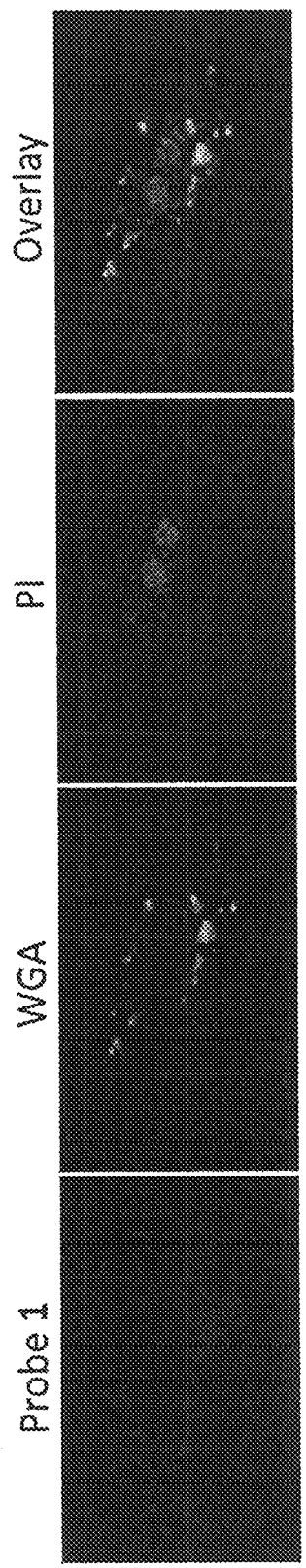
FIG. 9 is a photo showing the localization of probe-labeled sialyl glycoconjugates in CL1-5 cells as visualized by confocal microscopy. Cells incubated with 200 µM of $Ac_4ManNAz$ were labeled with 100 µM of Compound 1 and stained with fluorescein-conjugated WGA lectin (for Golgi) and propidium iodide (for nucleus).
Figure 10:
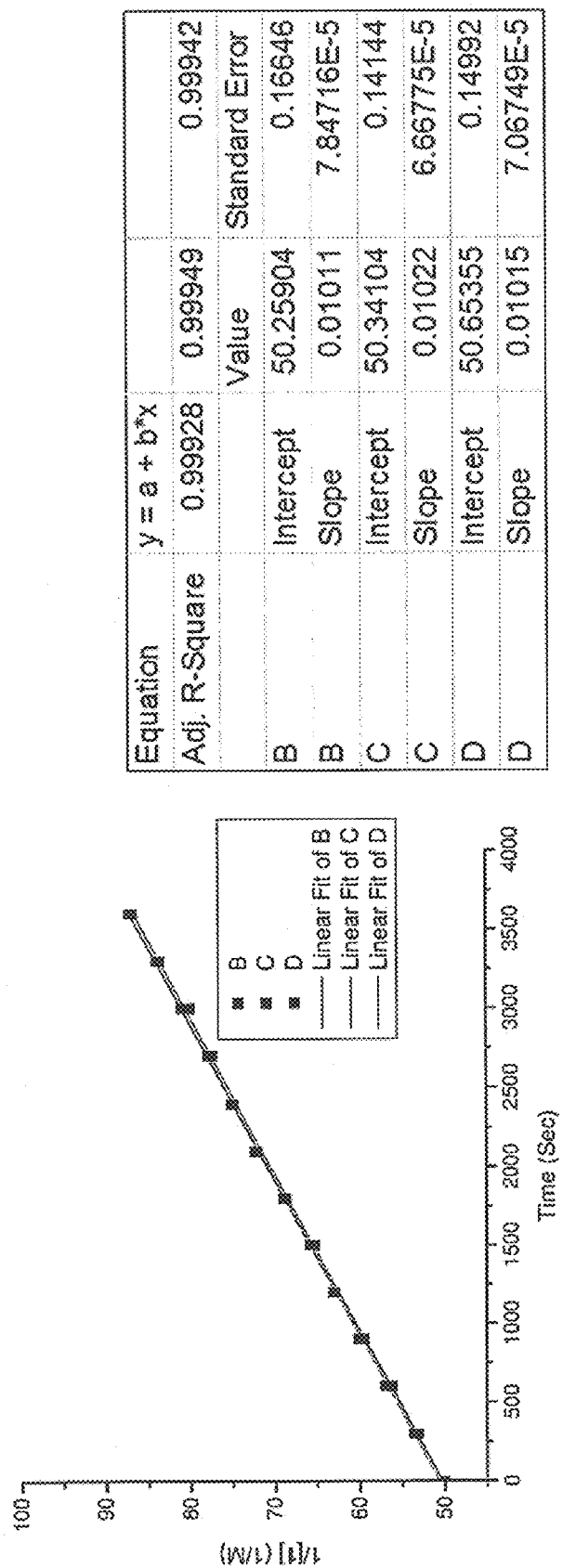
FIG. 10 is a plot of 1/[1] vs. time for the reaction of Compound 1 and N-azidoacetylmannosamine in a solution of CD$_3$OD-D$_2$O (5:1, v/v) as monitored by $^1$H-NMR. The reaction was monitored by $^1$H-NMR.

Performance of Compound 1 in live cell imaging was investigated. Highly invasive lung cancer cells, CL1-5, were cultured in the presence of peracetylated azido-N-acetylmannosamine (Ac$_4$ManNAz, 200 µM) for 3 days to metabolically produce the azido-sialic acid expressed cells. As a negative control, CL1-5 cells were grown in the presence of peracetylated N-acetylmannosamine (Ac$_4$ManNAc, 200 µM). A time course experiment was conducted by treating 100 µM of Compound 1 (once) and conducted by exposing the cells at 5-min intervals under no-wash and no-fixation conditions (FIG. 8 and FIG. 12). The Ac$_4$ManNAz treated cells showed a time-dependent increase of fluorescence intensity, and the cell labeling was complete after 1.5 h. In contrast, the control cells exhibited almost no fluorescence staining, indicating that background labeling is negligible. Furthermore, the localization of azido-containing glycoconjugates in living cells was visualized by confocal microscopy. The cells labeled by Compound 1 were subsequently stained with fluorescein-conjugated WGA lectin (a Golgi marker) and propidium iodide (PI, a nucleus marker). The blue fluorescent signals derived from the coumarin probe are from labeled sialylated glycans apparently showed in cytosol (FIG. 4), which were partially co-localized with Golgi apparatus staining, but not with nucleus staining.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present present disclosure, as defined in the following claims.

REFERENCES

Bach, R. D. J. Am. Chem. Soc. 2009, 131, 5233-5243.
Best, M. D. Biochemistry 2009, 48, 6571-6584.
Jewett et al. Chem. Soc. Rev. 2010, 39, 1272-1279.
Kolb et al. Angew. Chem., Int. Ed. 2001, 40, 2004-2021.
Ning et al. Angew. Chem. Int. Ed. 2008, 47, 2253-2255.
Prescher et al. Nat. Chem. Bio. 2005, 1, 13-21.
Qi et al. Bioconjugate Chem. 2011, 22, 1758-1762.
Sletten, E. M. et al. Angew. Chem. Int. Ed. 2009, 48, 2-27.
Zhou, Z.; et al. J. Am. Chem. Soc. 2004, 126, 8862-8863.
J. N. Demas et al., J. Phys. Chem. 1971, 75, 991-1024.
J. A. Prescher, C. R. Bertozzi, Nat. Chem. Biol. 2005, 1, 13-21.
K. T. Barglow et al., Nat. Methods 2007, 4, 822-827.
R. K. V. Lim et al., Chem. Commun. 2010, 46, 1589-1600.
A. Niederwieser et al., Angew. Chem. 2013, 125, 4359-4363; Angew. Chem. Int. Ed. 2013, 52, 4265-4268.
C. W. Tomoe et al., J. Org. Chem., 2002, 67, 3057-3064.
P. Wu et al., Aldrichim. Acta 2007, 40, 7-17.

J. M. Baskin, C. R. Bertozzi, QSAR Comb. Sci. 2007, 26, 1211-1219.

C.-S. Tsai et al., Proc. Natl. Acad. Sci. U.S.A. 2013, 110, 2466-2471.

C. Le Droumaguet et al., Chem. Soc. Rev. 2010, 39, 1233-1239.

C. Wang et al., Sci. China Chem. 2012, 55, 125-130.

P. Shieh et al., Am. Chem. Soc. 2012, 134, 17428-17431.

X. Ning et al., Angew. Chem. 2008, 120, 2285-2287.

H. Stöckmann et al., Chem. Sci. 2011, 2, 932-936.

J. Dommerholt et al., Angew. Chem. 2010, 122, 9612-9615.

G. de Almeida et al., Angew. Chem. 2012, 124, 2493-2497.

G. de Almeida et al., Angew. Chem. Int. Ed. 2012, 51, 2443-2447.

M. King et al., Chem. Commun. 2012, 48, 9308-9309.

J. C. Jewett et al., Org. Lett. 2011, 13, 5937-5939.

F. Friscourt et al., J. Am. Chem. Soc. 2012, 134, 18809-18815.

A. P. de Silva et al., Chem. Rev. 1997, 97, 1515-1566.

All publications and patent applications cited in this specification are herein incorporated by reference as if each individual publication or patent application was specifically and individually indicated to be incorporated by reference.

Although the foregoing present disclosure has been described in some detail by way of illustration and example for purposes of clarity of understanding, it will be readily apparent to those of ordinary skill in the art in light of the teachings of this present disclosure that certain changes and modifications may be made thereto without departing from the spirit or scope of the appended claims.

We claim:

1. A compound of Formula (I):

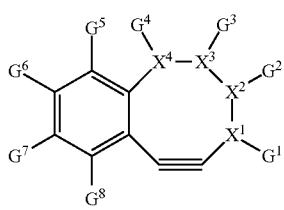

(I)

or a salt thereof,
wherein
$X_1$, $X_2$, $X_3$, and $X_4$ are in a 8-membered carbocycle or heterocycle; provided that when the 8-membered ring is a heterocycle, three of $X_1$, $X_2$, $X_3$, and $X_4$ are carbon atoms, and one of $X_1$, $X_2$, $X_3$, and $X_4$ is N, O, P, or S;

each of $G^1$, $G^2$, $G^3$ and $G^4$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, =O, =NOH, =N—$OR^A$, =N—$NH_2$, =N—$NHR^B$, =N—$N(R^B)_2$, and —$NHSO_2R^A$; or $G^1$ and $G^2$ are taken together with their intervening atoms to form an optionally substituted carbocycle or heterocycle; or $G^3$ and $G^4$ are taken together with their intervening atoms to form an optionally substituted carbocycle or heterocycle;

each of $G^5$ and $G^8$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$;

each of $G^6$ and $G^7$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, —$OR^A$, —$CH_2OR^A$, —$OC(O)R^C$, —$SR^A$, —$N(R^B)_2$, —$N(R^B)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, and —$NHSO_2R^A$, or $G^6$ and $G^7$ are taken together with their intervening atoms to form an optionally substituted carbocycle or heterocycle;

each instance of $R^A$ is independently hydrogen, optionally substituted $C_1$-$C_6$ alkyl, optionally substituted alkenyl, optionally substituted alkynyl, optionally substituted heterocyclyl, optionally substituted aryl, or optionally substituted heteroaryl, or an oxygen protecting group when attached to an oxygen, or a sulfur protecting group when attaching to sulfur;

each instance of $R^B$ is independently hydrogen, optionally substituted $C_1$-$C_6$ alkyl, optionally substituted alkenyl, optionally substituted alkynyl, optionally substituted heterocyclyl, optionally substituted aryl, or optionally substituted heteroaryl, or a nitrogen protecting group, or two $R^B$ taken together with the intervening nitrogen form a heterocycle;

each instance of $R^C$ is independently hydrogen, optionally substituted $C_1$-$C_6$ alkyl, optionally substituted alkenyl, optionally substituted alkynyl, optionally substituted heterocyclyl, optionally substituted aryl, or optionally substituted heteroaryl; and provided that when $G^1$ and $G^2$ are taken together with their intervening atoms to form an optionally substituted phenyl, $G^6$ and $G^7$ are taken together with their intervening atoms to form an optionally substituted heterocycle and $X^4$ is not N.

2. The compound of claim 1, wherein $G^6$ and $G^7$ are taken together with their intervening atoms to form an optionally substituted heterocycle.

3. The compound of claim 1, wherein the compound is of Formula (II)

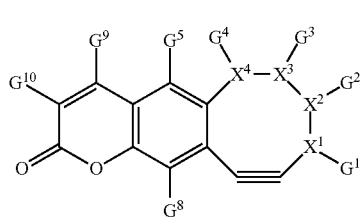

(II)

or a salt thereof,
wherein
each of $G^9$ and $G^{10}$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, optionally substituted heteoaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, and —NHSO$_2$R$^A$.

4. The compound of any one of claims 3, wherein G$^9$ is hydrogen and G$^{10}$ is optionally substituted alkenyl.

5. The compound of claim 4, wherein G$^{10}$ is of Formula (G-i).

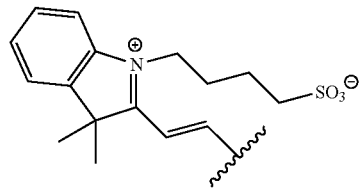

(G-i)

6. The compound of claim 3, wherein the compound is one of the compounds listed in Table 1.

7. The compound of claim 3, wherein the compound is one of the formulae:

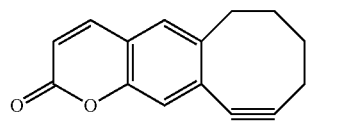

(1)

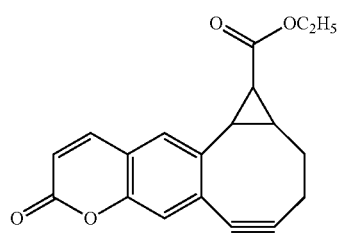

(T13)

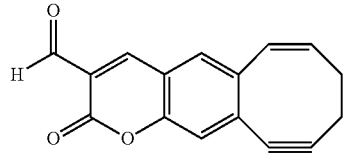

(T23A)

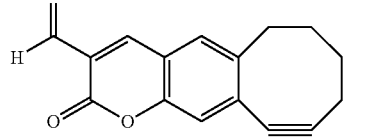

(T23B)

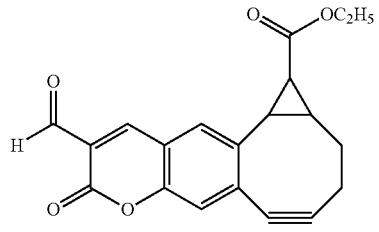

(T36)

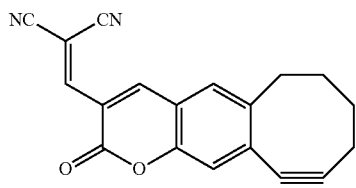

(T38)

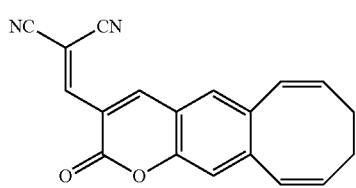

(T47)

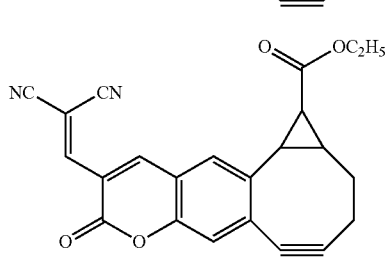

(T74)

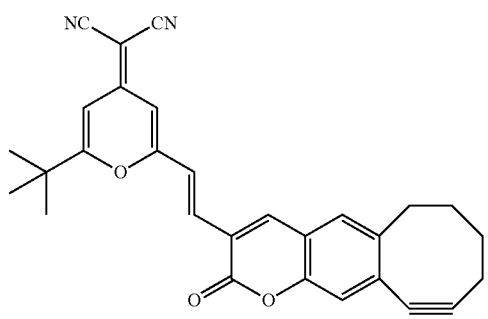

(T136)

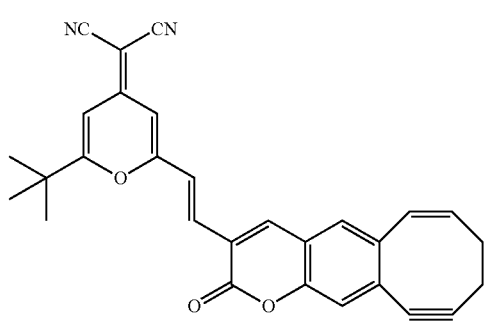

(T145)

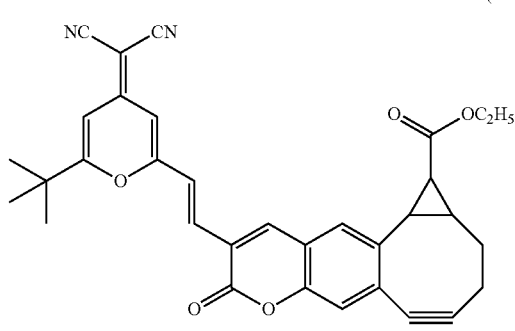

(T148)

(T162) 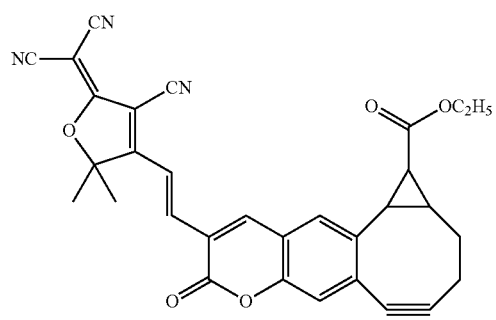
(C2) 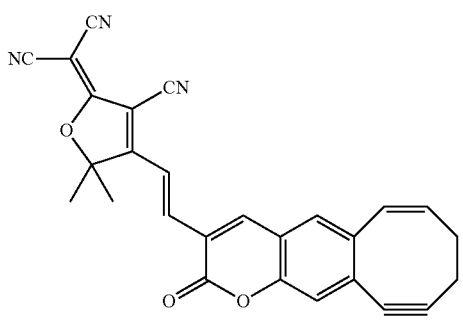
8. The compound of claim 7, wherein the compound is of the formula
(A1) 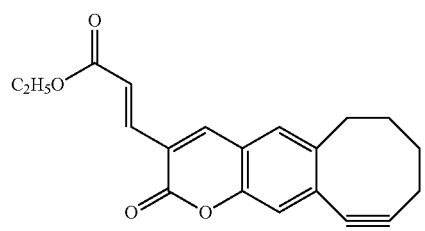
1 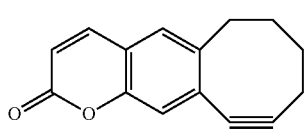 or
(A2) 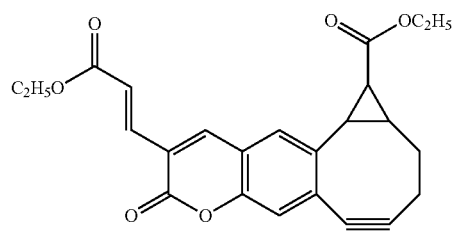
2 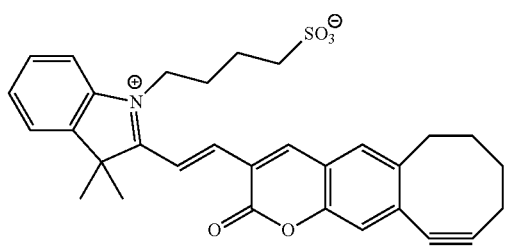
9. A compound of one of the following formulae:
(B) 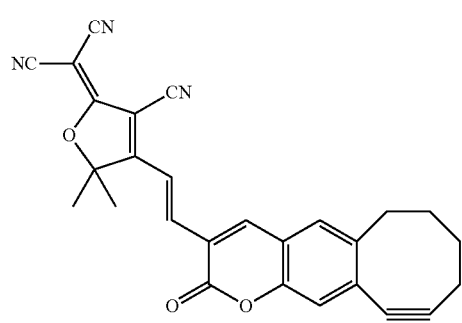
(III-a) 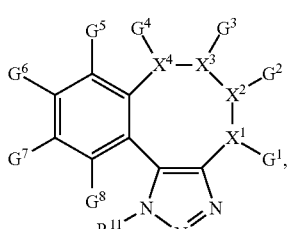
(C1)
(III-b) 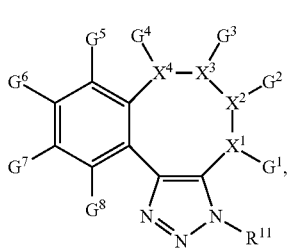

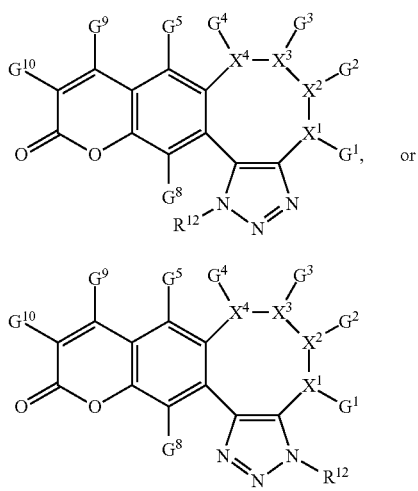

(IV-a)

(IV-b)

or a salt thereof,
wherein
$X_1$, $X_2$, $X_3$, and $X_4$ are in a 8-membered carbocycle or heterocycle; provided that when the 8-membered ring is a heterocycle, three of $X_1$, $X_2$, $X_3$, and $X_4$ are carbon atoms, and one of $X_1$, $X_2$, $X_3$, and $X_4$ is N, O, P, or S;

each of $G^1$, $G^2$, $G^3$ and $G^4$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —OR$^A$, —CH$_2$OR$^A$, —OC(O)R$^A$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, =O, =NOH, =N—OR$^A$, =N—NH$_2$, =N—NHR$^B$, =N—N(R$^B$)$_2$, and —NHSO$_2$R$^A$; or $G^1$ and $G^2$ are taken together with their intervening atoms to form an optionally substituted carbocycle or heterocycle; or $G^3$ and $G^4$ are taken together with their intervening atoms to form an optionally substituted carbocycle or heterocycle;

each of $G^5$ and $G^8$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, and —NHSO$_2$R$^A$;

each of $G^6$ and $G^7$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteoaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, and —NHSO$_2$R$^A$, or $G^6$ and $G^7$ are taken together with their intervening atoms to form an optionally substituted carbocycle or heterocycle;

each of $G^9$ and $G^{10}$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, optionally substituted heteoaryl, —OR$^A$, —CH$_2$OR$^A$, —OC(O)R$^C$, —SR$^A$, —N(R$^B$)$_2$, —N(R$^B$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, and —NHSO$_2$R$^A$, each of $R^{11}$ and $R^{12}$ is independently selected from the group consisting of hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, optionally substituted heterocyclylalkyl, optionally substituted heteoarylalkyl, —OR$^A$, —CH$_2$OR$^A$, —(CH$_2$)$_t$OC(O)R$^C$, —SR$^A$, —N(R$^B$)$_2$, —(CH$_2$)$_t$—N(R$^B$)C(O)R$^C$, —(CH$_2$)$_t$—C(O)N(R$^B$)$_2$, —CN, —NO$_2$, —C(O)R$^C$, —(CH$_2$)$_t$C(O)OR$^A$, —S(O)R$^C$, —SO$_2$R$^A$, —SO$_2$N(R$^B$)$_2$, and —NHSO$_2$R$^A$;

t is an integer of 1 to 5, inclusive;

each instance of R$^A$ is independently hydrogen, methyl or ethyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur;

each instance of R$^B$ is independently hydrogen, optionally substituted $C_1$-$C_6$ alkyl, optionally substituted alkenyl, optionally substituted alkynyl, optionally substituted heterocyclyl, optionally substituted aryl, or a nitrogen protecting group, or two R$^B$ taken together with the intervening nitrogen form a heterocycle;

each instance of R$^C$ is independently hydrogen, optionally substituted $C_1$-$C_6$ alkyl, optionally substituted alkenyl, optionally substituted alkynyl, optionally substituted heterocyclyl, optionally substituted aryl, or optionally substituted heteroaryl; and provided that when $G^1$ and $G^2$ are taken together with their intervening atoms to form an optionally substituted phenyl, $G^6$ and $G^7$ are taken together with their intervening atoms to form an optionally substituted heterocycle and $X^4$ is not N.

10. A compound of claim 1 or claim 9, wherein

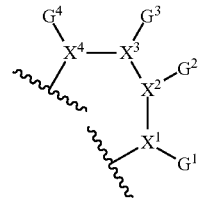

is —CH$_2$—CH$_2$—CH$_2$—CH$_2$—.

11. A method for detecting an azide-containing molecule comprising
(a) incubating a compound of claim 1 with a sample containing the azide-containing molecule under conditions allowing for ligation of the compound to an azido group of the molecule to form a triazole product; and
(b) detecting a fluorescent signal released from the triazole product.

12. The method of claim 11, wherein the incubating step is carried out in the absence of a metal catalyst.

13. The method of claim 11, wherein the compound is covalently linked to the azido group.

14. The method of claim 11, wherein the sample contains cells and the azide-containing molecule is located on or inside the cells.

15. The method of claim 11, wherein the compound is of Formula (I) or Formula (II).

16. The method of any one of claims 11-15, wherein the azide-containing molecule is a biomolecule.

17. The method of claim 16, wherein the biomolecule is a DNA, RNA, protein or glycan.

18. The method of claim 16, wherein the biomolecule is on a cell surface.

19. The method of claim 16, wherein the biomolecule is intracellular.

20. The method of claim 16, wherein the biomolecule is of avian, mammalian, viral, parasitical, fungal, or bacterial origin.

21. The method of claim 20, wherein the biomolecule is of human origin.

22. The method of claim 16, wherein the presence or absence of the biomolecule as measured by the imaging of the fluorescence signal is indicative of a disease state or physical condition.

23. The method of claim 21, wherein the disease is cancer or inflammation.

24. The method of claim 23, wherein the disease is rheumatoid arthritis.

25. The method of claim 11, wherein the molecule is an organic molecule.

26. A method for detecting an azide-containing molecule in a sample, comprising:
  (a) contacting a compound of claim 1 to a sample suspected of having an azide-containing molecule;
  (b) detecting a level of a fluorescent signal released from the sample by fluorescence imaging , and
  (c) determining presence of the azide-containing molecule in the sample, wherein an enhanced fluorescent signal as compared to a level of the fluorescent signal in the absence of the compound indicates presence of the azide-containing molecule.

\* \* \* \* \*